US011230725B2

(12) United States Patent
Florin et al.

(10) Patent No.: US 11,230,725 B2
(45) Date of Patent: Jan. 25, 2022

(54) CELL ENGINEERING USING MICRORNAS

(71) Applicant: Boehringer Ingelheim International GmbH, Ingelheim am Rhein (DE)

(72) Inventors: Lore Florin, Danbury, CT (US); Hitto Kaufman, Ulm (DE); Angelika Hausser, Stuttgart (DE); Monilola Olayioye, Ulm (DE); Michaela Strotbek, Asperg (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 436 days.

(21) Appl. No.: 15/727,056

(22) Filed: Oct. 6, 2017

(65) Prior Publication Data

US 2018/0119191 A1 May 3, 2018

Related U.S. Application Data

(63) Continuation of application No. 14/400,610, filed as application No. PCT/EP2013/061465 on Jun. 4, 2013, now abandoned.

(30) Foreign Application Priority Data

Jun. 6, 2012 (EP) .................................... 12171110

(51) Int. Cl.
| | | |
|---|---|---|
| *C12P 21/00* | (2006.01) | |
| *C12N 15/11* | (2006.01) | |
| *C12N 15/113* | (2010.01) | |
| *C12P 21/02* | (2006.01) | |
| *C07K 14/62* | (2006.01) | |
| *C07K 16/28* | (2006.01) | |
| *C12N 9/08* | (2006.01) | |

(52) U.S. Cl.
CPC .............. *C12P 21/00* (2013.01); *C07K 14/62* (2013.01); *C07K 16/2884* (2013.01); *C07K 16/2887* (2013.01); *C12N 9/0065* (2013.01); *C12N 15/111* (2013.01); *C12N 15/113* (2013.01); *C12N 2310/141* (2013.01); *C12N 2330/50* (2013.01); *C12P 21/02* (2013.01); *C12Y 111/01007* (2013.01)

(58) Field of Classification Search
CPC ...... C12N 15/113; C12N 15/85; C12N 15/86; C12N 2330/50; C12N 2310/141; C12N 15/67; C12N 15/87; C12N 15/907; C12N 15/63–15/815; C12P 21/00; C12P 21/005–21/02; C07K 16/00–16/468
See application file for complete search history.

(56) References Cited

U.S. PATENT DOCUMENTS

| | | | | |
|---|---|---|---|---|
| 10,858,653 | B2* | 12/2020 | Olayioye | C12N 9/22 |
| 2006/0160108 | A1* | 7/2006 | Romanov | C12Q 1/6897 |
| | | | | 435/6.13 |
| 2008/0236038 | A1* | 10/2008 | Pierce | C12N 1/20 |
| | | | | 47/58.1 FV |
| 2010/0093087 | A1* | 4/2010 | Elson | C07K 14/54 |
| | | | | 435/375 |

FOREIGN PATENT DOCUMENTS

| | | |
|---|---|---|
| EP | 2 208 499 A1 | 7/2010 |
| WO | 9208796 A1 | 5/1992 |
| WO | 9428143 A1 | 12/1994 |
| WO | 2008015662 A1 | 2/2008 |
| WO | 2008/061537 A2 | 5/2008 |
| WO | 2010/036939 A2 | 4/2010 |
| WO | 2010/101663 A2 | 9/2010 |
| WO | 2011/032100 A1 | 3/2011 |
| WO | 2011/149354 A1 | 12/2011 |
| WO | 2012/020308 A2 | 2/2012 |
| WO | 2012027206 A1 | 3/2012 |
| WO | 2010124231 A2 | 10/2012 |
| WO | 2013182553 A2 | 12/2013 |

OTHER PUBLICATIONS

Kim et al. Mammalian cell transfection: the present and the future. Analytical and Bioanalytical Chemistry, vol. 397, No. 8, pp. 3173-3178, Aug. 2010. (Year: 2010).*
BLOCK-iT™ Pol II miR RNAi Expression Vector Kits User Manual (Version F, Dec. 29, 2010, pages i-xii and 1-72, printed from https://assets.thermofisher.com/TFS-Assets/LSG/manuals/blockit_miRNAexpressionvector_man.pdf. (Year: 2010).*
Lim et al. Microarray analysis shows that some microRNAs downregulate large numbers of target mRNAs. Nature, vol. 433, pp. 769-773, 2005. (Year: 2005).*
Selbach et al. Widespread changes in protein synthesis induced by microRNAs. Nature, vol. 455, pp. 58-63, 2008. (Year: 2008).*
Rahbek et al. Bioresponsive hyperbranched polymers for siRNA and miRNA delivery. Journal of Drug Targeting, vol. 18, No. 10, pp. 812-820, Oct. 27, 2010. (Year: 2010).*
*Homo sapiens* pyridine nucleotide-disulphide oxidoreductase domain 2 (PYROXD2) mRNA. GenBank Accession No. NM_032709.2, publicly available Jun. 2, 2012, printed as p. 1/3-3/3. (Year: 2012).*
Thomas et al. Nature Structural & Molecular Biology, vol. 17, No. 10, pp. 1169-1174, Oct. 2010. (Year: 2010).*

(Continued)

*Primary Examiner* — Jennifer Dunston
(74) *Attorney, Agent, or Firm* — Shelley A. Jones

(57) ABSTRACT

The invention concerns the field of cell culture technology. It concerns RNA having a specific sequence, expression vectors encoding the RNA, production host cell lines comprising the RNA, and methods of producing recombinant biopharmaceutical products using engineered host cell with altered levels of the RNAs, such as small non-coding RNAs, preferably microRNAs (miRNAs). The invention also relates to engineered host cells with altered levels in one or more of the RNAs. Those cell lines have improved secretion and/or growth characteristics in comparison to control cell lines.

22 Claims, 19 Drawing Sheets

Specification includes a Sequence Listing.

(56) References Cited

OTHER PUBLICATIONS

Tian et al. MicroRNA-1285 inhibits the expression of p53 by directly targeting its 3' untranslated region. Biochemical and Biophysical Research Communications, vol. 396, pp. 435-439, 2010, including pp. 1-6 of Supplementary Data. (Year: 2010).*
Koh et al. Identification and expression analysis of miRNAs during batch culture of HEK-293 cells. Journal of Biotechnology, vol. 140, pp. 149-155, 2009. (Year: 2009).*
International Search Report and Written Opinion for corresponding PCT Application No. PCT/EP2013/061465, dated Dec. 5, 2013.
Boudreau et al., "Rapid Cloning and Validation of MicroRNA Shuttle Vectors: A Practical Guide" RNA Interference Techniques Humana Press Inc. pp. 19-37(2011).
Barron et al., "Engineering CHO cell growth and recombinant protein productivity by overexpression of miR-7". Journal of Biotechnology., vol. 151, No. 2., pp. 204-211 (2011).
Clarke et al., "Large scale microarray profiling and coexpression network analysis of CHO cells identifies transcriptional modules associated with growth and productivity" Journal of Biotechnology, vol. 155, No. 3, pp. 350-359 (2011).
Edelman et al., "The covalent structure of an entire gammaG immunoglobulin molecule" Proceedings of the National Academy of Sciences of the United States of America, vol. 63, pp. 78-85 (May 1969).
Ellison et al., "Linkage and sequence homology of two human immunoglobulin gamma heavy chain constant region genes" Proceedings of the National Academy of Sciences of the United States of America, vol. 79, 1982, pp. 1984-1988 (1982).
Gammell et al., "Initial identification of low temperature and culture stage induction of miRNA expression in suspension CHOK1 cells" Journal of Biotechnology, vol. 130, No. 3, 2007, pp. 213-218 (2007).
Johnson et al., "Conserved MicroRNAs in Chinese hamster ovary cell lines" Biotechnology and Bioengineering, vol. 108, No. 2, pp. 475-480 (2011).
Kaufman., "Selection and coamplification of heterologous genes in mammalian cells" Methods Enzymol., vol. 185, pp. 537-566 (1990).
Lagos-Quintana et al., "Identification of tissue-specific microRNAs from mouse" Current Biology., vol. 12, No. 9, pp. 735-739 (2002).
Pau et al., "The human cell line PER.C6 provides a new manufacturing system for the production of influenza virus vaccines" Vaccines, vol. 19, pp. 2716-2721 (2001).
Pitot et al., "Hepatomas in tissue culture compared with adapting liver in vivo" National Cancer Institute Monograph, vol. 13, pp. 229-245, (1964).
Reuber, "A Transplantable Bile-Secreting Hepatocellular Carcinoma in the Rat" Journal of the National Cancer Institute, vol. 26, pp. 891-899, (1961).
Urlaub et al., "Effect of gamma rays at the dihydrofolate reductase locus: Deletions and inversions" Somatic Cell and Molecular Genetics, vol. 12, No. 6, pp. 555-566, (Nov. 1986).
Woelfel et al., "CAP-T cell expression system: a novel rapid and versatile human cell expression system for fast and high yield transient protein expression" BMC Proc., vol. 5, No. 8, p. 133 (2pages) (2011).
Zuker., "Mfold web server for nucleic acid folding and hybridization prediction" Nucleic Acids Research, vol. 31, No. 13, pp. 3406-3415 (2003).

Vaibhav Jadhav, "A Screening Method to Assess Biological Effects of MicroRNA Overexpression in Chinese Hamster Ovary Cells" Wiley Periodicals, Inc., Biotechnology and Bioengineering, vol. 109, No. 6 pp. 1376-1385 (Jun. 2012).
Dethardt Müller, et al., "MicroRNAs as targets for engineering of CHO cell factories", Trends in Biotechnology vol. 26 No 7, pp. 359-365 (2008).
International Preliminary Report on Patentability and Written Opinion for corresponding PCT Application No. PCT/EP2013/061465, dated Dec. 18, 2014.
Elvin A. Kabat, "Antibody Complementarity and Antibody Structure" Departments of Microbiology, Genetics and Development and Neurology, College of Physicians and Surgeons Columbia University. pp. S25-S36 (1988).
Office Action for corresponding EP Application No. 13728354.5, 19 pages, dated Dec. 1, 2016.
Yojiro Hashiguchi et al.: "Down-regulation of miR-125a-3p in human gastric cancer and its clinicopathological significance", International Journal of Oncology, vol. 40, pp. 1477-1482 (2012).
B.L. Mihelich et al.: "miR-183-96-182 cluster is overexpressed in prostate tissue and regulates zinc homeostasis in prostate cells", Journal of Biological Chemistry, vol. 286, No. 52, pp. 44503-44511 (Dec. 30, 2011).
K. P. Jensen et al.: "Human miR-1271 is a miR-96 paralog with distinct non-conserved brain expression pattern", Nucleic Acids Research, vol. 39, No. 2, pp. 701-711 (2011) (published online Sep. 2010).
Shu Tian et al.: "MicroRNA-1285 inhibits the expression of p53 by directly targeting its 3' untranslated region", Biochemical and Biophysical Research Communications, vol. 396, No. 2, pp. 435-439 (2010).
Morin et al. Application of massively parallel sequencing to micro RNA profiling and discovery in human embryonic stem cells. Genome Research, vol. 18, pp. 610-621, 2008.
Mendenhall et al. Packaging HIV- of FIV-based lentivector expression constructs & transduction fo VSV-G pseudotyped viral particles. Journal of Visualized Experiments, vol. 62, e3171, Apr. 8, 2012.
Gori et al. In vivo selection of human embryonic stem cell-derived cells expressing reductase. Gene Therapy, vol. 17, pp. 238-249, 2010.
Strotbek, M. MicroRNAs to boost the productivity of Chinese hamster ovary producer cells. Dissertation, 2013, http://dx.doi.org/1 0.18419/opus-2322.
Barron, Niall et al. "MicroRNAs: tiny targets for engineering CHO cell phenotypes?" (2011) Biotechnology Letters, 33, 11-21.
Hackl, Matthias et al. "miRNAs—pathway engineering of CHO cell factories that avoids translational burdening" (2012) Trends in Biotechnology, vol. 30, No. 8, 405-406.
Lin, Nan et al. "Effects of Inhibiting Two Cell Cycle Modulating microRNAs in Recombinant Human IgG Producing Chinese Hamster Ovary Cells" (2011) Sigma-Aldrich, safcglobal.com, poster 1 pg.
Strotbek, Michaela, et al. "Stable microRNA expression enhances therapeutic antibody productivity of Chinese hamster ovary cells" (2013) Metabolic Engineering, 20, 157-166.
Zucker, Michael "Mfold web server for nucleic acid folding and hybridization prediction" (2003) Nucleic Acids Research, vol. 31, No. 13, 3406-3415.

* cited by examiner

Figure 1B

| microRNA | MIMAT | microRNA sequence | result |
|---|---|---|---|
| miR-125a-3p | 0004602 | ACAGGUGAGGUUCUUGGGAGCC | 1,41 |
| miR-149 | 0000450 | UCUGGCUCCGUGUCUUCACUCCC | 1,54 |
| miR-1271 | 0005796 | CUUGGCACCUAGCAAGCACUCA | 1,48 |
| miR-1275 | 0005929 | GUGGGGGAGAGGCUGUC | 1,48 |
| miR-1285 | 0005876 | UCUGGGCAACAAAGUGAGACCU | 1,43 |
| miR-1287 | 0005878 | UGCUGGAUCAGUGGUUCGAGUC | 1,95 |
| miR-1293 | 0005883 | UGGGUGGUCUGGAGAUUUGUGC | 1,44 |
| miR-183 | 0000261 | UAUGGCACUGGUAGAAUUCACU | 1,52 |
| miR-185* | 0004611 | AGGGGCUGGCUUUCCUCUGGUC | 1,53 |
| miR-193b* | 0004767 | CGGGGUUUUGAGGGCGAGAUGA | 1,36 |
| miR-1978 | not available | GGUUUGGUCCUAGCCUUUCUA | 1,72 |
| miR-23b* | 0004587 | UGGGUUCCUGGCAUGCUGAUUU | 1,42 |
| miR-299-3p | 0000687 | UAUGUGGGAUGGUAAACCGCUU | 1,60 |
| miR-365* | 0022833 | AGGGACUUUCAGGGGCAGCUGU | 1,76 |
| miR-450b-3p | 0004910 | UUGGGAUCAUUUUGCAUCCAUA | 1,49 |
| miR-557 | 0003221 | GUUUGCACGGGUGGGCCUUGUCU | 1,45 |
| miR-612 | 0003280 | GCUGGGCAGGGCUUCUGAGCUCCUU | 1,87 |
| miR-644a | 0003314 | AGUGUGGCUUUCUUAGAGC | 1,49 |
| miR-885-3p | 0004948 | AGGCAGCGGGGUGUAGUGGAUA | 1,60 |
| miR-892a | 0004907 | CACUGUGUCCUUUCUGCGUAG | 1,50 | parental

-miR557-miR557

-neg. control miRNA

-miR557-miR1287

-miR1287-miR1287

-miR1978-miR1978

-miR557-miR1978

-miR1287-miR1978

SEQUENCE LISTING

<160> NUMBER OF SEQ ID NOS: 26

<210> SEQ ID NO 1
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-125a-3p"
      /organism="Homo sapiens"

<400> SEQUENCE: 1
acaggugagg uucuugggag cc                                              22

<210> SEQ ID NO 2
<211> LENGTH: 23
<212> TYPE: RNA
<213> ORGANISM: Homo sapiens
<220> FEATURE:
<221> NAME/KEY: source
<222> LOCATION: 1..23
<223> OTHER INFORMATION: /mol_type="unassigned RNA"
      /note="miR-149"
      /organism="Homo sapiens"

<400> SEQUENCE: 2
ucuggcuccg ugucuucacu ccc                                             23

<210> SEQ ID NO 3
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-1271"
      /organism="Homo sapiens"

<400> SEQUENCE: 3
cuuggcaccu agcaagcacu ca                                              22

<210> SEQ ID NO 4
<211> LENGTH: 17
<212> TYPE: RNA
<213> ORGANISM: Homo sapiens
<220> FEATURE:
<221> NAME/KEY: source
<222> LOCATION: 1..17
<223> OTHER INFORMATION: /mol_type="unassigned RNA"
      /note="miR-1275"
      /organism="Homo sapiens"

<400> SEQUENCE: 4 guggggaga ggcuguc                                                     17

<210> SEQ ID NO 5
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-1285"
      /organism="Homo sapiens"

<400> SEQUENCE: 5

```
ucugggcaac aaagugagac cu                                               22

<210> SEQ ID NO 6
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-1287"
      /organism="Homo sapiens"

<400> SEQUENCE: 6
ugcuggauca ugguucgag uc                                                22

<210> SEQ ID NO 7
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-1293"
      /organism="Homo sapiens"

<400> SEQUENCE: 7
ugggugguCu ggagauuugu gc                                               22

<210> SEQ ID NO 8
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-183"
      /organism="Homo sapiens"

<400> SEQUENCE: 8
uauggcacug guagaauuca cu                                               22

<210> SEQ ID NO 9
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-185*"
      /organism="Homo sapiens"

<400> SEQUENCE: 9
aggggcuggc uuuccucugg uc                                               22

<210> SEQ ID NO 10
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-193b*"
      /organism="Homo sapiens"
```

```
<400> SEQUENCE: 10
cgggguuuug agggcgagau ga                                          22

<210> SEQ ID NO 11
<211> LENGTH: 21
<212> TYPE: RNA
<213> ORGANISM: Artificial Sequence
<220> FEATURE:
<221> NAME/KEY: source
<222> LOCATION: 1..21
<223> OTHER INFORMATION: /mol_type="unassigned RNA"
      /note="miR-1978"
      /organism="Artificial Sequence"

<400> SEQUENCE: 11
gguuuggucc uagccuuucu a                                           21

<210> SEQ ID NO 12
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-23b*"
      /organism="Homo sapiens"

<400> SEQUENCE: 12
uggguuccug gcaugcugau uu                                          22

<210> SEQ ID NO 13
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-299-3p"
      /organism="Homo sapiens"

<400> SEQUENCE: 13 uauguggau gguaaaccgc uu                                           22

<210> SEQ ID NO 14
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-365*"
      /organism="Homo sapiens"

<400> SEQUENCE: 14
agggacuuuc aggggcagcu gu                                          22

<210> SEQ ID NO 15
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-450b-3p"
      /organism="Homo sapiens"
```

```
<400> SEQUENCE: 15
uugggaucau uuugcaucca ua                                              22

<210> SEQ ID NO 16
<211> LENGTH: 23
<212> TYPE: RNA
<213> ORGANISM: Homo sapiens
<220> FEATURE:
<221> NAME/KEY: source
<222> LOCATION: 1..23
<223> OTHER INFORMATION: /mol_type="unassigned RNA"
      /note="miR-557"
      /organism="Homo sapiens"

<400> SEQUENCE: 16
guuugcacgg gugggccuug ucu                                             23

<210> SEQ ID NO 17
<211> LENGTH: 25
<212> TYPE: RNA
<213> ORGANISM: Homo sapiens
<220> FEATURE:
<221> NAME/KEY: source
<222> LOCATION: 1..25
<223> OTHER INFORMATION: /mol_type="unassigned RNA"
      /note="miR-612"
      /organism="Homo sapiens"

<400> SEQUENCE: 17
gcugggcagg gcuucugagc uccuu                                           25

<210> SEQ ID NO 18
<211> LENGTH: 19
<212> TYPE: RNA
<213> ORGANISM: Homo sapiens
<220> FEATURE:
<221> NAME/KEY: source
<222> LOCATION: 1..19
<223> OTHER INFORMATION: /mol_type="unassigned RNA"
      /note="miR-644a"
      /organism="Homo sapiens"

<400> SEQUENCE: 18
aguguggcuu ucuuagagc                                                  19

<210> SEQ ID NO 19
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="unassigned RNA"
      /note="miR-885-3p"
      /organism="Homo sapiens"

<400> SEQUENCE: 19
aggcagcggg guguagugga ua                                              22

<210> SEQ ID NO 20
<211> LENGTH: 21
<212> TYPE: RNA
<213> ORGANISM: Homo sapiens
<220> FEATURE:
<221> NAME/KEY: source
<222> LOCATION: 1..21
<223> OTHER INFORMATION: /mol_type="unassigned RNA"
      /note="miR-892a"
```

/organism="Homo sapiens"

<400> SEQUENCE: 20 cacuguguccc uuucugcgua g                                          21

<210> SEQ ID NO 21
<211> LENGTH: 68
<212> TYPE: DNA
<213> ORGANISM: Artificial Sequence
<220> FEATURE:
<221> NAME/KEY: source
<222> LOCATION: 1..68
<223> OTHER INFORMATION: /mol_type="unassigned DNA"
      /note="synthetic"
      /organism="Artificial Sequence"

<400> SEQUENCE: 21
tgctggtttg cacgggtggg ccttgtctgt tttggccact gactgacaga caaggcccac    60
gtgcaaac                                                             68

<210> SEQ ID NO 22
<211> LENGTH: 68
<212> TYPE: DNA
<213> ORGANISM: Artificial Sequence
<220> FEATURE:
<221> NAME/KEY: source
<222> LOCATION: 1..68
<223> OTHER INFORMATION: /mol_type="unassigned DNA"
      /note="synthetic"
      /organism="Artificial Sequence"

<400> SEQUENCE: 22
cctggtttgc acgtgggcct tgtctgtcag tcagtggcca aaacagacaa ggcccacccg    60
tgcaaacc                                                             68

<210> SEQ ID NO 23
<211> LENGTH: 66
<212> TYPE: DNA
<213> ORGANISM: Artificial Sequence
<220> FEATURE:
<221> NAME/KEY: source
<222> LOCATION: 1..66
<223> OTHER INFORMATION: /mol_type="unassigned DNA"
      /note="synthetic"
      /organism="Artificial Sequence"

<400> SEQUENCE: 23
tgctgtgctg gatcagtggt tcgagtcgtt ttggccactg actgacgact cgaaccacat    60
ccagca                                                               66

<210> SEQ ID NO 24
<211> LENGTH: 66
<212> TYPE: DNA
<213> ORGANISM: Artificial Sequence
<220> FEATURE:
<221> NAME/KEY: source
<222> LOCATION: 1..66
<223> OTHER INFORMATION: /mol_type="unassigned DNA"
      /note="synthetic"
      /organism="Artificial Sequence"

<400> SEQUENCE: 24
cctgtgctgg atgtggttcg agtcgtcagt cagtggccaa aacgactcga accactgatc    60
cagcac                                                               66

```
<210> SEQ ID NO 25
<211> LENGTH: 64
<212> TYPE: DNA
<213> ORGANISM: Artificial Sequence
<220> FEATURE:
<221> NAME/KEY: source
<222> LOCATION: 1..64
<223> OTHER INFORMATION: /mol_type="unassigned DNA"
      /note="synthetic"
      /organism="Artificial Sequence"

<400> SEQUENCE: 25
tgctgggttt ggtcctagcc tttctagttt tggccactga ctgactagaa aggctaacca    60
aacc                                                                 64

<210> SEQ ID NO 26
<211> LENGTH: 64
<212> TYPE: DNA
<213> ORGANISM: Artificial Sequence
<220> FEATURE:
<221> NAME/KEY: source
<222> LOCATION: 1..64
<223> OTHER INFORMATION: /mol_type="unassigned DNA"
      /note="synthetic"
      /organism="Artificial Sequence"

<400> SEQUENCE: 26
cctgggtttg gttagccttt ctagtcagtc agtggccaaa actagaaagg ctaggaccaa    60
accc                                                                 64
```

CELL ENGINEERING USING MICRORNAS

CROSS-REFERENCE TO RELATED APPLICATIONS

This application is a continuation of U.S. patent application Ser. No. 14/400,610 filed Nov. 12, 2014, incorporated herein by reference in its entirety, which is the National Stage of International Application No. PCT/EP2013/061465 filed Jun. 4, 2013.

SEQUENCE LISTING

The instant application contains a Sequence Listing which has been submitted electronically in ASCII format and is hereby incorporated by reference in its entirety. Said ASCII file, created on Jun. 4, 2013, is named sequence-listing-boe14803pct.txt and is 8 KB in size.

TECHNICAL FIELD

The invention relates to the field of cell culture technology. It concerns RNA, expression vectors encoding said RNA, production host cell lines comprising said RNA, and methods of producing recombinant biopharmaceutical products using engineered host cells with altered levels of RNA, preferably small non-coding RNA, especially microRNAs (miRNAs). The invention also relates to engineered host cells with altered levels in one or more RNAs, preferably small non-coding RNAs, especially microRNAs. Those cell lines have improved secretion and/or growth characteristics in comparison to control cell lines.

BACKGROUND

Improving titers of therapeutic proteins in production and thus making processes more efficient is a clear goal in industry. More efficient processes can lead to reduced costs and shortened timelines to supply protein material for clinical studies and markets. As overall yields in production processes are determined on the one hand by cell specific productivity of the individual cell as well as the number of viable cells present in the process, strategies to improve production efficiency usually aim to increase either of these two parameters, without negatively affecting the other.

However, one of the challenges associated with modifying the behaviour of cells to achieve favourable phenotypes for the production of recombinant proteins is the complex nature of intra-cellular regulating circuits. Targeting the expression of one gene or protein may not be sufficient to alter the phenotype of a cell unless it is a rate-limiting factor in a critical pathway or it is a transcription factor with the potential to alter expression of a whole set of target genes.

This explains the current interest in microRNAs (also referred to as "miRNAs") as a potential opportunity to engineer networks of genes in order to achieve complex phenotypic changes in mammalian cells (Müller et al, 2008).

miRNAs are small (~22nt), non-coding RNAs that regulate gene expression at the level of mRNA degradation and protein translation. How miRNAs contribute to the regulation of cell phenotypes is subject of extensive research. Apparently, the mechanism is quite complex as each miRNA can regulate multiple, even up to 100 genes and hundreds of miRNA genes are predicted to be present in mammals. For example, the human genome is estimated to contain 700-1,000 miRNA genes and in silico predictions suggest that as many as 30-50% of all proteins may be sensitive to miRNA effects, establishing them as a significant layer of control within the cell.

The first microRNA was discovered in *C. elegans* in 1993 and over the last years, microRNAs have been associated with various processes including development, proliferation, differentiation and cell death. In 2007, Gammel et al. isolated and sequenced the first microRNA from CHO cells (Gammel et al, 2007) and since then, several studies linked microRNAs with different states or phases in production processes (Gammel et al, 2007; Clarke et al, 2011; Johnson et al, 2011).

The ability of RNAs, especially microRNAs, to influence gene expression is now recognized as a fundamental mechanism of regulation in cells. In contrast to manipulation (over-expression, knock-out or knock-down) of one or several individual genes in a cell, which in several cases turned out not to be sufficiently effective, microRNAs through their ability of targeting ~100 target genes in a cell, could provide an elegant and highly efficient solution to engineer cell behavior.

One striking advantage of using RNAs, such as miRNAs, instead of functional proteins is that they do not compete for the translational machinery that is required to express the recombinant therapeutic protein product. miRNAs are short, of nucleic acid nature and can be expressed from simple genetic constructs. Thus, the translation apparatus is not overloaded and the cell not burdened with additional energy consumption for gene transcription and protein synthesis.

In the literature, there are reports indicating that the functional role of individual microRNAs may be cell- or tissue-specific. For example, antisense inhibition of miR-21 and miR-24 have been reported to result in increased growth rates of HeLa cells, whereas other reports found that their over-expression supported tumour cell growth.

Only recently, a group at the University of Dublin published a first report on a microRNA engineering approach in CHO producer cells where they showed that in transient experiments, over-expression of cgr-miR-7 resulted in higher levels of a reporter protein (increased production normalised per cell); however, the total yield was not increased due to a concomitant reduction in cell numbers (Barron et al., 2011). Also, they did not demonstrate stable transfections, which would be a requirement for application in industrial processes, nor was the production of a therapeutically relevant protein analyzed.

In the same year, Lin et al (2011) inhibited the expression of two endogenous microRNAs in CHO and in one case saw a mild increase in IgG production.

Another group from the University of Vienna analysed transient transfection with CHO miRNAs (cgr-miR-17, cgr-miRNA-221, cgr-miR-21, and cgr-miR-210) in CHO cells and found that over-expression of cgr-miR-17 increased cell growth. However, they did not observe an increase in specific productivity and did not demonstrate an effect for stably expressed miRNAs. Furthermore, none of these publications used human miRNAs.

Hence, there is a need for improving recombinant protein production in mammalian cells, by increasing the specific productivity and the total yield (i.e., titer or concentration) of the protein, which is generally applicable and not dependent on the individual cell line or protein to be produced. It is an objective of the present invention to provide heterologous human microRNAs to engineer producer cell behaviour, wherein over-expression (not inhibition) of the specific microRNAs has a positive impact on cell productivity.

It was found that the RNAs, particularly the microRNAs according to the present invention, exert a positive role on protein production and/or secretion in more than one cell line. Surprisingly, the RNAs (microRNAs) provided herein show a functional benefit not only in CHO cells (which are used for screening), but also in other rodent and human cell lines.

SUMMARY OF THE INVENTION

The above objects are solved by the RNAs, expression vectors, mammalian cells, methods and uses according to the present invention. By virtue of the RNAs provided herein, it is now possible to engineer mammalian cells to improve their cell productivity and/or cell growth. This results in a higher yield of the protein of interest produced by these cells. The use of the RNAs provided herein is particularly suited for engineering protein producer cell lines, and for the generation of improved host cell lines for the production of proteins of interest. Further, the invention relates to the modification of mammalian producer cells to increase the levels of specific RNAs (listed in FIG. 1B), preferably of small non-coding RNAs, more preferably microRNAs, to modulate cell productivity and/or cell growth. The invention is based on functional screening of a library of human microRNAs in antibody-producing CHO cells, which resulted in 20 RNAs, reproducibly allowing for improved IgG product titers when overexpressed (e.g. transiently or stably) in producer cell lines, such as CHO cells. Furthermore, it is demonstrated herein that the RNA-mediated, specifically miRNA-mediated, production improvement is not product-dependent, but increases specific production rates for example in an antibody producing cell and also in HSA (human serum albumin) expressing cells (exemplified in FIG. 4). Engineering the production host cells by transiently or stably increasing the level of one or more of these 20 selected RNAs allows to achieve higher productivities and/or secretion without negatively affecting growth characteristics.

In a first aspect the present invention relates to a ribonucleic acid (RNA) selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20, wherein said RNA leads to an increase in the production and/or secretion of a therapeutic protein of interest from a mammalian cell.

In second aspect the present invention relates to a mammalian expression vector comprising a RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20, wherein said vector comprises a polynucleotide sequence encoding the RNA. In a preferred embodiment, the RNA encoded by the expression vector is a non-coding RNA, more preferably the non-coding RNA is a miRNA. The RNA encoded by the mammalian expression vector of the invention leads to an increase in the production and/or secretion of a therapeutic protein of interest in a mammalian expression system. Although not strictly mandatory the protein of interest or the RNA may further be operably linked to an amplifiable selection marker. Alternatively the expression vector may comprise a selection marker gene, wherein the selection marker gene may be an amplifiable selection marker gene, such as a glutamine synthetase gene or a dihydrofolate reductase gene. In a preferred embodiment of this aspect, the RNA is selected from the group consisting of: SEQ ID NO: 1, SEQ ID NO: 3, SEQ ID NO: 6, SEQ ID NO:8, SEQ ID NO:9, SEQ ID NO: 10, SEQ ID NO: 11, SEQ ID NO:14, SEQ ID NO: 16, SEQ ID NO: 17, SEQ ID NO: 18, and SEQ ID NO: 19. In a more preferred embodiment the RNA is miR-1271 (SEQ ID NO: 3), miR-1287 (SEQ ID NO:6), miR-1978 (SEQ ID NO:11), or miR-557 (SEQ ID NO:16). In a more preferred embodiment the RNA miR-1287 (SEQ ID NO:6), miR-1978 (SEQ ID NO:11), or miR-557 (SEQ ID NO:16). In an even more preferred embodiment the RNA is miR-1287 (SEQ ID NO:6). In another even more preferred embodiment, the RNA is miR-557 (SEQ ID NO:16).

Although not mandatory the mammalian expression vector of the present invention may comprise a combination of several identical or different RNAs selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20. Specifically, the expression vector may comprise a polynucleotide sequence encoding a combination of two or more of the RNAs, wherein said RNAs may be identical or different. In a preferred embodiment the RNAs are selected from the group consisting of: SEQ ID NO: 1, SEQ ID NO: 3, SEQ ID NO: 6, SEQ ID NO:8, SEQ ID NO:9, SEQ ID NO: 10, SEQ ID NO: 11, SEQ ID NO:14, SEQ ID NO: 16, SEQ ID NO: 17, SEQ ID NO: 18, and SEQ ID NO: 19. In another preferred embodiment the RNAs are selected from the group consisting of: miR-1271 (SEQ ID NO: 3), miR-1287 (SEQ ID NO:6), miR-1978 (SEQ ID NO:11) and miR-557 (SEQ ID NO:16). In certain embodiments the mammalian expression vector of the invention further comprises at least one gene of interest. Preferably the RNA or the RNA encoded by the expression vector is a non-coding RNA, more preferably the non-coding RNA is a miRNA.

The invention further relates to a mammalian expression vector comprising a polynucleotide sequence encoding any of the RNAs of the first aspect. The expression vector may also comprise a polynucleotide sequence encoding a combination of two or more of the RNAs of the first aspect, wherein the RNAs may be identical or different.

In another aspect the present invention relates to a mammalian cell comprising one or more RNAs selected from one or more of the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20, wherein typically the RNA is a heterologous or transfected RNA. In a preferred embodiment the cell is stably transfected with an expression vector encoding said one or more RNA. Preferably, the one or more RNAs of this aspect are non-coding RNAs, more preferably the non-coding RNAs are miRNAs.

In a preferred embodiment the one or more RNA is selected from the group consisting of: SEQ ID NO: 1, SEQ ID NO: 3, SEQ ID NO: 6, SEQ ID NO:8, SEQ ID NO:9, SEQ ID NO: 10, SEQ ID NO: 11, SEQ ID NO:14, SEQ ID NO: 16, SEQ ID NO: 17, SEQ ID NO: 18, and SEQ ID NO:

19, preferably the RNA is selected from the group consisting of: miR-1271 (SEQ ID NO: 3), miR-1287 (SEQ ID NO:6), miR-1978 (SEQ ID NO:11), and miR-557 (SEQ ID NO:16). In a more preferred embodiment the one or more RNA is miR-1287 (SEQ ID NO:6), miR-1978 (SEQ ID NO:11), miR-557 (SEQ ID NO:16) or a combination thereof, even more preferably miR-1287 (SEQ ID NO:6) and/or miR-557 (SEQ ID NO:16). In another embodiment the mammalian cell may comprise the mammalian expression vector of the invention. In yet another embodiment the mammalian cell may further stably express a protein of interest. Although the mammalian cell of the invention may be a rodent or a human cell, in a preferred embodiment the cell is a rodent cell, more preferably a hamster cell and even more preferably a CHO cell, such as a CHO-DG44. In certain embodiments the human cell is a HEK-293 cell, a PER.C6 or a CAP cell.

In yet another aspect the invention relates to a method of developing a stably transfected mammalian cell comprising the following steps:
(a) transfecting at least one RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 into the mammalian cell,
(b) cultivating said cell for an initial period of time in the presence of selective pressure, and
(c) selecting a high-producing transfected cell.

Preferably the RNA is a non-coding RNA, more preferably the non-coding RNA is a miRNA. In a preferred embodiment the mammalian cell in step (a) is stably transfected with an expression vector encoding said RNA, wherein the expression vector may be the expression vector of the invention. In one embodiment the mammalian cell in step (a) is a producer host cell comprising at least one expression vector comprising at least one gene of interest.

In yet another aspect the invention relates to a method of producing a protein of interest, characterised by the following steps:
(a) transfecting at least one RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 and at least one expression vector comprising at least one gene of interest into a mammalian cell,
(b) selecting a highly-productive transfected cell, and
(c) cultivating the highly-productive transfected cell obtained in step (b) under conditions which allow expression of the gene(s) of interest, and optionally
(d) harvesting and purifying the protein of interest.

Preferably the RNA is a non-coding RNA, more preferably, the non-coding RNA is a miRNA. In a preferred embodiment the transfection step (a) comprises transfecting an expression vector encoding said RNA. In a more preferred embodiment the mammalian cell in step (a) is stably transfected with the expression vector encoding said RNA, wherein the expression vector may be the expression vector of the invention. In one embodiment the expression vector comprising at least one gene of interest of step (a) may also encode the at least one RNA of step (a). Alternatively, transfecting the RNA into the mammalian cell may be done after, prior to or simultaneously to transfecting the gene of interest.

In yet another related aspect, the invention relates to a method of preparing and selecting a recombinant mammalian cell, comprising the following steps:
(a) transfecting a mammalian cell with genes that encode at least a protein/product of interest and a selectable marker, wherein the cell is co-transfected with at least one RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20,
(b) selecting a cell with co-integrated genes by cultivating the cell in the presence of a selective agent, and
(c) cultivating the cell under conditions which enable expression of the (different) genes.

Preferably, the RNA is a non-coding RNA, more preferably the non-coding RNA is a miRNA. In one embodiment the selectable marker confers resistance to neomycin, puromycin, bleomycin, zeocin or blasticidin. In an alternative embodiment the selectable marker may be an amplifiable selectable marker and the method further comprises an additional step (b') between steps (b) and (c), comprising amplifying the co-integrated genes by cultivating the cell in the presence of an agent, which allows the amplification of the amplifiable selectable marker gene. The amplifiable selectable marker gene may encode the amplifiable selectable markers DHFR or GS.

In a preferred embodiment the mammalian cell in step (a) is stably transfected with the expression vector encoding said at least one RNA, wherein the expression vector may be the expression vector of the invention. Transfecting the RNA into the mammalian cell may be done after, prior to or simultaneously to transfecting the gene of interest. The protein of interest in any one of the above methods of the inventions may be a recombinant therapeutic protein, such as an antibody or an Fc-fusion protein.

In one embodiment of any of the methods of the invention, the production and/or secretion of the protein of interest is increased by 10%, 20%, 50%, 100%, 200%, 400% compared to a control cell, which is not transfected with at least one RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20. In yet another aspect, the invention relates to a use of a RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 as a production-promoting element for the preparation of a recombinant protein of interest in a mammalian cell. In one embodiment the RNA of the invention is used for increasing the production and/or secretion of a protein of interest from a mammalian cell.

In yet another aspect, the invention relates to a use of the mammalian cell of the invention for producing a protein of interest, wherein the protein of interest may be a recombinant therapeutic protein, such as an antibody, an antibody fragment, an antibody fusion protein, an antibody conjugate or an Fc-fusion protein. In yet another aspect, the invention relates to the use of the RNA of the invention for the production of a non-human transgenic animal, preferably a mammal. Preferably, the RNA in any of the uses of the invention is a non-coding RNA, more preferably the non-coding RNA is a miRNA.

Generally, the RNAs (microRNAs) provided in this invention increase the yield of a protein of interest, such as a secreted therapeutic protein, in production processes based on eukaryotic cells by increasing the productivity of the cell, and/or cell growth. This reduces the cost of goods of such processes and at the same time it reduces the number of batches that need to be produced to generate the material needed for research studies, diagnostics, clinical studies or market supply of a therapeutic protein. Thus, the microRNAs, mammalian cells, methods and uses provided herein find application in the production of recombinant biological products, especially recombinant therapeutic protein products.

The invention may furthermore speed up drug development since the generation of sufficient amounts of material for pre-clinical studies is a critical work package with regard to overall development timelines.

The RNAs (miRNAs), cells and methods of the invention can further be used for the generation of one or several specific proteins for either diagnostic purposes, research purposes (target identification, lead identification, lead optimization) or manufacturing therapeutic proteins either on the market or in clinical development.

Figure 1A:
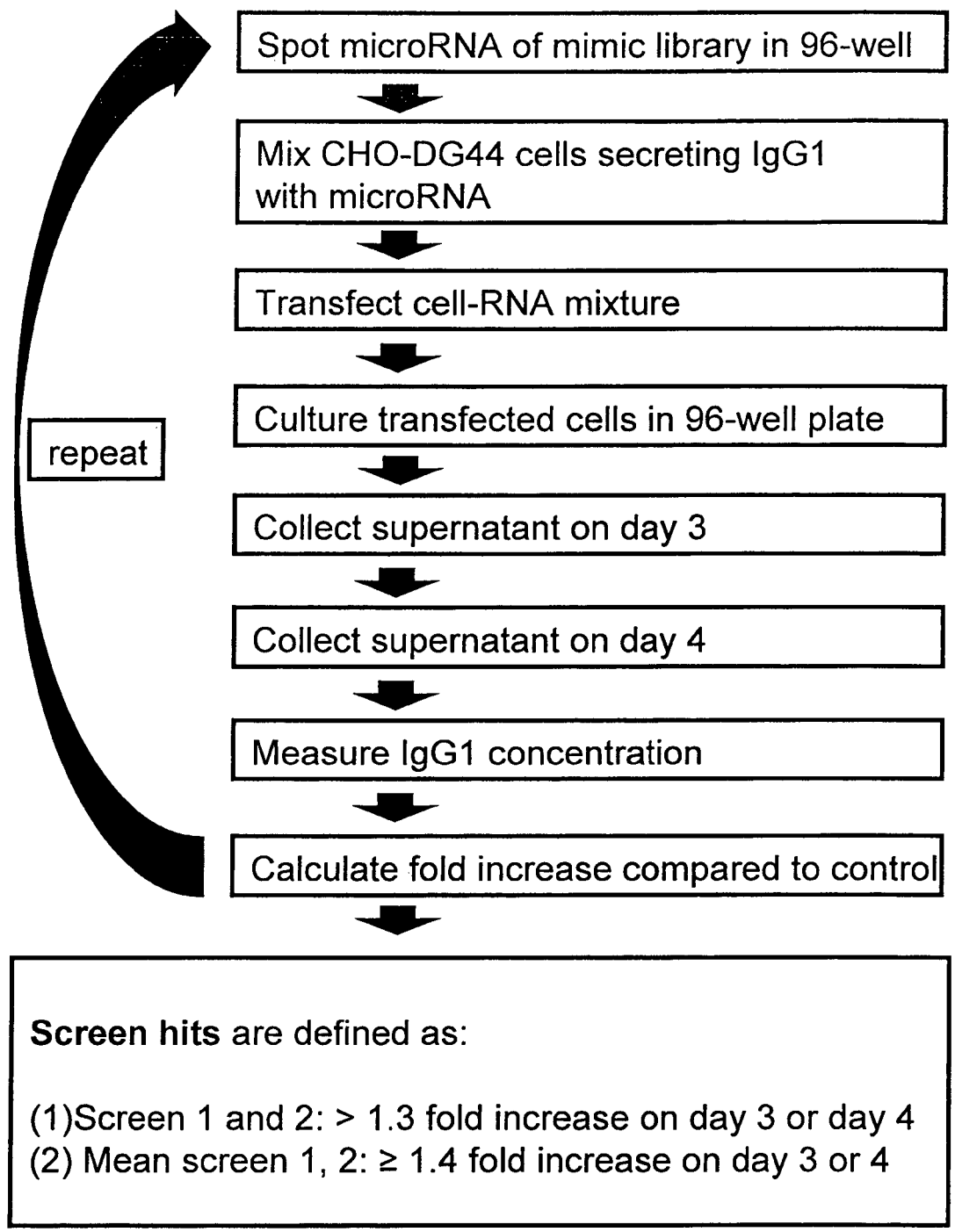
FIG. 1A: FIRST MICRORNA SCREEN IN BIWA4-PRODUCING CHO CELLS

CHO-DG44 cells secreting a human IgG1 antibody (BIWA4) are transiently transfected with a human mimic microRNA library consisting of 879 human microRNAs according to the official microRNA database mirbase. Antibody concentrations in the supernatant of the transfected cells are determined and consequently any positive effect on the antibody titer can be correlated with the expression of a specific mature microRNA.

FIG. 1B: HITS OF THE MICRORNA LIBRARY SCREEN.

20 miRNAs, namely, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20, are defined as hits, when they show more than 1.4 fold increased antibody titer on day 3 or 4 after transfection compared to control (mean of two independent experiments, see last column) and additionally more than 1.3 fold increased antibody titers in each of the two screens. Sequences, accession numbers and names of the miRNAs as stored in the mirbase database are listed.

FIG. 2: SECONDARY SCREEN IN BIWA4-PRODUCING CHO CELLS.

CHO-DG44 cells stably secreting an IgG1 antibody (BIWA4) are transfected with each of the 20 miRNA hits (see FIG. 1B) in quadruplicates. Cell density and viability are determined by cell counting and trypane blue exclusion. Antibody concentrations in the supernatants are determined by ELISA analysis on days 1-4. Specific productivity is calculated, normalized to the control on the respective day and is shown for day 3 (white bar) and day 4 (black bar). As a negative control a non targeting siRNA (siLacZ-FITC) and as a positive control, a siRNA targeting the IgG1 antibody (siLC-104) are used (n=4, error bars=SEM).

FIG. 3: TRANSIENT EXPRESSION OF MICRORNAS IN BIBH1-PRODUCING CHO CELLS

CHO-DG44 cells stably secreting an IgG1 antibody (BIBH1) are transfected with each of the 20 validated miRNA hits (see FIG. 1B) in quadruplicates. Cell density and viability are determined by cell counting and trypane blue exclusion. Antibody concentrations in the supernatant are detected on days 1-4 by ELISA analysis. Specific productivity is calculated, normalized to the control on the respective day and is shown for day 3 (white bar) and day 4 (black bar). As a negative control a non targeting siRNA (siLacZ-FITC) and as a positive control a siRNA targeting the IgG1 antibody (siLC-104) are used (n=1, error bars=SEM of quadruplicates).

FIG. 4: TRANSIENT EXPRESSION OF MICRORNAS IN HSA-PRODUCING CELLS

CHO-DG44 cells stably secreting human serum albumin (HSA) are transfected with each of the 20 validated miRNA hits (see FIG. 1B) in quadruplicates. Cell density, viability and antibody concentrations in the supernatant are detected on day 1-4 by cell counting and trypane blue exclusion or ELISA analysis, respectively. Specific productivity is calculated, normalized to the control on the respective day and is shown for day 3 (white bar) and day 4 (black bar). As a negative control a non targeting siRNA (siLacZ-FITC) and as a positive control a siRNA targeting human serum albumin (siHSA) are used (n=2, error bars=SEM).

Figure 5:
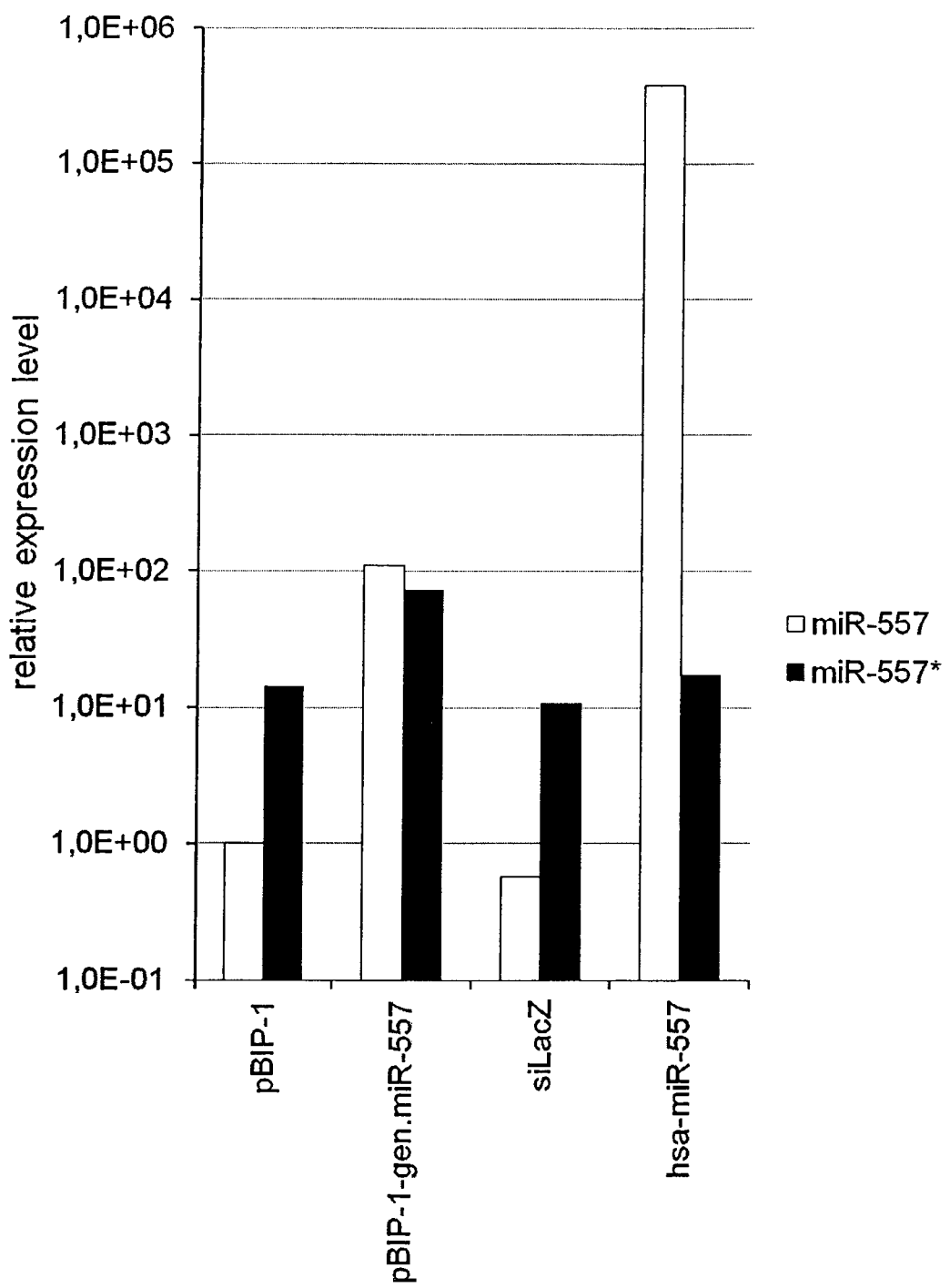

FIG. 5: QUANTIFICATION OF MICRORNA EXPRESSION IN BIWA4-PRODUCING CHO CELLS BY QPCR qPCR analysis of expression levels of microRNA miR-557 in CHO-DG44-derived producer cells after transient transfection with either a human microRNA-encoding plasmid or the mature microRNA. The white bars correspond to the sense strand of miR-557, the black bars correspond to the anti-sense strand (miR-557"). Relative expression is calculated and plotted in comparison to control samples (empty vector and siLacZ-transfected cells, respectively).

FIG. 6: EFFECT OF MICRORNA COMBINATIONS ON IGG PRODUCTION

CHO-DG44 cells stably secreting an IgG1 (BIWA4) are transiently transfected with a combination of two validated miRNA hits (every possible combination of these five miRNAs: hsa-miR-557, hsa-miR-1271, hsa-miR-1275, hsa-miR-1287 and hsa-miR-1978) in duplicates. Samples containing a single microRNA are adjusted to a final RNA concentration of 1 μM by adding mimic miRNA negative control. Cell density and antibody concentration in the supernatant are determined on day 1-4 by cell counting or trypane blue exclusion and ELISA analysis, respectively, and specific productivity is calculated. Shown are the specific productivities at day 4 after transfection. Transfection efficiency is monitored by flow cytometry of siLacZ-FITC transfected cells and ELISA analysis of the supernatant of siLC-104 (targeting the light chain of the antibody) transfected cells. As negative controls a non targeting siRNA (siLacZ-FITC) and a mimic miRNA are used (error bars=SEM of duplicates).

FIG. 7: TRANSIENT EXPRESSION OF MICRORNAS IN INSULIN-SECRETING INS1 CELLS

The rat cell line INS-1, which endogenously secrets insulin, is transiently transfected by nucleofection with 5 screen hit miRNAs. Insulin assay is performed with basal conditions and insulin secretion is induced using 20 mM glucose. The insulin concentration in the supernatant is determined by ELISA analysis. Cell density is measured by crystal violet staining and insulin concentrations are normalized to the cell density. Shown are the results of basal (white bar) and induced (black bar) samples. As negative control a non targeting siRNA (siLacZ) is used (n=1, error bars=SEM of duplicates).

FIG. 8: TRANSIENT EXPRESSION OF MICRORNAS IN HEK293 FLPIN

HEK293 FlpIN cells stably expressing a secretable form of HRP (ssHRP-flag) are transfected by lipofection with 5 miRNAs (hsa-miR-1287, hsa-miR-183, hsa-miR-557, hsa-miR-612 and hsa-miR-644). Two days after transfection ssHRP-flag expression is induced by doxycyclin and the activity of secreted HRP is measured the next day. Medium is changed and HRP activity in the supernatant is assessed by luminescence measurement after 5 hours. The results are normalized to miRNA neg. control. Shown are the relative luminescence units normalized for cell density (n=4, error bars SEM).

Figure 9:
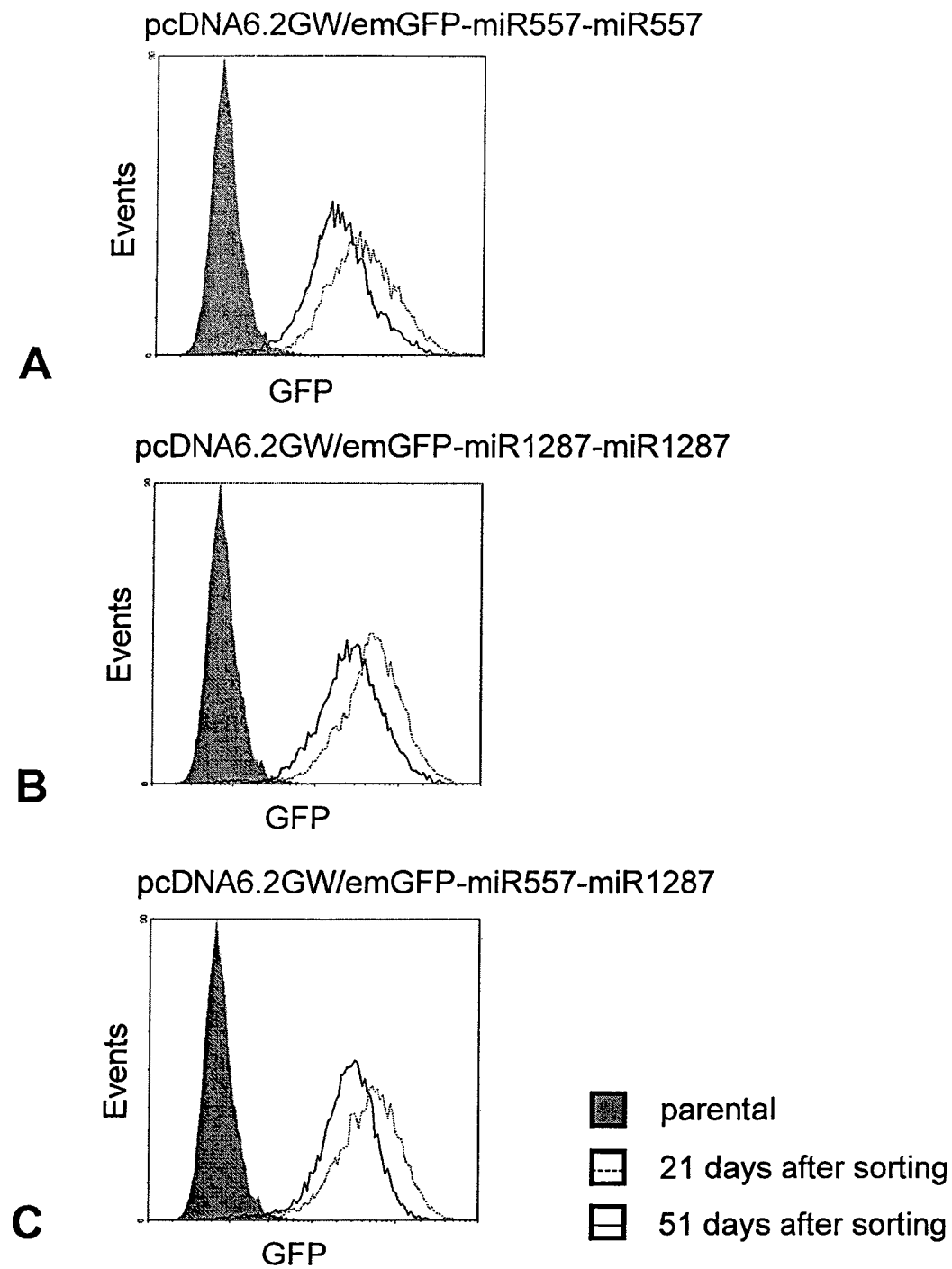

FIG. 9: QUANTIFICATION OF STABLE MICRORNA OVEREXPRESSION IN BIWA4-PRODUCING CHO CELLS BY FLOW CYTOMETRY

CHO-DG44 cells stably secreting an IgG1 (BIWA4) were stably transfected with a GFP-containing expression vector further encoding (A) hsa-miR-557 (pcDNA6.2-GW/emGFP-miR557-miR557), (B) hsa-miR-1287 (pcDNA6.2-GW/emGFP-miR1287-miR1287), and (C) both miRNAs (hsa-miR-557 and hsa-miR-1287; pcDNA6.2-GW/emGFP-miR557-miR1287). GFP-positive cells were enriched by FACS and living cells were analyzed by flow cytometry analysis after cultivation for the indicated times (21 days, dotted line; 51 days, solid line) after sorting. As a negative control, untransfected cells (grey filled peak) without GFP expression were used.

Figure 10:
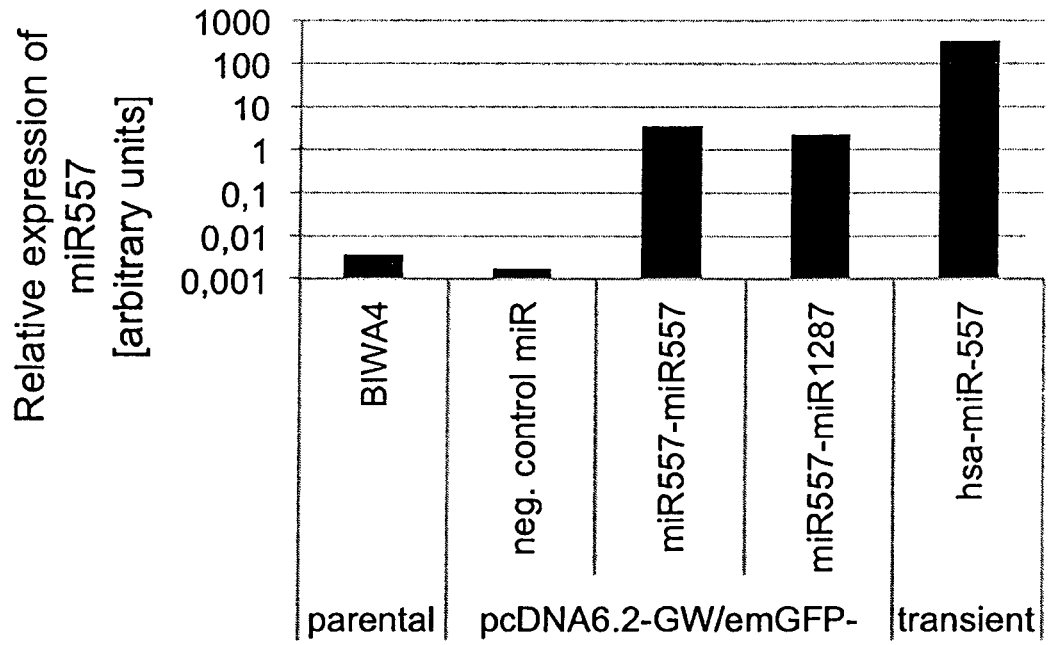
Figure 10:
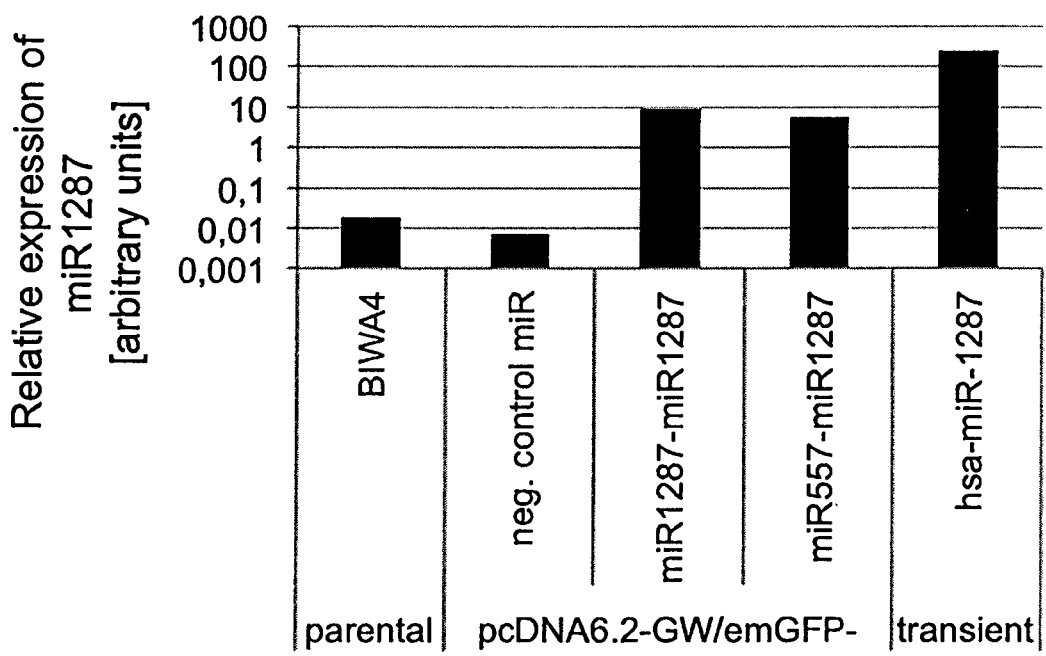

FIG. 10: QUANTIFICATION OF STABLE MICRORNA OVEREXPRESSION IN BIWA4-PRODUCING CHO CELLS BY QPCR

CHO-DG44 cells stably secreting an IgG1 (BIWA4) were stably transfected with an expression vector encoding either hsa-miR-557 (pcDNA6.2-GW/emGFP-miR557-miR557) or hsa-miR-1287 (pcDNA6.2-GW/emGFP-miR1287-miR1287) or encoding for both miRNAs (hsa-miR-557 and hsa-miR-1287) in combination (pcDNA6.2-GW/emGFP-miR557-miR1287). GFP-positive cells were enriched by FACS and RNA was extracted to measure levels of the mature hsa-miR-557 (top panel) or hsa-miR-1287 (bottom panel) microRNA by qPCR analysis. Cells transfected with the mature miRNA (hsa-miR-557 or hsa-miR1287) served as a positive control. For the positive control, RNA was extracted one day after transient transfection. Relative expression was calculated by normalizing to the reference RNU6B.

FIG. 11: STABLE EXPRESSION OF MICRORNA COMBINATIONS IN BIWA4-PRODUCING CHO CELLS

CHO-DG44 cells stably secreting an IgG1 (BIWA4) were stably transfected with a combination of two validated miRNA hits (pcDNA6.2-GW/emGFP-miR557-miR1287) or a negative control miRNA expression plasmid (pcDNA6.2-GW/emGFP-neg. control-miRNA) and enriched for GFP positive cells by FACS. Stable pools (3 independent pools for the miRNA combination miR557-miR1287 and 4 independent pools for the neg. control miRNA) were grown in fed-batch cultures. Cell density and antibody concentration in the supernatant were determined on day 3-7 by cell counting with trypane blue exclusion and ELISA analysis, respectively, and specific productivity was calculated. A representative experiment is shown and the data correspond to the mean of the independent pools for product concentration (BIWA4) (top panel), specific productivity (middle panel) and viable cell density (bottom panel). Error bars represent SEM. The experiment was repeated three times. The parental cell line (CHO-DG44 secreting BIWA4) served as an additional control.

Figure 12:
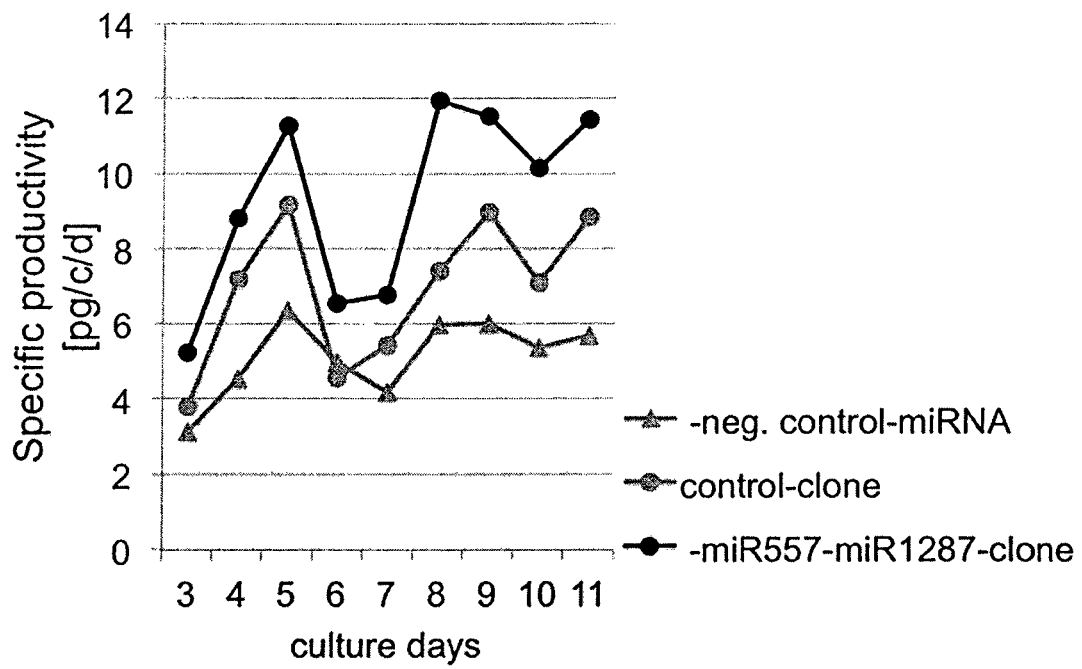
Figure 12:
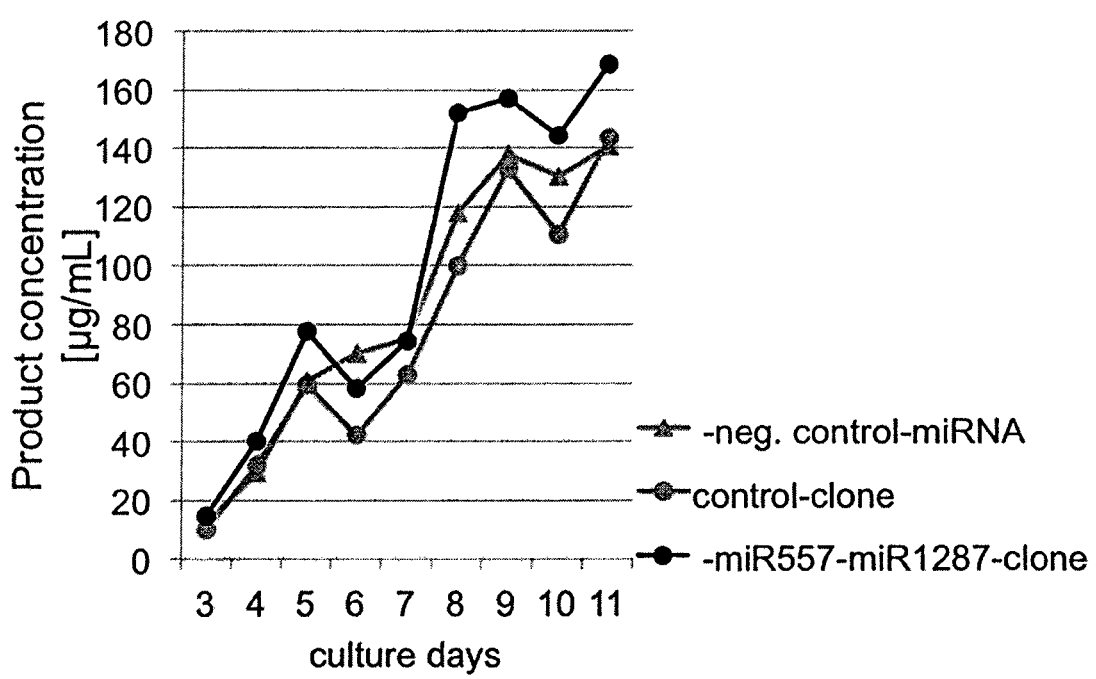

FIG. 12: SINGLE CLONE OF BIWA4-PRODUCING CHO CELLS STABLY EXPRESSING A MICRORNA COMBINATION

CHO-DG44 stably secreting an IgG1 (BIWA4) were stably transfected with miRNA expression vectors (pcDNA6.2-GW/emGFP) and single clones were generated by limited dilution. Either a combination of 2 validated miRNA hits (-miR557-miR1287-clone) or the respective empty vector control expressing GFP (-control-clone) were used during fed-batch cultures. Three independent pools stably expressing a neg. control miRNA (pcDNA6.2-GW/emGFP-neg. control-miRNA) served as further controls. Cell density and antibody concentration in the supernatant were determined on day 3-11 by cell counting with trypane blue exclusion and ELISA analysis, respectively, and specific productivity was calculated. Shown is the specific productivity (top panel) and product concentration (bottom panel) of the single clone expressing the miR557-miR1287 combination compared to the control clone and the mean of the three independent pools (neg. control-miRNA).

Figure 13A:
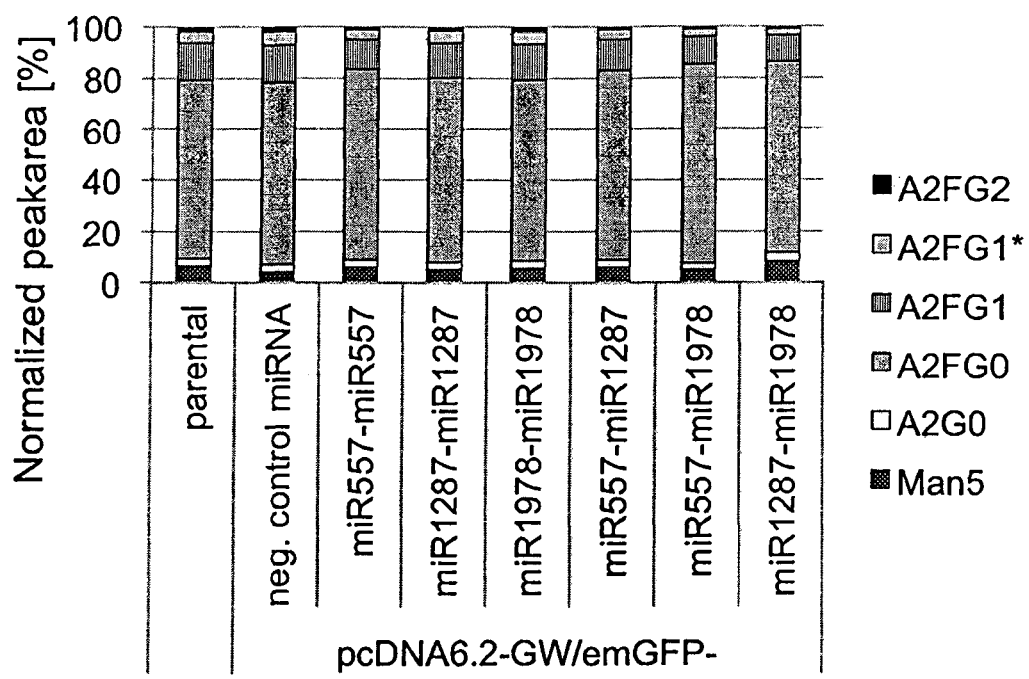

FIG. 13A: GLYCOSYLATION ANALYSIS OF BIWA4 ANTIBODY PRODUCED IN CHO CELLS STABLY EXPRESSING MICRORNAS OR MICRORNA COMBINATIONS

CHO-DG44 cells stably secreting an IgG1 (BIWA4) were stably transfected with miRNA expression plasmids encoding for miRNAs or miRNA combinations (hsa-miR557, hsa-miR1287, hsa-miR1978, and their combinations). The composition of the Fc-glycosylation of the IgG (BIWA4) produced in these cell lines was analysed. The glycans were first released from the purified antibody by enzymatic digestion with PNGase F. Glycans were purified, labelled with a fluorescent dye and separated by microchip-based CGE. The percentages of the glyco-forms present were calculated from the chromatographic peak areas shown in FIG. 13B and indicated by arrows. Abbreviations, A2, biantennary; G, galactose; F, fucose; Man, mannose.

Figure 13B:
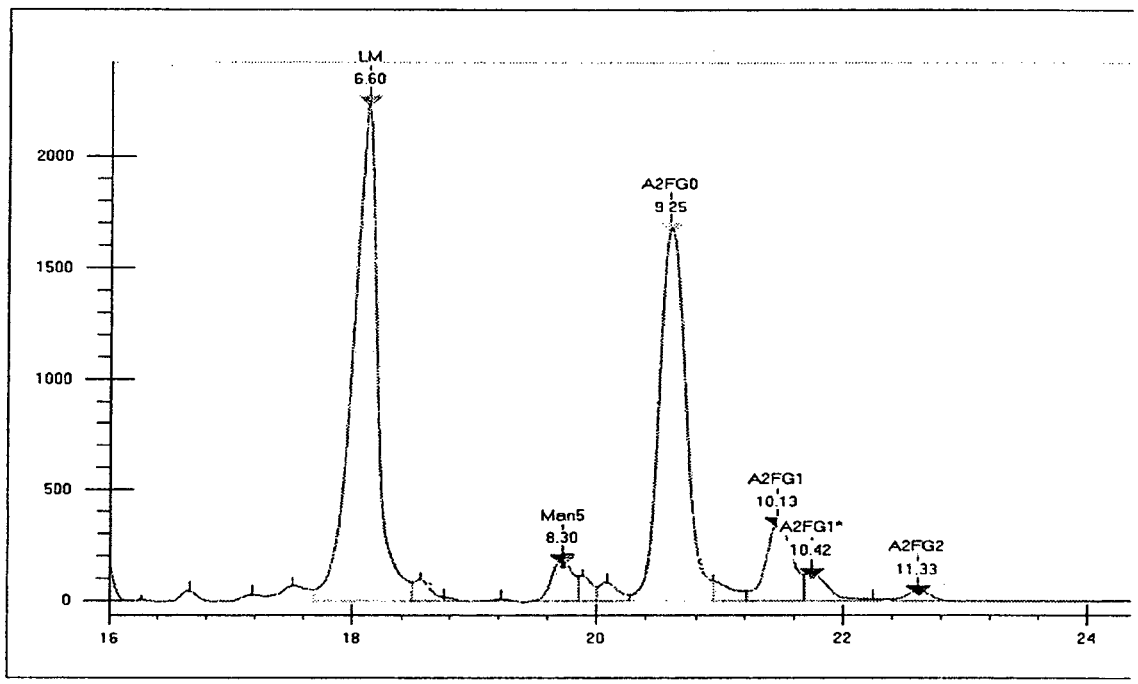
Figure 13B:
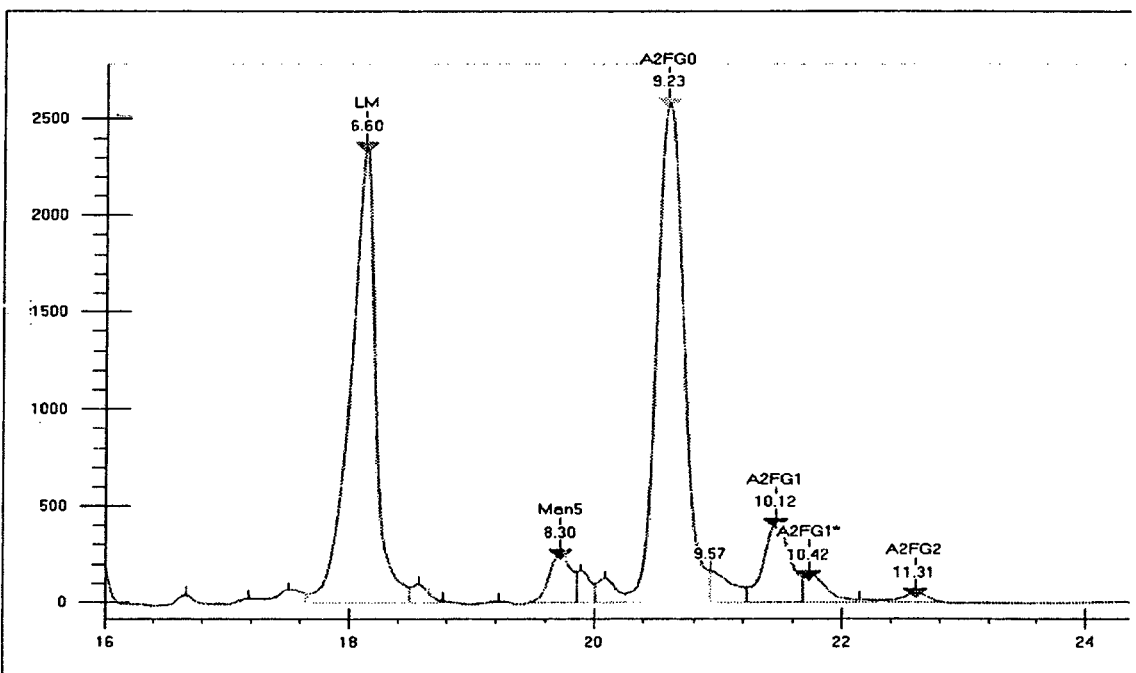
Figure 13B:
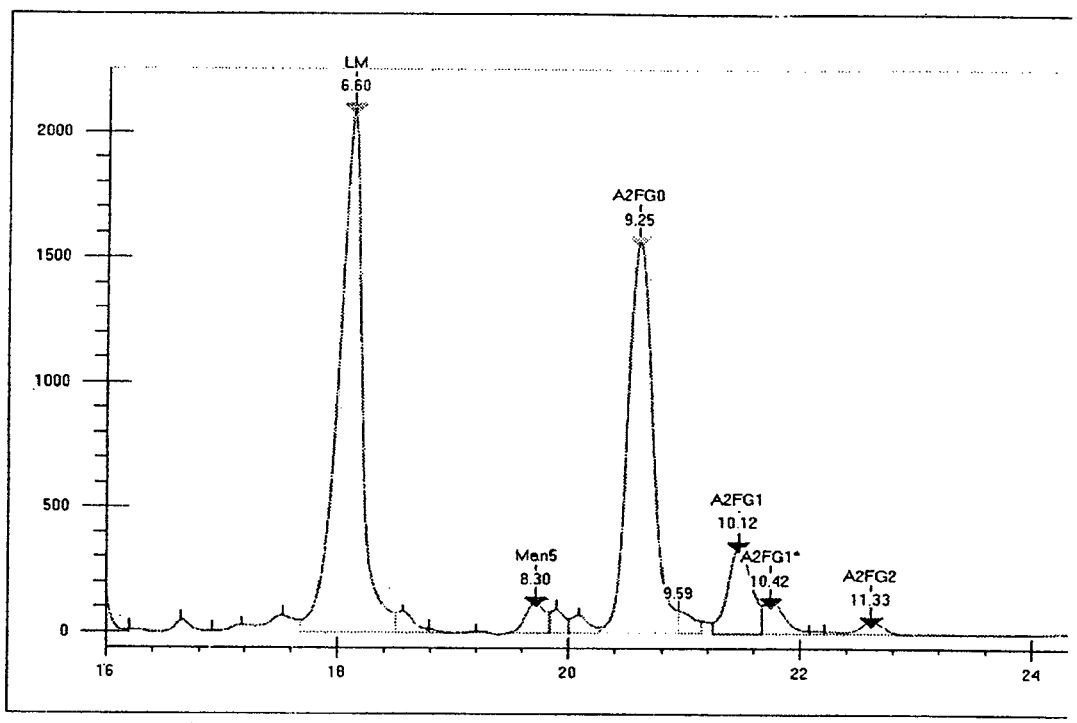
Figure 13B:
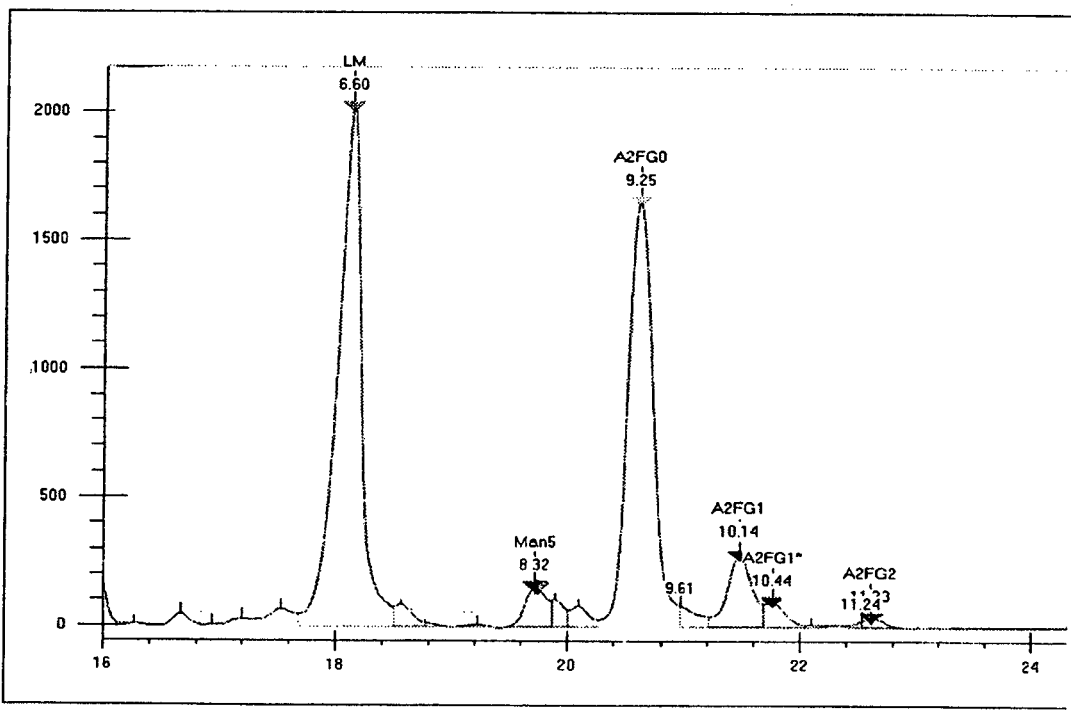
Figure 13B:
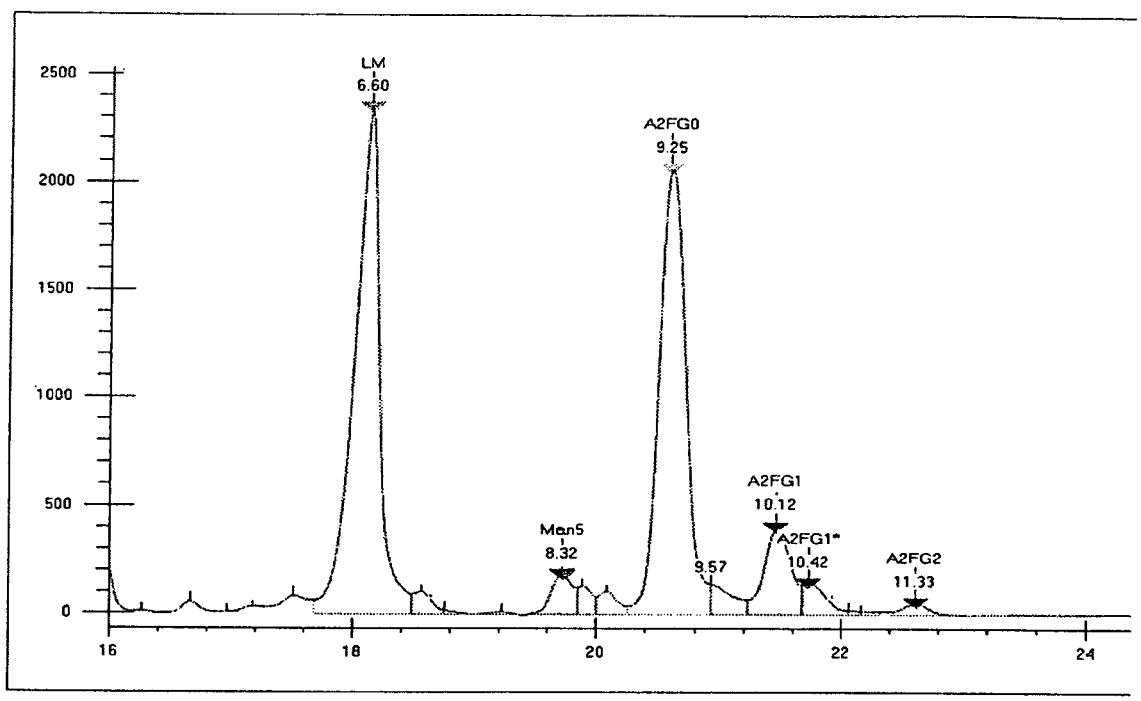
Figure 13B:
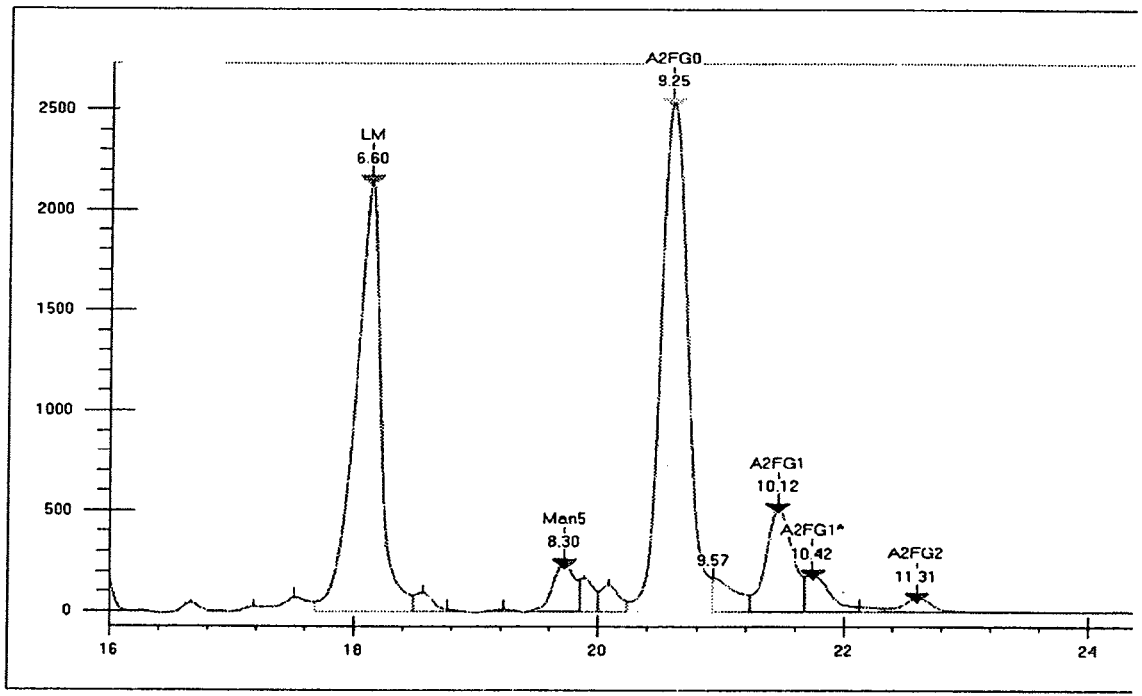
Figure 13B:
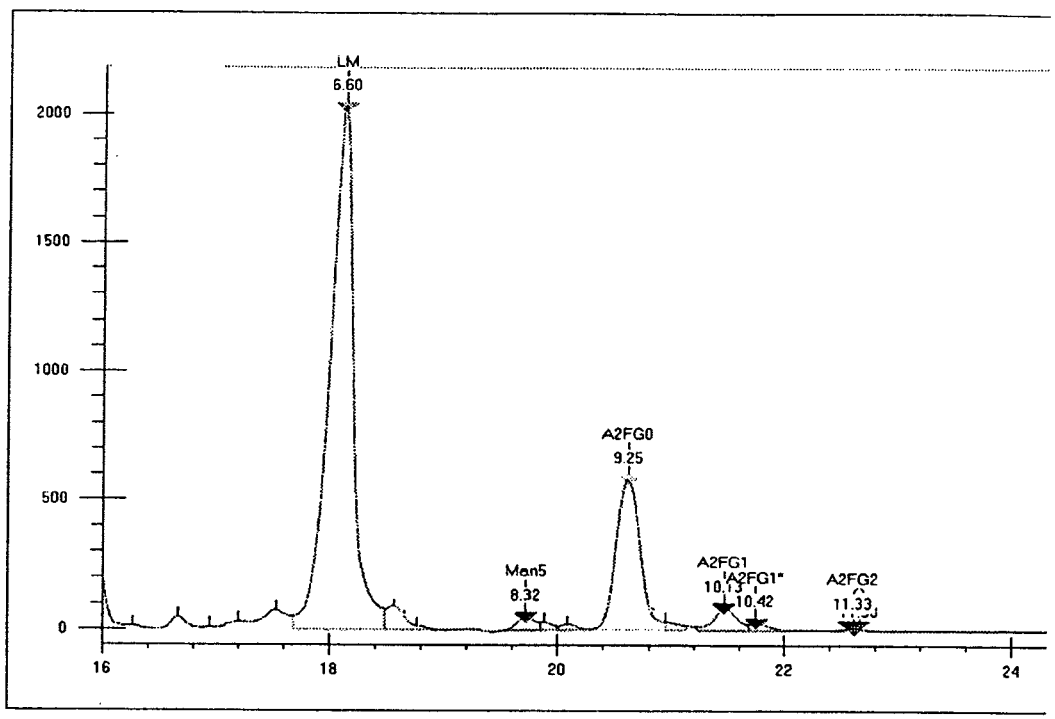
Figure 13B:
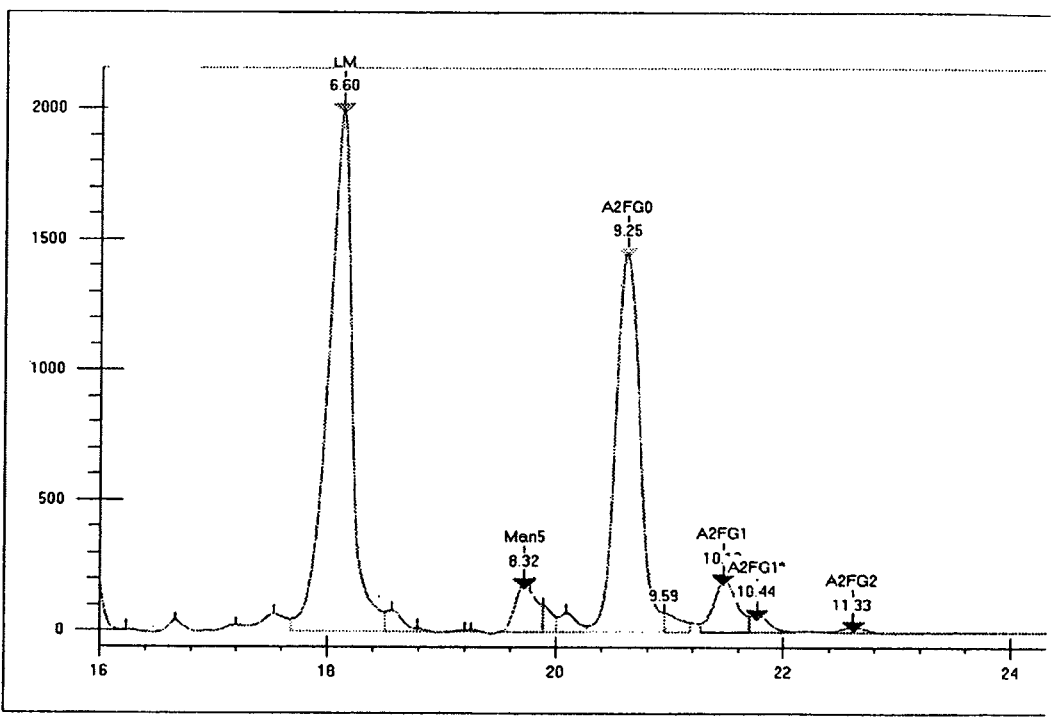

FIG. 13B: CHROMATOGRAPHIC PEAK AREAS FROM GLYCOSYLATION ANALYSIS OF BIWA4 ANTIBODY PRODUCED IN CHO CELLS STABLY EXPRESSING MICRORNAS OR MICRORNA COMBINATIONS.

FIG. 14: TRANSIENT EXPRESSION OF MICRORNAS IN HELA CELLS

HeLa cells were transiently transfected with different miRNAs (hsa-miR-125a-3p, hsa-miR-1978 and hsa-miR557) followed by ssHRP-FLAG transfection two days later. The next day, the medium was changed and the activity of secreted HRP in the supernatant was measured after 4 h (white bars) and 6 h (black bars) by luminescence measurement. The results were normalized to miRNA neg. control and are shown as relative luminescence units (RLU) (top panel) (n=4, error bars SEM). Furthermore, endogenous IL-8 secretion was measured two days after transient miRNA (hsa-miR-125a-3p, hsamiR-1271, hsa-miR-185*, hsa-miR-193b*, hsa-miR-1978, hsa-miR-299-3p and hsa-miR557) transfection. Medium was changed and collected after 6 h (white bars) and 24 h (black bars). Supernatants were analysed by ELISA and results were normalized to mi RNA neg. control samples (bottom panel) (n=3, error bars SEM). Cells transfected without RNA (mock) or untransfected cells as shown served as additional controls.

DETAILED DESCRIPTION OF THE INVENTION

CHO cells are commonly used for the production of therapeutic proteins. Genetic engineering approaches have attempted to optimize the productivity of these cells by expressing specific cDNAs. Naturally existing non-coding RNAs regulate cell fate by modulating the expression of a whole set of target proteins, which may possibly result in a super-secretory phenotype when over-expressed in CHO producer cells. To exploit the power of non-coding RNAs and to identify those that positively affect secretion of a heterologous therapeutic protein, CHO-DG44 cells stably expressing a protein, for example a Fc-containing protein, such as an antibody, are transiently transfected by nucleofection with a human microRNA mimic library consisting of 879 microRNAs. microRNAs that (i) increased the IgG1 titer in the supernatant more than 1.3-fold on day 3 or 4 compared to control cells in one experiment and (ii) increased the mean IgG1 titer on day 3 or 4 of more than 1.4-fold in two experiments are provided by the present invention. Given that the host cell already produces high amounts of heterologous protein, a further increase in productivity of >30% is highly significant and surprising.

The (micro)RNAs of the present invention specifically enhance the expression and secretion of immunoglobulin molecules as well as of other recombinant proteins, e.g. therapeutic proteins such as human serum albumin (HSA). Surprisingly, the (micro)RNAs of the present invention also exert a positive effect on the specific productivity of HSA-secreting CHO cells on days 3 and 4 post transfection. Thus, the present invention provides 20 (micro) RNAs that surprisingly function in a product-independent manner.

Remarkably, the combined transfection of two different miRNAs provided herein enhanced specific productivity on day 4 compared to singly transfected CHO-DG44 cells in some cases. For example, co-transfection of miR-557 and miR-1287 clearly had a positive effect in increasing the productivity compared to both microRNAs alone. Thus, with certain combinations of microRNAs, it is possible to achieve an additive or even synergistic effect on the enhancement of secretory capacity of a cell producing a protein of interest, preferably a therapeutic protein, which can result in enhanced specific productivity, enhanced product titer or both. Preferred combinations of different RNAs are miR-557 (SEQ ID NO:16) and miR-1287 (SEQ ID NO:6), miR-557 (SEQ ID NO:16) and miR-1978 (SEQ ID NO:11), miRNA-1271 (SEQ ID NO: 3) and miR-1978 (SEQ ID NO:11) or miR-1287 (SEQ ID NO: 6) and miRNA-1978 (SEQ ID NO:11), more preferably miR-557 (SEQ ID NO:16) and miR-1287 (SEQ ID NO:6).

Figure 7:
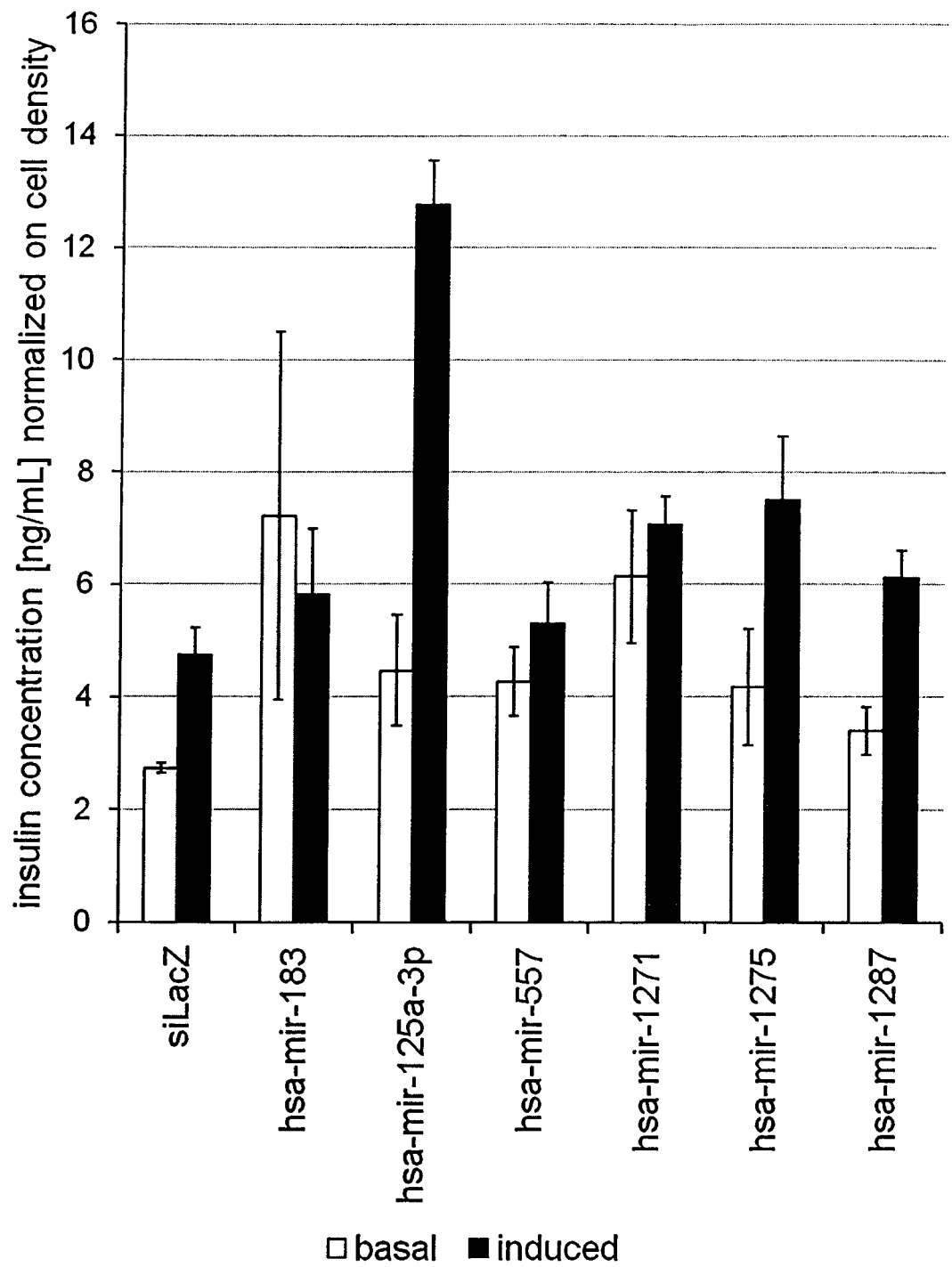
Figure 8:
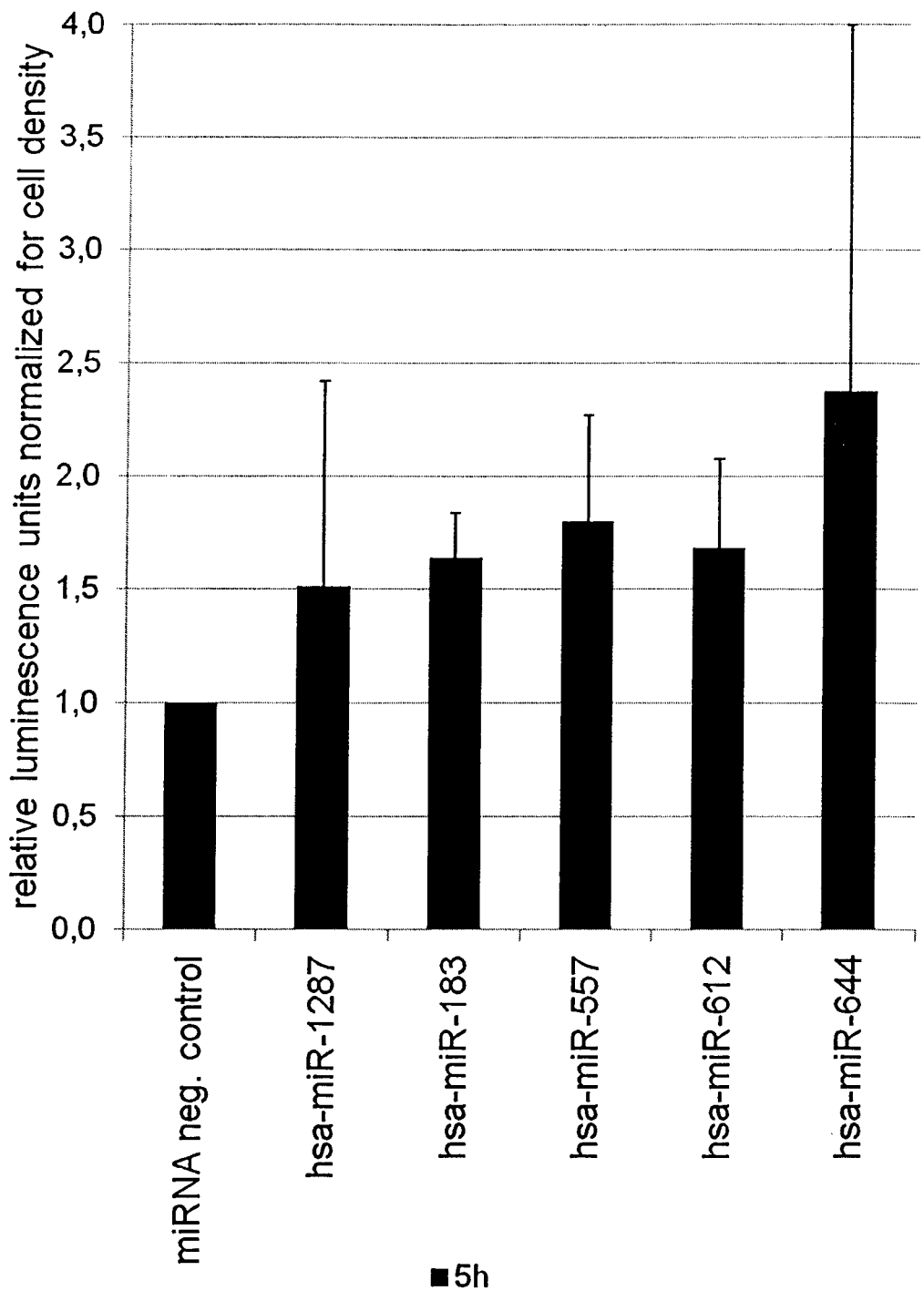

Surprisingly, the microRNAs provided herein (e.g., hsa-miR-183, hsa-miR-125-3p, hsa-miR-557, hsa-miR-1271, hsa-miR-1275, hsa-miR-1287) also exert a positive effect on basal and glucose-stimulated insulin secretion of rat cells (such as INS1 cells, see FIG. 7). Several of them also led to enhanced secretion from human cells (HEK293, see e.g. FIG. 8). Thus, unexpectedly the microRNAs of the present invention positively affect the secretion of endogenous proteins not only in CHO, but also in other cells of rodent origin such as rat and in cells of human origin and hence function in a species- and product-independent manner.

The present invention further shows that stable transfectants can be generated. Thus, the present invention further relates to mammalian cells stably expressing the RNAs of the invention and methods of developing such cells. Those stably transfected miRNA transgene host cells may be subjected to batch or fed-batch fermentations. In each of these settings, overexpression of the non-coding RNAs of the invention (e.g., miR-577 and miR-1287, hsa-miR-183, hsa-miR-125-3p, hsa-miR-1271, hsa-miR-1275 or miR-1978) lead to increased protein production and/or secretion, for example to increased antibody production and/or secretion. The non-coding RNAs of the present invention are able to enhance the specific production capacity of the cells grown in serial cultures or in bioreactor batch or fed batch cultures.

In one embodiment, the present invention provides a cell comprising (i) a plasmid encoding one chain of an antibody and containing a DHFR cassette for amplification, (ii) a plasmid encoding the other chain of an antibody and containing a neomycin resistance cassette, and (iii) a plasmid encoding a microRNA of the present invention, preferably miR-577 and miR-1287, hsa-miR-183, hsa-miR-125-3p, hsa-miR-1271, hsa-miR-1275 or miRNA-1978 (see Table 1B) and containing a puromycin resistance cassette. The overexpression of the non-coding RNAs of the present invention leads to increased antibody titers, indicating that the non-coding RNAs of the present invention are able to enhance the specific production capacity of the cells, especially of those grown in serial cultures or in bioreactor batch or fed batch cultures.

To explore whether transient expression of the 20 microRNAs according to the invention also enhances the secretion of IgG4 molecules, CHO cells stably expressing IgG4 are transiently transfected with each of the 20 microRNAs as described in example 2 and their specific productivity is determined. All 20 microRNAs exert a positive effect on the specific productivity of IgG4-secreting CHO cells on days 3 and/or 4 post transfection. Thus the microRNAs of the present invention function in a product-independent manner.

Furthermore, the miRNAs of the invention do not affect glycosylation of the protein of interest. Glycosylation of recombinant proteins can have a profound impact on the half-life, activity and immunogenicity of the biotherapeutic protein drug. As the exact mechanism of action for the microRNAs used in the present invention is currently not or only incompletely understood, the effect of those microRNAs used for cell engineering on protein glycosylation was analysed and was found to have no unexpected negative side-effect on the glycosylation of the protein of interest. Thus the microRNAs provided herein do not affect glycosylation of the protein of interest, such as in the Fc-domain of an antibody.

The production cells derived from microRNA engineered host cells show higher secretion rates, i.e. productivities and/or higher titers (see e.g., example 11). Hence, microRNA engineering can be done after, prior to or simultaneously to introducing the protein of interest with similar results, thus offering a broad range of options for applications in pharmaceutical development processes.

Furthermore, for some microRNAs, sufficiently high stable levels of microRNA in the host cell or the producer cell can only be achieved after introducing a gene amplification step. Thus, in another embodiment the miRNAs of the present invention is amplified. Amplification can be performed by placing the microRNA expression cassette under the control of an amplifiable genetic selection marker, such as dihydrofolate reductase (DHFR), glutamine synthetase (GS) or else. The amplifiable selection marker gene can be on the same expression vector as the miRNA expression cassette. Alternatively, the amplifiable selection marker gene and the miRNA expression cassette can be on different expression vectors, but integrate in close proximity into the host cell's genome. Two or more vectors that are co-transfected simultaneously, for example, often integrate in close proximity into the host cell's genome. Amplification of the genetic region containing the microRNA expression cassette is then mediated by adding the amplification agent (e.g., MTX for DHFR or MSX for GS) into the cultivation medium. In cases where the expression constructs of the protein of interest also contain an amplifiable selection marker, it is possible and preferred to use the identical amplifiable marker gene for both, microRNA and gene of interest to allow for co-amplification. However, independent amplification of the microRNA gene is also possible. Sufficiently high stable levels of microRNA in the host cell or the producer cell may also be achieved, e.g., by cloning multiple copies of the microRNA encoding polynucleotide into an expression vector. Cloning multiple copies of the microRNA encoding polynucleotide into an expression vector and amplifying the miRNA expression cassette as described above may further be combined.

Furthermore, growth and viability profiles of the microRNA engineered cells of the invention are comparable or only slightly lower compared to controls. However, the specific productivity of microRNA engineered cells is consistently higher compared to non-engineered cell lines (see e.g. examples 12, 15 and 16). This results in an overall benefit of the microRNA engineering approach according to the invention for industrial therapeutic protein production processes.

Definitions

The general embodiments "comprising" or "comprised" encompass the more specific embodiment "consisting of". Furthermore, singular and plural forms are not used in a limiting way.

As used herein, the singular forms "a", "an" and "the" designate both the singular and the plural, unless expressly stated to designate the singular only.

Terms used in the course of the present invention have the following meaning.

The term "ribonucleic acid" or "RNA" describes a molecule consisting of a sequence of nucleotides, which are built of a nucleobase, a ribose sugar, and a phosphate group. RNAs are usually single stranded molecules and can exert various functions. The term ribonucleic acid specifically comprises small non-coding RNA such as microRNA. The specific RNAs claimed in the present invention are listed in FIG. 1B with miroRNA number (following the nomination assigned by Dharmacon) and MIMAT number and may also be referred to as non-coding RNA or microRNA of the invention. Further examples of ribonucleic acids are tRNA and hRNA.

The terms "microRNA" or "miRNA" are used interchangeably herein. microRNAs are small, about 22 nucleotide-long (typically between 19 and 25 nucleotides in length) non-coding RNAs. microRNAs are encoded in the genome of eukaryotic cells and are typically transcribed by RNA Polymerase III as long primary transcripts that are then processed in several steps first into ~70nt-long hairpin-loop structures and subsequently into the ~22nt RNA duplex. The active mature strand is then loaded into the RNA-induced silencing complex (RISC) in order to block translation of target proteins or degradation of their respective mRNAs. The specific microRNAs claimed in the present invention are listed in FIG. 1B with microRNA number (following the nomination assigned by Dharmacon) and MIMAT number and were taken from the human microRNA library obtained from Dharmacon (CS-001010 mimic microRNA library; lot number 09167). The term "microRNA" as used herein therefore relates to endogenous human miRNAs, but also encompasses other sequences identified from said library. The prefix "hsa" indicates the human origin of a microRNA, but may be omitted in the context of the present invention. The sequences provided herein as SEQ ID NOs: 1 to 20 represent the sequence of the mature miRNA.

tRNAs or 'transfer RNAs' are 73 to 93 nucleotide long RNA molecules with a defined secondary structure which function as adaptors between a codon on the mRNA and its encoded amino acid thus playing a fundamental role in protein synthesis.

The term "derivative" as used in the present invention means a polypeptide molecule or a nucleic acid molecule, which is at least 70% identical in sequence with the original sequence or its complementary sequence. Preferably, the polypeptide molecule or nucleic acid molecule is at least 80% identical in sequence with the original sequence or its complementary sequence. More preferably, the polypeptide molecule or nucleic acid molecule is at least 90% identical in sequence with the original sequence or its complementary sequence. Most preferred is a polypeptide molecule or a nucleic acid molecule, which is at least 95% identical in sequence with the original sequence or its complementary sequence and displays the same or a similar effect on secretion as the original sequence.

Sequence differences may be based on differences in homologous sequences from different organisms. They might also be based on targeted modification of sequences by substitution, insertion or deletion of one or more nucleotides or amino acids, preferably 1, 2, 3, 4, 5, 7, 8, 9 or 10. Deletion, insertion or substitution mutants may be generated using site-specific mutagenesis and/or PCR-based mutagenesis techniques.

"Host cells" in the meaning of the present invention are eukaryotic cells, preferably mammalian cells, most preferably rodent cells such as hamster cells. Preferred cells are BHK21, BHK TK⁻, CHO, CHO-K1, CHO-DUKX, CHO-DUKX B1, and CHO-DG44 cells or the derivatives/progenies of any of such cell line. Particularly preferred are CHO-DG44, CHO-DUKX, CHO-K1 and BHK21, and even more preferred are CHO-DG44 and CHO-DUKX cells. Most preferred are CHO-DG44 cells. In a specific embodiment of the present invention the host cells are murine myeloma cells, preferably NSO and Sp2/0 cells or the derivatives/progenies of any of such cell line. Non-limiting examples of mammalian cells which can be used in the meaning of this invention are also summarized in Table 1. However, derivatives/progenies of those cells, other mammalian cells, including but not limited to human, mice, rat, monkey, and rodent cell lines, can also be used in the present invention, particularly for the production of biopharmaceutical proteins. Even other eukaryotic cells, including but not limited to yeast, insect and plant cells, can also be used in the methods and uses as described herein.

TABLE 1

Eukaryotic production cell lines

| CELL LINE | ORDER NUMBER |
|---|---|
| NS0 | ECACC No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 (BHK-21 derivative) | ATCC CRL-8544 |
| CHO | ECACC No. 8505302 |
| CHO wild type | ECACC 00102307 |
| CHO-K1 | ATCC CCL-61 |
| CHO-DUKX (= CHO duk⁻, CHO/dhfr⁻) | ATCC CRL-9096 |
| CHO-DUKX B11 | ATCC CRL-9010 |
| CHO-DG44 | (Urlaub et al., 1983) |
| CHO Pro-5 | ATCC CRL-1781 |
| V79 | ATCC CCC-93 |
| B14AF28-G3 | ATCC CCL-14 |
| HEK 293 | ATCC CRL-1573 |
| COS-7 | ATCC CRL-1651 |
| U266 | ATCC TIB-196 |
| HuNS1 | ATCC CRL-8644 |
| CHL | ECACC No. 87111906 |
| CAP[1] | Wolfel et al.(2011) |
| PER.C6 ® | Pau et al. (2001)/Crucell |
| H4-II-E | ATCC CRL-1548 |
|  | ECACC No. 87031301 |
|  | Reuber (1961), Pitot (1964) |
| H4-II-E-C3 | ATCC CRL-1600 |
| H4TG | ATCC CRL-1578 |
| H4-II-E | DSM ACC3129 |
| H4-II-Es | DSM ACC3130 |

[1]CAP (CEVEC's Amniocyte Production) cells are an immortalized cell line based on primary human amniocytes. They were generated by transfection of these primary cells with a vector containing the functions E1 and pIX of adenovirus 5. CAP cells allow for competitive stable production of recombinant proteins with excellent biologic activity and therapeutic efficacy as a result of authentic human posttranslational modification.

Host cells are most preferred, when being established, adapted, and completely cultivated under serum free conditions, and optionally in media, which are free of any protein/peptide of animal origin. Commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-Invtirogen), serum-free CHO Medium (Sigma), and protein-free CHO Medium (Sigma) are exemplary appropriate nutrient solutions. Any of the media may be supplemented as necessary with a variety of compounds, non-limiting examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics and trace elements. Any other necessary supplements may also be included at appropriate concentrations that would be known to those skilled in the art. In the present invention the use of serum-free medium is preferred, but media supplemented with a suitable amount of serum can also be used for the cultivation of host cells. For the growth and selection of genetically modified cells expressing the selectable gene a suitable selection agent is added to the culture medium.

The term "protein" is used interchangeably with "amino acid residue sequences" or "polypeptide" and refers to polymers of amino acids of any length. These terms also include proteins that are post-translationally modified through reactions that include, but are not limited to, glycosylation, acetylation, phosphorylation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with the same properties.

The term "polypeptide" means a sequence with more than 10 amino acids and the term "peptide" means sequences with up to 10 amino acids in length. However, the terms might be used interchangeably.

The present invention is suitable to generate host cells for the production of biopharmaceutical polypeptides/proteins. The invention is particularly suitable for the high-yield expression of a large number of different genes of interest by cells showing enhanced cell productivity.

"Gene of interest" (GOI), "selected sequence", "gene that encodes a product/protein of interest" or "product gene" have the same meaning herein and refer to a polynucleotide sequence of any length that encodes a product of interest or "protein of interest", also mentioned by the term "desired product". The selected sequence can be full length or a truncated gene, a fusion or tagged gene, and can be a cDNA, a genomic DNA, or a DNA fragment, preferably, a cDNA. It can be the native sequence, i.e. naturally occurring form(s), or can be mutated or otherwise modified as desired. These modifications include codon optimizations to optimize codon usage in the selected host cell, humanization, fusion or tagging. The selected sequence can encode a secreted, cytoplasmic, nuclear, membrane bound or cell surface polypeptide.

The "protein of interest" or "desired protein" includes proteins, polypeptides, fragments thereof, peptides, all of which can be expressed in the selected host cell. Proteins of interest are preferably therapeutic proteins. Proteins of interest can be for example antibodies, enzymes, cytokines, lymphokines, adhesion molecules, receptors and derivatives or fragments thereof, and any other polypeptides that can serve as agonists or antagonists and/or have therapeutic or diagnostic use. Examples for a desired protein/polypeptide are also given below. In the case of more complex molecules such as monoclonal antibodies, the GOI encodes one or both of the two antibody chains. The term "producing" or "highly producing", "production", "production and/or secretion", "producing" or "production cell" as used herein relates to the production of the protein or product of interest. An "increased production and/or secretion" relates to the expression of the protein of interest or the product of interest and means an increase in specific productivity, increased titer or both. Preferably the specific productivity and the titre are increased. Increased titer as used herein relates to an increased concentration in the same volume, i.e., an increase in total yield. The produced protein of interest may be, for example, a secreted, cytoplasmic, nuclear, membrane bound, or a cell surface polypeptide, preferably, the protein of interest is a secreted protein.

The term "antibody" refers to a protein consisting of one or more polypeptides substantially encoded by immunoglobulin genes. The recognized immunoglobulin genes include the kappa, lambda, alpha, gamma, delta, epsilon and mu constant regions genes as well as the myriad immunoglobulin variable region genes. As used herein, the term "antibody" includes a polyclonal, monoclonal, bi-specific, multi-specific, human, humanized, or chimeric antibody. The terms "antibody" and "immunoglobulin" are used interchangeably and are used to denote, without being limited thereto, glycoproteins having the structural characteristics noted above for immunoglobulins.

The term "antibody" is used herein in its broadest sense and specifically covers single monoclonal antibodies (including agonist and antagonist antibodies) and antibody compositions with polyepitopic specificity. The term "antibody" specifically covers monoclonal antibodies (including full length monoclonal antibodies), polyclonal antibodies, multispecific antibodies (e.g. bispecific antibodies) and antibody fragments (such as Fv, Fab, Fab', F(ab)2 or other antigen-binding subsequences of antibodies). Preferably, they contain or are modified to contain at least the portion of the CH2 domain of the heavy chain immunoglobulin constant region comprising the N-linked glycosylation site. Exemplary antibodies within the scope of the present invention include but are not limited to anti-CD20, anti-CD33, anti-CD37, anti-CD40, anti-CD44, anti-CD52, anti-HER2/neu (erbB2), anti-EGFR, anti-IGF, anti-VEGF, anti-TNFalpha, anti-IL2 or anti-IgE antibodies.

The term "monoclonal antibody" (mAb) as used herein refers to an antibody obtained from a population of substantially homogeneous antibodies based on the amino acid sequence. Monoclonal antibodies are highly specific, being directed against a single antigenic site. Furthermore, in contrast to conventional (polyclonal) antibody preparations, which typically include different antibodies directed against different determinants (epitopes), each mAb is directed against a single determinant on the antigen. In addition to their specificity, the mAbs are advantageous in that they can be synthesized by cell culture (hybridomas, recombinant cells or the like) uncontaminated by other immunoglobulins. The mAbs herein include chimeric, humanized and human antibodies.

"Chimeric antibodies" are antibodies, wherein light and/or heavy chain genes have been constructed, typically by genetic engineering, from immunoglobulin variable and constant regions of different species, such as mouse and human. Or alternatively, whose heavy chain genes are belonging to a particular antibody class or subclass while the remainder of the chain is from another antibody class or subclass of the same or another species. Also covered are fragments of such antibodies, preferably fragments that contain or are modified to contain at least one CH2 domain. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant or effector domain from a human antibody (e.g. ATCC Accession No. CRL 9688 secretes an anti-Tac chimeric antibody), although other mammalian species may be used.

The term "humanized antibodies" according to the present invention refers to specific chimeric antibodies, immunoglobulin chains or fragments thereof (such as Fv, Fab, Fab', F(ab)2 or other antigen-binding subsequences of antibodies), which contain minimal sequence derived from non-human immunoglobulin. Preferably they contain or are modified to contain at least the portion of the CH2 domain of the heavy chain immunoglobulin constant region comprising the N-linked glycosylation site. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by the corresponding non-human residues. Furthermore, humanized antibodies can comprise residues which are found neither in the recipient antibody nor in the imported CDR or framework sequences. These modifications are made to further refine and maximize antibody performance. In general, the humanized antibody will comprise at least one, and typically two, variable domains, in which all or substantially all off the CDR regions correspond to those of a non-human immunoglobulin and all or substantially all of the framework regions are those of a human immunoglobulin consensus sequence. Preferably, the humanized antibody also comprises at least a portion of an immunoglobulin constant region, typically that of a human immunoglobulin.

Humanized antibody: comprising a human framework region and one or more CDRs from a non-human (usually a mouse or rat) antibody. Adjustments in framework amino acids might be required to keep antigen binding specificity, affinity and or structure of domain.

The term "CH2 domain" according to the present invention is meant to describe the CH2 domain of the heavy chain immunoglobulin constant region comprising the N-linked glycosylation site. In defining an immunoglobulin CH2 domain reference is made to immunoglobulins in general and in particular to the domain structure of immunoglobulins as applied to human IgG1 by Kabat, E. A. (Kabat, 1988; Kabat et al., 1991). Accordingly, immunoglobulins are generally heterotetrameric glycoproteins of about 150 kDa, composed of two identical light and two identical heavy chains. Each light chain is linked to a heavy chain by one covalent disulfide bond, while the number of disulfide linkages varies between the heavy chains of different immunoglobulins isotypes. Each heavy and light chain also has regularly spaced intrachain disulfide bridges. Each heavy chain has an amino terminal variable domain (VH) followed by carboxy terminal constant domains (CH). Each light chain has a variable N-terminal domain (VL) and a C-terminal constant domain (CL).

Depending on the amino acid sequence of the constant domain of the heavy chains, antibodies can be assigned to different classes. There are five major classes: IgA, IgD, IgE, IgG and IgM. The heavy chain constant domains that correspond to the different classes of antibodies are called alpha, delta, epsilon, gamma and mu domains, respectively. The mu chain of IgM contains five domains (VH, CHmu1, CHmu2, CHmu3 and CHmu4). The heavy chain of IgE also contains five domains while the heavy chain of IgA has four domains. The immunoglobulin class can be further divided into subclasses (isotypes), e.g. IgG1, IgG2, IgG3, IgG4, IgA1 and IgA2.

The subunit structures and three-dimensional configuration of different classes of immunoglobulins are well known. Of these IgA and IgM are polymeric and each subunit contains two light and two heavy chains. The heavy chain of IgG contains a polypeptide chain lying between the CHgamma1 and CHgamma2 domains known as the hinge region. The alpha chain of IgA has a hinge region containing an O-linked glycosylation site. The mu and epsilon chains do not have a sequence analogous to the hinge region of the gamma and alpha chains, however, they contain a fourth constant domain lacking in the other in the other immunoglobulin classes.

A "CH2 domain" therefore is an immunoglobulin heavy chain constant region domain. The Fc region of a full antibody usually comprises two CH2 domains and two CH3 domains. According to the present invention, the CH2 domain is preferably the CH2 domain of one of the five immunoglobulin classes indicated above. Preferred are mammalian immunoglobulin CH2 domains such as primate or murine immunoglobulin with the primate and especially human immunoglobulin CH2 domains being preferred. The amino acid sequences of immunoglobulin CH2 domains are known or are generally available to the skilled artisan (Kabat et al., 1991). A preferred immunoglobulin CH2 domain within the context of the present invention is a human IgG and preferably from IgG1, IgG2, IgG3, IgG4, more preferably a human IgG1 and IgG3 and even more preferred a human IgG1. Using the numbering system of Edelman (Edelman et al., 1969), the immunoglobulin CH2 domain preferably begins at amino acid position equivalent to glutamine 233 of human IgG1 and extends through amino acid equivalent to lysine 340 (Ellison and Hood, 1982).

With respect to human antibody molecules reference is made to the IgG class in which an N-linked oligosaccharide is attached to the amide side chain of Asn 297 of the beta-4 bend to the inner face of the CH2 domain of the Fc region. Preferably, the antibody or Fc-fusion protein contains or is modified to contain at least a CH2 domain. The CH2 domain is a CH2 domain of an immunoglobulin having a single N-linked oligosaccharide of a human IgG CH2 domain. The CH2 domain is preferably the CH2 domain of human IgG1.

The term "Proteins of interest", "products of interest" or "desired proteins" as used herein include, but are not limited to antibodies and Fc-fusion proteins, all of which can be expressed in the host cells of the invention. Furthermore, desired proteins or proteins of interest can be for example enzymes, cytokines, lymphokines, adhesion molecules, receptors and derivatives or fragments thereof, and any other polypeptides and scaffolds that can serve as agonists or antagonists and/or have therapeutic or diagnostic use. The "product of interest" may also be an antisense RNA.

Especially, desired proteins/polypeptides or proteins of interest are for example, but not limited to insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL; G-CSF, GM-CSF, M-CSF, MCP-1, VEGF, and single domain antibodies (camelid derived antibodies). Also included is the production of erythropoietin or any other hormone growth factors and any other polypeptides that can serve as agonists or antagonists and/or have therapeutic or diagnostic use.

A preferred protein of interest is an antibody or a fragment or derivative thereof. Thus, the invention can be advantageously used for production of antibodies such as monoclonal, polyclonal, multispecific antibodies, or fragments thereof which comprise a CH2 domain, Fc and Fc'-fragments, heavy and light immunoglobulin chains and/or their constant fragments. Furthermore, the method for producing a (recombinant) protein according to the invention can be advantageously used for production of antibodies such as monoclonal, polyclonal, multispecific antibodies, or fragments thereof which comprise a CH2 domain, Fc and Fc'-fragments, heavy and light immunoglobulin chains and/or their constant fragments as well as Fc-fusion proteins.

"Fc-fusion proteins" are defined as proteins which contain or are modified to contain at least the portion of the CH2 domain of the heavy chain immunoglobulin constant region comprising the single N-linked glycosylation site. According to the Kabat EU nomenclature (Kabat et al., 1991) this N-linked glycosylation site is at position Asn297 in an IgG1, IgG2, IgG3 or IgG4 antibody.

The other part of the fusion protein can be the complete sequence or any part of the sequence of a natural or modified heterologous protein or a composition of complete sequences or any part of the sequence of a natural or modified heterologous protein. The immunoglobulin constant domain sequences may be obtained from any immunoglobulin subtypes, such as IgG1, IgG2, IgG3, IgG4, IgA1 or IgA2 subtypes or classes such as IgA, IgE, IgD or IgM. Preferentially they are derived from human immunoglobulin, more preferred from human IgG and even more preferred from human IgG1 and IgG3. Non-limiting examples of Fc-fusion proteins are MCP1-Fc, ICAM-Fc, EPO-Fc and scFv fragments or the like coupled to the CH2 domain of the heavy chain immunoglobulin constant region comprising the N-linked glycosylation site. Fc-fusion proteins can be constructed by genetic engineering approaches by introducing the CH2 domain of the heavy chain immunoglobulin constant region comprising the N-linked glycosylation site into another expression construct comprising for example other immunoglobulin domains, enzymatically active protein portions, or effector domains. Thus, an Fc-fusion protein according to the present invention comprises also a single chain Fv fragment linked to the CH2 domain of the heavy chain immunoglobulin constant region comprising e.g. the N-linked glycosylation site.

Furthermore, antibody fragments include e.g. "Fab fragments" (Fragment antigen-binding=Fab). Fab fragments consist of the variable regions of both chains, which are held together by the adjacent constant region. These may be formed by protease digestion, e.g. with papain, from conventional antibodies, but similar Fab fragments may also be produced by genetic engineering. Further antibody fragments include F(ab')2 fragments, which may be prepared by proteolytic cleavage with pepsin. Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilised. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins are known to the person skilled in the art.

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucin-zipper domains. However, there are also strategies in which the interaction between the VH/VL regions of the scFv are used for the multimerisation (e.g. dia-, tri- and pentabodies). By diabody the skilled person means a bivalent homodimeric scFv derivative. The shortening of the Linker in a scFv molecule to 5-10 amino acids leads to the formation of homodimers in which an inter-chain VH/VL-superimposition takes place. Diabodies may additionally be stabilised by the incorporation of disulphide bridges. Examples of diabody-antibody proteins are known to the person skilled in the art.

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a Linker region. Examples of minibody-antibody proteins are known to the person skilled in the art.

By triabody the skilled person means a trivalent homotrimeric scFv derivative. In said scFv derivatives the VH-VL domains are fused directly without a linker sequence, which leads to the formation of trimers.

By "scaffold proteins" the skilled person means any functional domain of a protein that is coupled by genetic cloning or by co-translational processes with another protein or part of a protein that has another function.

The skilled person will also be familiar with so-called miniantibodies which have a bi-, tri- or tetravalent structure and are derived from scFv. The multimerisation is carried out by di-, tri- or tetrameric coiled coil structures.

The protein of interest, especially the antibody, antibody fragment or Fc-fusion protein, is preferably recovered/isolated from the culture medium as a secreted polypeptide, or it can be recovered/isolated from host cell lysates if expressed without a secretory signal. It is necessary to purify the protein of interest from other recombinant proteins and host cell proteins to obtain substantially homogenous preparations of the protein of interest. As a first step, cells and/or particulate cell debris are removed from the culture medium or lysate. Further, the product of interest is purified from contaminant soluble proteins, polypeptides and nucleic acids, for example, by fractionation on immunoaffinity or ion-exchange columns, ethanol precipitation, reverse phase HPLC, Sephadex chromatography, and chromatography on silica or on a cation exchange resin such as DEAE. Methods for purifying a heterologous protein expressed by host cells are known in the art.

By definition any sequences or genes introduced into a host cell are called "heterologous sequences", "heterologous genes", "heterologous RNAs" or "transgenes" or "recombinant gene" with respect to the host cell, even if the introduced sequence, RNA or gene is identical to an endogenous sequence, RNA or gene in the host cell. A "heterologous" or "recombinant" protein or RNA is thus a protein or RNA expressed from a heterologous sequence or gene. In a preferred embodiment, the introduced sequence, RNA or gene is not identical to an endogenous sequence, RNA or gene of the host cell in question, although embodiments where it is identical are also contemplated in connection with the present invention.

The term "recombinant" is used interchangeably with the term "heterologous" throughout the specification of this present invention, especially in the context with protein and RNA expression. Thus, a "recombinant" protein is a protein expressed from a heterologous sequence.

"Heterologous gene sequences" or "heterologous sequences" can be introduced into a target cell by using an "expression vector", preferably a eukaryotic, and even more preferably a mammalian expression vector. Methods used to construct vectors are well known to the person skilled in the art and described in various publications. In particular techniques for constructing suitable vectors, including a description of the functional components such as promoters, enhancers, termination and polyadenylation signals, selection markers, origins of replication, and splicing signals, are reviewed in considerable details in (Sambrook et al., 1989) and references cited therein. Vectors may include but are not limited to plasmid vectors, phagemids, cosmids, articificial/mini-chromosomes (e.g. ACE), or viral vectors such as baculovirus, retrovirus, adenovirus, adeno-associated virus, herpes simplex virus, retroviruses and bacteriophages. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operably linked, are well known in the art and some are commercially available from companies such as Stratagene, La Jolla, Calif.; Invitrogen, Carlsbad, Calif.; Promega, Madison, Wis. or BD Biosciences Clontech, Palo Alto, Calif. Usually expression vectors also comprise an expression cassette encoding a selectable marker, allowing selection of host cells carrying said expression marker.

In the present invention the expression vectors are also used for introducing "heterologous sequences" or "polynucleotide sequences" encoding RNAs, preferably non-coding RNAs, more preferably miRNAs, into a host cell. Such expression vectors may comprise genomic microRNA sequences for transient or stable expression of miRNAs in cells, specifically in mammalian cells, even more specifically in CHO cells. Preferably, said expression vector is a mammalian expression vector. Means for cloning genomic microRNA into an expression vector are known to the person skilled in the art. They include, but are not limited to cloning genomic microRNA sequences with approximately 300 bp flanking regions into a mammalian expression vector, such as pBIP-1, operably linked to a promoter, preferably a strong promoter, such as a CMV promoter or any other strong promoter known to work in the host cell.

Alternatively, one or more microRNAs may be cloned as polynucleotides encoding engineered pre-miRNA sequences (i.e. short hairpins) into a mammalian expression vector, such as pcDNA6.2-GW/miR or pcDNA6.2-GW/EmGFP-miR from Invitrogen (see manual BLOCK-iT™ Pol II miR RNAi Expression Vector Kits). Said vector may encode one or more copies of the same or different miRNAs. In brief, the mature miRNA sequence is cloned into a given sequence encoding an optimized hairpin loop sequence and 3' and 5' flanking regions derived from the murine miRNA mir-155 (Lagos-Quintana et al., 2002). The flanking regions are present on the vector and a DNA oligonucleotide is designed, which encodes the miRNA sequence, the mentioned loop and the antisense sequence of the respective mature miRNA with a two nucleotide depletion to generate a internal loop in the hairpin stem. Furthermore, overhangs are added for cloning at both ends. Hairpin structure may be analyzed using the online tool mfold (M. Zuker. Mfold web server for nucleic acid folding and hybridization prediction. Nucleic Acids Res. 31 (13), 3406-3415, 2003). DNA strands are annealed and ligated into the 3'-UTR of emerald GFP reporter protein gene as described by the manufacturer. A vector containing more than one miRNA may be generated applying the chaining method. The negative control miRNA (supplied by the manufacturer) and the siLacZ may be used as appropriate negative controls. Alternative vectors that may be used in the present invention for miRNA expression, without being limited thereto, are pCMV-MIR (Origene), pmR-ZsGreen1 (clontech) and shMIMIC lentiviral miRNA vector (ThermoScientific).

In a preferred embodiment the expression vector comprises at least one nucleic acid sequence, which is a regulatory sequence necessary for transcription and translation of nucleotide sequences that encode a peptide/polypeptide/protein of interest or necessary for transcription of nucleotide sequences that encode a RNA, preferably a non-coding RNA, more preferably a miRNA.

The term "expression" as used herein refers to transcription and/or translation of a heterologous nucleic acid sequence within a host cell. The level of expression of a desired product/protein of interest in a host cell may be determined on the basis of either the amount of corresponding mRNA that is present in the cell, or the amount of the desired polypeptide/protein of interest encoded by the selected sequence as in the present examples. For example, mRNA transcribed from a selected sequence can be quantified by Northern blot hybridization, ribonuclease RNA protection, in situ hybridization to cellular RNA or by PCR. Proteins encoded by a selected sequence can be quantitated by various methods, e.g. by ELISA, by Western blotting, by radioimmunoassays, by immunoprecipitation, by assaying for the biological activity of the protein, by immunostaining of the protein followed by FACS analysis or by homogeneous time-resolved fluorescence (HTRF) assays. The level of expression of a non-coding RNA, such as a miRNA can be quantified by PCR, such as qPCR.

"Transfection" as used in the present invention relates to the introduction of genetic material, into a mammalian host cell, wherein the mammalian host cell may be transiently transfected or stably transfected. The genetic material may be an expression vector comprising a gene of interest or a polynucleotide sequence encoding a non-coding RNA, such as a miRNA. Alternatively, mature miRNAs may be transiently transfected into a host cell. Typically, miRNAs are transfected as double stranded RNAs. It is also possible to transfect an antisense strand RNA, which is chemically modified to prevent RISC loading or to transfect a hairpin RNA.

Transfection of eukaryotic host cells with a polynucleotide or expression vector, resulting in genetically modified cells or transgenic cells, can be performed by any method known in the art (see e.g. (Sambrook et al., 1989)). Transfection methods include, but are not limited to liposome-mediated transfection, calcium phosphate co-precipitation, electroporation, nucleofection, nucleoporation, microporation, polycation (such as DEAE-dextran)-mediated transfection, protoplast fusion, viral infections and microinjection. Preferably, the transfection is a stable transfection. The transfection method that provides optimal transfection frequency and expression of the heterologous genes in the particular host cell line and type is favoured. Suitable methods can be determined by routine procedures. For stable transfectants the constructs are either integrated into the host cell's genome or an artificial chromosome/minichromosome or located episomally so as to be stably maintained within the host cell. Thus, the stably transfected sequences actually remain in the genome of the cell and its daughter cells. Typically, this involves the use of a selectable marker gene and the gene of interest or the polynucleotide sequence encoding the RNA is integrated together with the selectable marker gene. In some cases the entire expression vector integrates into the cell's genome, in other cases only parts of the expression vector integrate into the cell's genome. Cells "stably expressing" a protein of interest or a RNA are stably transfected with a gene of interest encoding said protein of interest or with a polynucleotide sequence encoding said RNA. Thus, the sequences encoding the protein of interest or RNA remain in the genome of the cell and its daughter cells. However, "stably expressing a protein of interest" also includes an endogenous protein, if the protein of interest is endogenous to the cell (e.g., insulin secretion by INS-1 cells).

A "selectable marker gene" or "selection marker gene" is a gene which encodes a selectable marker and allows the specific selection of cells which contain this gene, typically by the addition of a corresponding "selecting agent" to the cultivation medium. As an illustration, an antibiotic resistance gene may be used as a positive selectable marker. Only cells which have been transformed with this gene are able to grow in the presence of the corresponding antibiotic and are thus selected. Untransformed cells, on the other hand, are unable to grow or survive under these selection conditions. There are positive, negative and bifunctional selectable markers. Positive selectable markers permit the selection and hence enrichment of transformed cells by conferring resistance to the selecting agent or by compensating for a metabolic or catabolic defect in the host cell. By contrast, cells which have received the gene for the selectable marker can be selectively eliminated by negative selectable markers. An example of this is the thymidine kinase gene of the Herpes Simplex virus, the expression of which in cells with the simultaneous addition of acyclovir or gancyclovir leads to the elimination thereof. The selectable marker genes useful in this invention also include the amplifiable selectable markers. The literature describes a large number of selectable marker genes including bifunctional (positive/negative) markers (see for example WO 92/08796 and WO 94/28143). Examples of selectable markers which are useful in the present invention include, but are not limited to the genes of aminoglycoside phosphotransferase (APH), hygromycine phosphostransferase (HYG), dihydrofolate reductase (DHFR), thymidine kinase (TK), glutamine synthetase, asparagin synthetase and genes which confer resistance to neomycin (G418/Geneticin), puromycin, histidinol D, bleomycin, phleomycin, blasticidin and zeocin. Also included are genetically modified mutants and variants, fragments, functional equivalents, derivatives, homologues and fusions with other proteins or peptides, provided that the selectable marker retains its selective qualities. Such derivatives display considerable homology in the amino acid sequence in the regions or domains, which are deemed to be selective.

Selection may also be made by fluorescence activated cell sorting (FACS) using for example a cell surface marker, bacterial 8-galactosidase or fluorescent proteins (e.g. green fluorescent proteins (GFP) and their variants from *Aequorea victoria* and *Renilla reniformis* or other species; red fluorescent proteins, fluorescent proteins and their variants from non-bioluminescent species (e.g. *Discosoma* sp., *Anemonia* sp., *Clavularia* sp., *Zoanthus* sp.) to select for recombinant cells.

The term "selection agent" or "selective agent" refers to a substance that interferes with the growth or survival of a cell, unless a certain selectable marker gene product is present in the cell which alleviates the effect of the selection agent. For example, to select for the presence of an antibiotic resistance gene like APH (aminoglycoside phosphotransferase) in a transfected cell the antibiotic Geneticin (G418) is used.

The term "modified neomycin-phosphotransferase (NPT)" covers all the mutants described in WO2004/050884, particularly the mutant D227G (Asp227Gly), which is characterised by the substitution of aspartic acid (Asp, D) for glycine (Gly, G) at amino acid position 227 and particularly preferably the mutant F240I (Phe240Ile), which is characterised by the substitution of phenylalanine (Phe, F) for isoleucine (Ile, I) at amino acid position 240.

The "amplifiable selectable marker gene" usually codes for an enzyme, which is needed for the growth of eukaryotic cells under certain cultivation conditions. For example, the amplifiable selectable marker gene may code for dihydrofolate reductase (DHFR) or glutamine synthetase (GS). In this case the gene is amplified, if a host cell transfected therewith is cultivated in the presence of the selecting agent methotrexate (MTX) or methionine sulphoximine (MSX), respectively. Sequences linked to the amplifiable selectable marker gene (i.e., sequences physically proximal thereto) are co-amplified together with the amplifiable selectable marker gene. Said co-amplified sequences may be introduced on the same expression vector or on separate vectors.

The following Table 2 gives non-limiting examples of amplifiable selectable marker genes and the associated selecting agents, which may be used according to the invention. Suitable amplifiable selectable marker genes are also described in an overview by Kaufman (Kaufman, 1990).

TABLE 2

Amplifiable selectable marker genes

| Amplifiable selectable marker gene | Accession number | Selecting agent |
|---|---|---|
| dihydrofolate reductase (DHFR) | M19869 (hamster) E00236 (mouse) | methotrexate (MTX) |
| metallothionein | D10551 (hamster) M13003 (human) M11794 (rat) | cadmium |
| CAD (carbamoylphosphate synthetase:aspartate transcarbamylase: dihydroorotase) | M23652 (hamster) D78586 (human) | N-phosphoacetyl-L-aspartate |
| adenosine-deaminase | K02567 (human) M10319 (mouse) | Xyl-A- or adenosine, 2'deoxycoformycin |
| AMP (adenylate)-deaminase | D12775 (human) J02811 (rat) | adenine, azaserin, coformycin |
| UMP-synthase | J03626 (human) | 6-azauridine, pyrazofuran |
| IMP 5'-dehydrogenase | J04209 (hamster) J04208 (human) M33934 (mouse) | mycophenolic acid |
| xanthine-guanine-phosphoribosyltransferase | X00221 (E. coli) | mycophenolic acid with limiting xanthine |
| mutant HGPRTase or mutant thymidine-kinase | J00060 (hamster) M13542, K02581 (human) J00423, M68489 (mouse) M63983 (rat) M36160 (Herpes virus) | hypoxanthine, aminopterine and thymidine (HAT) |
| thymidylate-synthetase | D00596 (human) M13019 (mouse) L12138 (rat) | 5-fluorodeoxyuridine |
| P-glycoprotein 170 (MDR1) | AF016535 (human) J03398 (mouse) | several drugs, e.g. adriamycin, vincristin, colchicine |
| ribonucleotide reductase | M124223, K02927 (mouse) | aphidicoline |
| glutamine-synthetase (GS) | AF150961 (hamster) U09114, M60803 (mouse) M29579 (rat) | methionine sulphoximine (MSX) |
| asparagine-synthetase | M27838 (hamster) M27396 (human) U38940 (mouse) U07202 (rat) | β-aspartylhydroxamate, albizziin, 5'azacytidine |
| argininosuccinate-synthetase | X01630 (human) M31690 (mouse) M26198 (bovine) | canavanin |
| ornithine-decarboxylase | M34158 (human) J03733 (mouse) M16982 (rat) | α-difluoromethylornithine |
| HMG-CoA-reductase | L00183, M12705 (hamster) M11058 (human) | compactin |
| N-acetylglucosaminyl-transferase | M55621 (human) | tunicamycin |
| threonyl-tRNA-synthetase | M63180 (human) | borrelidin |
| Na$^+$K$^+$-ATPase | J05096 (human) M14511 (rat) | ouabain |

According to the invention a preferred amplifiable selectable marker gene is a gene which codes for a polypeptide with the function of GS or DHFR.

The term "transformation" or "to transform", "transfection" or "to transfect" as used herein means any introduction of a nucleic acid sequence into a cell, resulting in genetically modified, recombinant, transformed or transgenic cells. The introduction can be performed by any method known in the art. Methods include but are not limited to lipofection, electroporation, polycation (such as DEAE-dextran)-mediated transfection, protoplast fusion, viral infections and microinjection or may be carried out by means of the calcium method, electroshock method, intravenous/intramuscular injection, aerosol inhalation or an oocyte injection. The transformation may result in a transient or stable transformation of the host cells. The term "transfection" or "to transfect", "transformation" or "to transform" also means the introduction of a viral nucleic acid sequence in a way which is for the respective virus the naturally one. The viral nucleic acid sequence needs not to be present as a naked nucleic acid sequence but may be packaged in a viral protein envelope. Thus, the term relates not only to the method which is usually known under the term "transfection" or "to transfect", "transformation" or "to transform". Transfection methods that provide optimal transfection frequency and expression of the introduced nucleic acid are favoured. Suitable methods can be determined by routine procedures. For stable transfectants the constructs are either integrated into the host cell's genome or an artificial chromosome/mini-chromosome or located episomally so as to be stably maintained within the host cell.

The term "microRNA engineered cells" or "microRNA engineered host cells" or "cells engineered to exhibit increased levels of microRNAs" as used herein relates to mammalian cells, such as CHO cells, transfected with any one of the RNAs, preferably non-coding RNAs, more preferably miRNAs of the invention or an expression vector encoding any one of the RNAs, preferably non-coding RNAs, more preferably miRNAs of the invention as shown in Table 1B. Further encompassed are combination of two or more RNAs, preferably non-coding RNAs, more preferably miRNAs of the invention as shown in Table 1B, wherein the two or more miRNAs may be the same or different. Preferably, the mammalian cells are stably transfected with an expression vector encoding at least one miRNA of the invention. Such cells may also be referred to as stably microRNA engineered host cells.

Embodiments

In a first aspect, the invention concerns a ribonucleic acid (RNA) selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20, wherein said RNA leads to an increase in the production and/or secretion of a protein of interest from a eukaryotic cell, preferably from a mammalian cell. Preferably said RNA is a small non-coding RNA such as a micro ribonucleic acid (miRNA). More preferably said RNA is a miRNA. In one embodiment the invention concerns a micro ribonucleic acid (miRNA) selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20, wherein said miRNA leads to an increase in the production and/or secretion of a therapeutic protein of interest from a mammalian cell.

The RNAs may lead to an increase in the production and/or secretion of a protein of interest in a species-independent manner. Non-limiting examples thereof are miR-125a-3p (SEQ ID NO: 1), miR-1271 (SEQ ID NO: 3), miR-1275 (SEQ ID NO: 4), miR-183 (SEQ ID NO: 8) and miR-557 (SEQ ID NO: 16). Some preferred RNAs therefore comprise: miR-125a-3p (SEQ ID NO: 1), miR-1271 (SEQ ID NO: 3), miR-1275 (SEQ ID NO: 4), miR-183 (SEQ ID NO: 8) and miR-557 (SEQ ID NO: 16). In another preferred embodiment the RNA is selected from the group consisting of RNA-125a-3p (SEQ ID NO:1), miR-1271 (SEQ ID NO:3), miR-1287 (SEQ ID NO:6), miR-183 (SEQ ID NO: 8), miR-185" (SEQ ID NO:9), miR-193b" (SEQ ID NO:10), miR-1978 (SEQ ID NO:11), miR-365* (SEQ ID NO:14), miR-557 (SEQ ID NO:16), miR-612 (SEQ ID NO:17), miR-644a (SEQ ID NO:18) and miR-885-3p (SEQ ID NO:19), more preferably the RNA is selected from the group consisting of: miR-1271 (SEQ ID NO: 3), miR-1287 (SEQ ID NO: 6), miR-183 (SEQ ID NO:8), miR-185* (SEQ ID NO: 9), miR-1978 (SEQ ID NO:11), miR-365* (SEQ ID NO:14), miR-557 (SEQ ID NO:16), miR-612 (SEQ ID NO:17), miR-644a (SEQ ID NO:18) and miR-885-3p (SEQ ID NO: 19), more preferably from the group consisting of miR-1271 (SEQ ID NO: 3), miR-1287 (SEQ ID NO:6), miR-1978 (SEQ ID NO:11) and miR-557 (SEQ ID NO:16). In one embodiment the RNA is miR-1978 (SEQ ID NO:11). In a preferred embodiment the RNA is miR-1287 (SEQ ID NO:6) or miR-557 (SEQ ID NO:16). The RNA of the invention may be an isolated RNA, preferably an isolated non-coding RNA, more preferably an isolated miRNA.

The invention also relates to combinations of two or more RNAs, preferably non-coding RNAs, more preferably miRNAs. Particularly preferred combinations of two RNAs are miR-557 (SEQ ID NO:16) and miR-1287 (SEQ ID NO:6), miR-557 (SEQ ID NO:16) and miR-1978 (SEQ ID NO:11), miRNA-1271 (SEQ ID NO: 3) and miR-1978 (SEQ ID NO:11) or miR-1287 (SEQ ID NO: 6) and miRNA-1978 (SEQ ID NO:11), with miR-557 (SEQ ID NO:16) and miR-1287 (SEQ ID NO:6) being the most preferred combination.

In one embodiment of this aspect the protein of interest is a recombinant protein. Preferably, the protein of interest is a therapeutic protein, as described above. In a specific embodiment the protein of interest is an antibody.

In a second aspect, the invention concerns a mammalian expression vector comprising a ribonucleic acid (RNA) selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

In one embodiment a mammalian expression vector is provided that encodes at least one ribonucleic acid (RNA) selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20. Preferably the mammalian expression vector comprises a polynucleotide sequence that comprises the at least one RNA.

In certain embodiments the RNA is a micro ribonucleic acid (miRNA) selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20. The skilled person will recognize that the RNA of this aspect is encoded by a polynucleotide sequence. Hence, the expression vector comprises a polynucleotide sequence encoding said RNA. An expression vector according to the present invention may also comprise a polynucleotide sequence encoding any of the RNAs of the first aspect. Typically, the polynucleotide sequence is a DNA sequence encoding a pre-miRNA, which is intracellularly processed to a mature miRNA. Expression of said RNA leads to an increase in the production and/or secretion of a protein of interest in a mammalian expression system. The protein of interest may be a recombinant protein, preferably a therapeutic protein as described above, more preferably the protein of interest is an antibody.

The expression vectors of the present invention may further comprise a selectable marker gene, such as an antibiotic resistance gene or an amplifiable marker gene. In a specific embodiment the expression vector comprises an amplifiable selection marker gene, such as a glutamine synthetase gene or a dihydrofolate reductase gene. The amplifiable selection marker gene, may be operably linked to the polynucleotide sequence encoding the RNA. To be operably linked, the polynucleotide sequence encoding the RNA and the amplifiable selection marker gene may be located on the same vector. In some embodiments, the expression vector of the invention may also comprise a gene of interest. In a further embodiment either the protein of interest or the RNA is operably linked to an amplifiable selection marker, such as glutamine synthetase or dihydrofolate reductase. Typically, the gene of interest and the polynucleotide sequence encoding the RNA in the expression vector of the invention are operably linked to a promoter and/or a terminator. The gene of interest or the polynucleotide sequence encoding the RNA operably linked to a promoter and/or a terminator may also be referred to as an expression cassette.

In a preferred embodiment the RNA is selected from the group consisting of: SEQ ID NO: 1, SEQ ID NO: 3, SEQ ID NO: 6, SEQ ID NO: 8, SEQ ID NO:9, SEQ ID NO: 10, SEQ ID NO: 11, SEQ ID NO:14, SEQ ID NO: 16, SEQ ID NO: 17, SEQ ID NO: 18, or SEQ ID NO: 19, more preferably the RNA is selected from the group consisting of: miR-1271 (SEQ ID NO: 3), miR-1287 (SEQ ID NO: 6), miR-183 (SEQ ID NO:8), miR-185* (SEQ ID NO: 9), miR-1978 (SEQ ID NO:11), miR-365* (SEQ ID NO:14), miR-557 (SEQ ID NO:16), miR-612 (SEQ ID NO:17), miR-644a (SEQ ID NO:18) and miR-885-3p (SEQ ID NO: 19) and more preferably the RNA is miR-1271 (SEQ ID NO: 3), miR-1287 (SEQ ID NO:6), miR-1978 (SEQ ID NO:11) or miR-557 (SEQ ID NO:16). In one embodiment the RNA is miR-1978 (SEQ ID NO:11). In another preferred embodiment the RNA is miR-1287 (SEQ ID NO:6) or miR-557 (SEQ ID NO:16). In yet another embodiment, the RNA is miR-125a-3p (SEQ ID NO: 1), miR-1271 (SEQ ID NO: 3), miR-1275 (SEQ ID NO: 4), miR-183 (SEQ ID NO: 8) or miR-557 (SEQ ID NO: 16), which are non-limiting examples or RNAs that function in a species-independent manner. In yet another embodiment the mammalian expression vector of the invention comprises a combination of several identical or different RNAs selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20. As the skilled person will understand, the expression vector according to the invention comprising a combination of several identical or different RNAs, comprises a polynucleotide sequence encoding a combination of several, i.e., two or more, of the RNAs, wherein the RNAs may be identical or different. An expression vector according to the invention may also comprise a polynucleotide sequence encoding a combination of two or more of the RNAs of the first aspect, wherein the RNAs may be identical or different. Typically, the polynucleotide sequence is a DNA sequence. Several identical or different RNAs may be two, two or more, three or more, etc. copies of the same RNA or of different RNAs and any combination thereof, i.e., one RNA and a different RNA, two identical RNAs, two identical and one different RNAs, three identical RNAs, three different RNAs, etc. Typically, a combination of several identical or different RNAs are two identical or two different RNAs. Preferably, the several identical or different RNAs are selected from the group consisting of: SEQ ID NO: 1, SEQ ID NO: 3, SEQ ID NO: 6, SEQ ID NO: 8, SEQ ID NO:9, SEQ ID NO: 10, SEQ ID NO: 11, SEQ ID NO:14, SEQ ID NO: 16, SEQ ID NO: 17, SEQ ID NO: 18, and SEQ ID NO: 19. More preferably the RNAs are selected from the group consisting of: miR-1271 (SEQ ID NO: 3), miR-1287 (SEQ ID NO: 6), miR-183 (SEQ ID NO:8), miR-185* (SEQ ID NO: 9), miR-1978 (SEQ ID NO:11), miR-365* (SEQ ID NO:14), miR-557 (SEQ ID NO:16), miR-612 (SEQ ID NO:17), miR-644a (SEQ ID NO:18) and miR-885-3p (SEQ ID NO: 19), most preferably, the RNAs are miR-1271 (SEQ ID NO: 3), miR-1287 (SEQ ID NO: 6), miR-1978 (SEQ ID NO: 11), miR-557 (SEQ ID NO: 16) or a combination thereof, even more preferably the RNAs are miR-557 (SEQ ID NO:16) and/or miR-1287 (SEQ ID NO:6).

In a specific embodiment the vector comprises a polynucleotide sequence encoding a combination of several miR-1978s (SEQ ID NO: 11) RNAs. The combination of several miRNA-1978s (SEQ ID NO:11) may be two, three or even more miRNA-1978s(SEQ ID NO:11), preferably two miRNA-1978s(SEQ ID NO:11). In a specific embodiment the mammalian expression vector comprises a combination of several identical RNAs, preferably two identical RNAs. Preferred is a combination of several miR-1978s (SEQ ID NO: 11) RNAs. In a preferred embodiment the mammalian expression vector encodes a combination of several identical miR-557s (SEQ ID NO: 16), preferably two miR-557s or a combination of several identical miR-1287s (SEQ ID NO:6), preferably two miR-1287s. In another preferred embodiment the mammalian expression vector encodes a combination of miR-557 (SEQ ID NO:16) and miR-1287 (SEQ ID NO:6), miR-557 (SEQ ID NO:16) and miR-1978 (SEQ ID NO:11), miRNA-1271 (SEQ ID NO: 3) and miR-1978 (SEQ ID NO:11) or miR-1287 (SEQ ID NO: 6) and miRNA-1978 (SEQ ID NO:11), preferably a combination of miR-557 (SEQ ID NO:16) and miR-1287 (SEQ ID NO:6).

Preferably, the RNA comprised in or encoded by any of the expression vectors of the invention is a small non-coding RNA such as a micro ribonucleic acid (miRNA). Preferably said non-coding RNA is a miRNA. The expression vector may further comprise at least one gene of interest. Typically, the polynucleotide sequences encoding the RNA and/or the gene of interest are operably linked to a promoter and/or a terminator. A gene of interest and the polynucleotide sequence encoding the RNA operably linked to a promoter and/or a terminator may also be referred to as an expression cassette. In yet another aspect the invention concerns a mammalian cell comprising one or more RNAs selected from one or more of the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20, preferably the RNA is selected from the group consisting of: SEQ ID NO: 1, SEQ ID NO: 3, SEQ ID NO: 6, SEQ ID NO: 8, SEQ ID NO:9, SEQ ID NO: 10, SEQ ID NO: 11, SEQ ID NO:14, SEQ ID NO: 16, SEQ ID NO: 17, SEQ ID NO: 18, and SEQ ID NO: 19, more preferably the RNA is selected from the group consisting of: miR-1271 (SEQ ID NO: 3), miR-1287 (SEQ ID NO: 6), miR-183 (SEQ ID NO:8), miR-185* (SEQ ID NO: 9), miR-1978 (SEQ ID NO:11), miR-365* (SEQ ID NO:14), miR-557 (SEQ ID NO:16), miR-612 (SEQ ID NO:17), miR-644a (SEQ ID NO:18) and miR-885-3p (SEQ ID NO: 19) and more preferably the RNA is selected from the group consisting of: miR-1271 (SEQ ID NO: 3), miR-1287 (SEQ ID NO:6), miR-1978 (SEQ ID NO:11), and miR-557 (SEQ ID NO:16). In one embodiment the RNA is miR-1978 (SEQ ID NO: 11). In another preferred embodiment the RNAs are miR-1287 (SEQ ID NO:6) and/or miR-557 (SEQ ID NO:16).

Further, the one or more RNAs comprised in the mammalian cell of the invention may be a combination of RNAs, preferably a combination of two RNAs. Preferably said two RNAs are miR-557 (SEQ ID NO:16) and miR-1287 (SEQ ID NO:6), miR-557 (SEQ ID NO:16) and miR-1978 (SEQ ID NO:11), miRNA-1271 (SEQ ID NO: 3) and miR-1978 (SEQ ID NO:11) or miR-1287 (SEQ ID NO: 6) and miRNA-1978 (SEQ ID NO:11), more preferably miR-557 (SEQ ID NO:16) and miR-1287 (SEQ ID NO:6).

It will be understood that the one or more RNAs are typically heterologous in respect of said mammalian cell, i.e., they (or the sequences encoding them) have been introduced, i.e, transfected into said cell. Preferably, the RNA of any of the mammalian cells of the invention is a non-coding RNA and more preferably the non-coding RNA is a miRNA. Thus, the mammalian cell of the invention further concerns a mammalian cell comprising/transfected with one or more miRNAs, preferably heterologous miRNAs, selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20, preferably the miRNA is selected from the group consisting of: SEQ ID NO: 1, SEQ ID NO: 3, SEQ ID NO: 6, SEQ ID NO: 8, SEQ ID NO:9, SEQ ID NO: 10, SEQ ID NO: 11, SEQ ID NO:14, SEQ ID NO: 16, SEQ ID NO: 17, SEQ ID NO: 18, and SEQ ID NO: 19, more preferably the miRNA is selected from the group consisting of: miR-1271 (SEQ ID NO: 3), miR-1287 (SEQ ID NO: 6), miR-183 (SEQ ID NO:8), miR-185* (SEQ ID NO: 9), miR-1978 (SEQ ID NO:11), miR-365* (SEQ ID NO:14), miR-557 (SEQ ID NO:16), miR-612 (SEQ ID NO:17), miR-644a (SEQ ID NO:18) and miR-885-3p (SEQ ID NO: 19), and even more preferably the miRNA is selected from the group consisting of: miR-1271 (SEQ ID NO: 3), miR-1287 (SEQ ID NO:6), miR-1978 (SEQ ID NO:11), or miR-557 (SEQ ID NO:16). In one embodiment the miRNA is miR-1978s (SEQ ID NO: 11) RNAs. In another preferred embodiment the mammalian cell comprises one or more of miR-1287 (SEQ ID NO:6) and/or miR-557 (SEQ ID NO:16). Further, the one or more miRNAs comprised in the mammalian cell of the invention may be a combination of miRNAs, preferably a combination of two miRNAs. Preferably, said two miRNAs are miR-557 (SEQ ID NO:16) and miR-1287 (SEQ ID NO:6), miR-557 (SEQ ID NO:16) and miR-1978 (SEQ ID NO:11), miRNA-1271 (SEQ ID NO: 3) and miR-1978 (SEQ ID NO:11) or miR-1287 (SEQ ID NO: 6) and miRNA-1978 (SEQ ID NO:11), more preferably miR-557 (SEQ ID NO:16) and miR-1287 (SEQ ID NO:6).

Any one of the mammalian cells of the invention is preferably transfected with said one or more RNAs. More preferably, the mammalian cell of the invention is stably transfected with an expression vector encoding said RNA, such as any of the expression vectors of the present invention. Thus, the mammalian cell of the present invention may be a stably miRNA engineered mammalian cell. The mammalian cell may further express a protein/product of interest, wherein the protein of interest may be endogenously expressed by the host cell or the host cell is further transiently or stably transfected with an expression vector encoding the protein/product of interest. Preferably the mammalian cell is further stably transfected with an expression vector encoding the protein/product of interest. Sufficiently high stable levels of said RNA in the host cell or the producer cell may be achieved, e.g., by cloning multiple copies of the RNA encoding polynucleotide into the expression vector. The mammalian host cell stably transfected with one or more RNAs of the invention may be subjected to batch or fed-batch fermentations.

The one or more RNA of the invention lead to an increase in the production and/or secretion of a protein of interest, further expressed by said mammalian cell. Preferably said protein of interest is a recombinant protein, more preferably a therapeutic protein, even more preferably a therapeutic antibody as described above.

In one embodiment the production and/or secretion of the protein of interest by the mammalian cell of the invention is increased by 10%, 20%, 50%, 100%, 200%, 400% compared to a control cell, which is not transfected with at least one RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20. The invention further concerns a mammalian cell comprising the mammalian expression vector of the invention as described above. Also provided herein is the mammalian cell of the invention, wherein the RNA, preferably the miRNA, is encoded by the expression vector according to the invention.

Preferably, the mammalian cell of the invention is a rodent or a human cell. In a specific embodiment the human cell is a HEK-293 cell, a PER.C6 or a CAP cell. More preferably, the mammalian cell is a rodent cell, even more preferably a CHO cell, and most preferably a CHO-DG44 cell.

The human RNA or microRNA provided herein can be transiently or stably introduced into pre-existing producer cell lines secreting a therapeutic protein of interest. Alternatively, the RNA or miRNA can either individually or in combination be introduced or over-expressed in a host cell line to generate a superior host cell that is an miRNA engineered host cell as basis for producer cell line development.

It should be pointed out that miRNA-based engineering approaches of the invention are also well suited to be combined with classical cell engineering approaches, since they do not add to the metabolic burden of the engineered cell. For example, an engineering approach with proven benefit on secretion (e.g. over-expression of a transgene such as XBP-1 or BiP or selected product quality attributes) could be combined with a (mi)RNA-based engineering approach to address additional features of cell behavior.

In another aspect, the invention concerns a method of/for developing a (high-producing) stably transfected mammalian cell, comprising the following steps:
(a) transfecting at least one RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 into the mammalian cell,
(b) cultivating said cell for an initial period of time in the presence of selective pressure, and
(c) selecting a high-producing transfected cell.

The skilled person will know that transfecting the at least one RNA into the mammalian cell comprises transfecting an expression vector encoding the at least one RNA into said mammalian cell, wherein the expression vector is stably transfected. Hence, the expression vector comprises a polynucleotide sequence encoding said RNA. The stably transfected mammalian cell is a mammalian cell that is stably transfected with at least one RNA of the invention and may also be referred to as stably RNA or miRNA engineered host cell. The expression vector may be the expression vector of the invention as described above. Typically, the expression vector further comprises a selectable marker gene as described above, wherein the selectable marker gene may be an amplifiable selectable marker gene. Sufficiently high stable levels of said RNA in the host cell or the producer cell may be achieved, e.g., by cloning multiple copies of the RNA encoding polynucleotide into the expression vector.

The term "high-producing transfected cell" as used herein relates to the production of a protein/product of interest at high specific productivity and/or at high titers, wherein the protein is preferably secreted. The mammalian cell used in this aspect may endogenously express the protein/product of interest. Alternatively, the mammalian cell stably transfected in step (a) may be a producer host cell already comprising at least one expression vector comprising a gene of interest. This may be any new or established cell line developed for stably expressing the protein of interest. Alternatively, the RNA in this aspect can either individually or in combination be introduced or over-expressed in a host cell line to generate a superior host cell as basis for producer cell line development. The mammalian cell stably transfected in step (a) may also be selected for a high-producing transfected host cells in step (c) by transiently or stably transfecting the cell of step (b) with an expression vector encoding the protein of interest. The skilled person will understand that cultivating said cell in step (b) in the presence of selective pressure for an initial period of time, serves to enrich for the stably transfected host cells of step (a). For protein production, the high-producing transfected cell of step (c) may be subjected to batch or fed-batch fermentation.

In one embodiment of the above aspect, the invention concerns a method of/for developing a high-producing stably transfected mammalian (host) cell (line), comprising the following steps:
(a) transfecting a polynucleotide sequence encoding at least one miRNAs selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 into the mammalian cell,
(b) cultivating said cell (for an initial period) in the presence of selective pressure (thus to enrich for the stably transfected (host) cell of step (a)), and
(c) selecting a high-producing transfected (host) cell.

A specific example of such a cell development method is provided in Example 11.

In a specific embodiment of this aspect the cell in step a) is transfected with the vector of the invention as described above.

In a further embodiment the cell in step a) is a producer host cell comprising a vector encoding for a gene of interest.

In yet another aspect, the invention provides a method of/for producing a protein of interest, comprising the following steps:
(a) transfecting at least one RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 and at least one expression vector comprising at least one gene of interest into a mammalian cell,
(b) selecting a highly-productive transfected cell,
(c) cultivating the highly-productive transfected cell obtained in step (b) under conditions which allow expression of the gene(s) of interest, and
(d) harvesting and purifying the protein of interest.

The skilled person will know that transfecting the at least one RNA into the mammalian cell may comprise transfecting an expression vector encoding at least one of said RNAs into said mammalian cell, wherein the expression vector is preferably stably transfected. Hence, the expression vector comprises a polynucleotide sequence encoding said RNA. Transfecting the at least one RNA or the expression vector encoding the at least one RNA may be done after, prior to or simultaneously to transfecting the gene of interest. Alternatively, the expression vector comprising the at least one gene of interest of step (a) may also encode the at least one RNA of step (a).

In certain embodiments the mammalian cell in step (a) is transfected with any of the expression vectors of the present invention, preferably the mammalian cell in step (a) is stably transfected with any of the expression vectors of the present invention.

The production cells derived from RNA or microRNA engineered host cells show higher production and/or secretion rates, i.e. specific productivity and/or higher titers. The RNA or microRNA engineering of step (a) can either be done after, prior to or simultaneously to introducing the gene of interest with similar results, thus offering a broad range of options for applications in pharmaceutical development processes. Sufficiently high stable levels of RNA in the host cell or the producer cell may be achieved, e.g., by cloning multiple copies of the RNA encoding polynucleotide into an expression vector. Cultivating the cells under conditions which enable expression of the genes of interest according to step (c) may comprise subjecting the cell to batch or fed-batch fermentations.

In a specific embodiment of this aspect, the polynucleotide sequence encoding said RNA is integrated into the mammalian expression vector comprising the at least one gene of interest. Hence, the expression vector comprises a polynucleotide sequence encoding the RNA of the invention and the gene of interest.

Thus, the invention further concerns a method of/for producing a protein of interest, characterised by the following steps:
(a) integrating at least one RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 into a mammalian expression vector comprising at least one gene of interest,
(b) transfecting a mammalian cell with said expression vector,
(c) selecting a highly-productive transfected cell,
(d) cultivating the highly-productive transfected cell obtained in step (c) under conditions which allow expression of the gene(s) of interest, and optionally
(e) harvesting and purifying the protein of interest.

The invention also concerns a method of producing a heterologous protein of interest in a mammalian cell comprising
a) transfecting said mammalian cell with the RNA as described above or a vector as described above, and
b) effecting the expression of said protein of interest.

The invention further concerns a method of/for preparing and selecting a recombinant mammalian cell, comprising the following steps:
(a) transfecting a mammalian cell with genes that encode at least for a protein/product of interest and an amplifiable selectable marker, such as DHFR or GS and wherein the (host) cell is (co-) transfected with at least one RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20,
(b) selecting a cell with (co-)integrated genes by cultivating the cell in the presence of a selective agent, such as e.g. in a hypoxanthine/thymidine-free or glutamine-free medium, and
(b') amplifying these (co-)integrated genes by cultivating the cell in the presence of an agent which allows the amplification of at least the amplifiable selectable marker gene, such as e.g. methotrexate or MSX,
(c) cultivating the cell under conditions which enable expression of the (different) genes.

In an alternative embodiment the invention concerns a method of/for preparing and selecting a recombinant mammalian cell, characterised by the following steps:
(a) transfecting a mammalian cell with genes that encode at least for a protein/product of interest and a selectable marker, such as a selectable marker conferring resistance to neomycin, puromycin, bleomycin, zeocin or blasticidin and wherein the (host) cell is (co-)transfected with at least one RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20,
(b) selecting a cell with (co-)integrated genes by cultivating the cells in the presence of a selective agent, and
(c) cultivating the cell under conditions which enable expression of the (different) genes.

The skilled person will recognize that transfecting the at least one RNA into the mammalian cell according to step (a) of any of the methods of the invention comprises transfecting an expression vector encoding at least one of said RNAs into said mammalian cell, wherein preferably the expression vector is stably transfected. Hence, the expression vector comprises a polynucleotide sequence encoding said RNA. In certain embodiments the expression vector may be the expression vector of the invention as described above. Sufficiently high stable levels of said RNA in the host cell or the producer cell may be achieved, e.g., by cloning multiple copies of the RNA encoding polynucleotide into the expression vector. In the context of the invention the expression vector encoding the RNA of the invention may further comprise a gene of interest. The expression vector encoding the RNA of the invention may also comprise genes that encode at least a protein/product of interest and a selectable marker. Alternatively, the expression vector encoding the RNA of the invention may be transfected after, prior to or simultaneously to transfection of the at least one gene of interest, i.e., the genes that encode a protein/product of interest. Cultivating the cells under conditions which enable expression of the genes according to step (c) may comprise subjecting the cell to batch or fed-batch fermentations.

In a specific embodiment of any of the above methods of the invention the production and/or secretion of the protein of interest is increased by 10%, 20%, 50%, 100%, 200%, 400% compared to a control cell, which is not transfected with at least one RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

In a specific embodiment of any of the above methods of the invention the proportion of high producers/high producer cells is increased up to two-fold, three-fold, four-fold, five-fold, six-fold, seven-fold or ten-fold or more than two-fold, more than three-fold, more than four-fold, more than five-fold, more than seven-fold or more than ten-fold. The increase is preferably measured in relation to a control cell which is not transfected with at least one RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20. A high producer cell is a cell, which produces the protein/product of interest with a high titer and/or a high specific cellular productivity, preferably in an amount sufficient to enable a commercially viable biopharmaceutical production process.

In a preferred embodiment of any of the above methods of the invention said RNA is a small non-coding RNA such as a micro ribonucleic acid (miRNA). More preferably said RNA is a miRNA.

In a certain embodiments of any of the methods of the invention the at least one ribonucleic acid (RNA) is selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

In a further embodiment of any of the methods of the invention the at least one RNA is SEQ ID NO: 1, SEQ ID NO: 3, SEQ ID NO: 6, SEQ ID NO: 8, SEQ ID NO:9, SEQ ID NO: 10, SEQ ID NO: 11, SEQ ID NO:14, SEQ ID NO: 16, SEQ ID NO: 17, SEQ ID NO: 18, SEQ ID NO: 19, or a combination thereof. Preferably the RNA is selected from the group consisting of: miR-1271 (SEQ ID NO: 3), miR-1287 (SEQ ID NO: 6), miR-183 (SEQ ID NO:8), miR-185* (SEQ ID NO: 9), miR-1978 (SEQ ID NO:11), miR-365* (SEQ ID NO:14), miR-557 (SEQ ID NO:16), miR-612 (SEQ ID NO:17), miR-644a (SEQ ID NO:18) and miR-885-3p (SEQ ID NO: 19), or a combination thereof, more preferably the at least one RNA is miR-1271 (SEQ ID NO: 3), miR-1287 (SEQ ID NO: 6), miR-1978 (SEQ ID NO: 11), miR-557 (SEQ ID NO: 16) or a combination thereof. Most preferably the RNA is miR-1287 (SEQ ID NO: 6) and/or miR-557 (SEQ ID NO: 16).

The at least one transfected RNA may be a combination of RNAs, preferably a combination of two RNAs. Preferably said two RNAs are miR-557 (SEQ ID NO:16) and miR-1287 (SEQ ID NO:6), miR-557 (SEQ ID NO:16) and miR-1978 (SEQ ID NO:11), miRNA-1271 (SEQ ID NO: 3) and miR-1978 (SEQ ID NO:11) or miR-1287 (SEQ ID NO: 6) and miRNA-1978 (SEQ ID NO:11), more preferably miR-557 (SEQ ID NO:16) and miR-1287 (SEQ ID NO:6).

In yet another embodiment of any of the methods of the invention, the RNA is miR-125a-3p (SEQ ID NO: 1), miR-1271 (SEQ ID NO: 3), miR-1275 (SEQ ID NO: 4), miR-183 (SEQ ID NO: 8) or miR-557 (SEQ ID NO: 16), which are non-limiting examples of RNAs that function in a species-independent manner.

In a specific embodiment of any of the methods of the present invention said methods may further comprise the following additional step: harvesting and purifying the protein of interest.

The protein of interest in any of the methods of the invention may be a recombinant protein, preferably a therapeutic protein as described above, such as an antibody or an Fc-fusion protein.

The mammalian cells used in any of the methods of the invention may be a rodent or a human cell. In one embodiment the cell is a human cell and the human cell may be, but is not limited to a HEK-293 cell, a PER.C6 or a CAP cell. Preferably, the cell used in any of the above methods is a rodent cell, more preferably a CHO cell, most preferably a CHO-DG44 cell.

In another aspect, the invention concerns the use of a RNA selected from the group consisting of:
SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 as a production-promoting element for the preparation of a product/protein of interest. Thus, the product/protein of interest may be a therapeutical protein or a biopharmaceutical product that is intended as a medicament for medical use. Alternatively the invention also concerns the use of a RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 for increasing the production and/or secretion of a product of interest from a mammalian cell.

Preferably, the product of interest according to any of the uses of the invention is a protein of interest, more preferably the protein of interest is a recombinant protein, such as a therapeutic protein or an antibody as described herein. In a particularly preferred embodiment, the protein of interest is an antibody or antibody fragment or antibody fusion protein or an antibody conjugate or antibody Fc-fusion protein.

The invention further concerns the use of a RNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20 for the production of a non-human transgenic animal, preferably a mammal.

In one embodiment the invention provides a use of the mammalian cell of the invention for producing a protein of interest, wherein preferably said mammalian cell is a stably miRNA engineered cell.

The RNA according to any of the uses of the invention is preferably a small non-coding RNA such as a micro ribonucleic acid (miRNA). More preferably said RNA is a miRNA.

In one embodiment of any of the above uses the ribonucleic acid (RNA) is selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

In another embodiment of any of the above uses the RNA is SEQ ID NO: 1, SEQ ID NO: 3, SEQ ID NO: 6, SEQ ID NO: 8, SEQ ID NO:9, SEQ ID NO: 10, SEQ ID NO: 11, SEQ ID NO:14, SEQ ID NO: 16, SEQ ID NO: 17, SEQ ID NO: 18, or SEQ ID NO: 19. Preferably the RNA is miR-1271 (SEQ ID NO: 3), miR-1287 (SEQ ID NO: 6), miR-1978 (SEQ ID NO: 11), or miR-557 (SEQ ID NO: 16), more preferably the RNA is selected from the group consisting of: miR-1271 (SEQ ID NO: 3), miR-1287 (SEQ ID NO: 6), miR-183 (SEQ ID NO:8), miR-185* (SEQ ID NO: 9), miR-1978 (SEQ ID NO:11), miR-365* (SEQ ID NO:14), miR-557 (SEQ ID NO:16), miR-612 (SEQ ID NO:17), miR-644a (SEQ ID NO:18) and miR-885-3p (SEQ ID NO: 19). Most preferably the RNA is miR-1287 (SEQ ID NO: 6) and/or miR-557 (SEQ ID NO: 16).

Further, the RNA in any of the uses of the invention may be a combination of RNAs, preferably a combination of two RNAs. Preferably said two RNAs are miR-557 (SEQ ID NO:16) and miR-1287 (SEQ ID NO:6), miR-557 (SEQ ID NO:16) and miR-1978 (SEQ ID NO:11), miRNA-1271 (SEQ ID NO: 3) and miR-1978 (SEQ ID NO:11) or miR- 1287 (SEQ ID NO: 6) and miRNA-1978 (SEQ ID NO:11), more preferably miR-557 (SEQ ID NO:16) and miR-1287 (SEQ ID NO:6).

In another embodiment of any of the above uses, the RNA is miR-125a-3p (SEQ ID NO: 1), miR-1271 (SEQ ID NO: 3), miR-1275 (SEQ ID NO: 4), miR-183 (SEQ ID NO: 8) or miR-557 (SEQ ID NO: 16), which are non-limiting examples of RNAs that function in a species-independent manner.

Preferably, any of the cells according to any of the uses of the invention is a rodent or a human cell. In one embodiment the human cell is a HEK-293 cell, a PER.C6 or a CAP cell. Preferably, the cell used in any of the above uses is a CHO cell, most preferably a CHO-DG44 cell.

The practice of the present invention will employ, unless otherwise indicated, conventional techniques of cell biology, molecular biology, cell culture, immunology and the like which are in the skill of one in the art. These techniques are fully disclosed in the current literature.

All publications and patent applications mentioned in this specification are indicative of the level of skill of those skilled in the art to which this invention pertains. All publications and patent applications cited herein are hereby incorporated by reference in their entirety in order to more fully describe the state of the art to which this invention pertains. The invention generally described above will be more readily understood by reference to the following example, which is hereby included merely for the purpose of illustration of certain embodiments of the present invention and is not intended to limit the invention in any way.

| MATERIALS AND METHODS CELL LINES | | |
|---|---|---|
| Designation | Description | Species |
| CHO/BIWA4 | CHO-DG44-based producer cell clone secreting an IgG1 product | Hamster |
| CHO/BIBH1 | CHO-DG44-based producer cell clone secreting an IgG1 product | Hamster |
| CHO/HSA | CHO-based cell pool producing human Albumin | Hamster |
| HEK293 t-rex flp-IN cells/ssHRP-flag | Human kidney cells transfected to secret a horse-raddish-peroxidase reporter protein | Human |
| HeLa cells | Human cervix epithelial adenocarcinoma cells | Human |
| INS-1 | Rat insulinoma cells endogenously secreting insulin | Rat |

Human MicroRNA Library

The human microRNA library is obtained from Dharmacon (CS-001010 mimic microRNA library; lot number 09167).

Cell Culture of Suspension Cells

Suspension cultures of mAb producing CHO-DG44 cells (Urlaub et al., 1986) and stable transfectants thereof are incubated in a BI proprietary chemically defined, serum-free media. Seed stock cultures are sub-cultivated every 2-3 days with seeding densities of $3\times10^5$-$2\times10^5$ cells/mL respectively. Cells are grown in T-flask (Greiner). T-flasks are incubated in humidified incubators (Varolab) at 37° C. and 5% $CO_2$. The cell concentration and viability is determined by trypan blue exclusion using a counting chamber.

Cell Culture of INS-1 Cells

INS-1 cells are cultured in RPMI 1640, 10% FCS, 10 mM HEPES, 50 µM 2-Mercaptoethanole, 1 mM Na-Pyruvate, 2 mM Glutamate in humidified incubators at 37° C. and 5% $CO_2$. Insulin secreted from INS-1 cells is determined using the rat insulin ELISA 80-INSRT-E01 (alpco), following the manufacturer's instructions.

Cell Culture of HEK293 FlpIN Cells and Hela Cells

HEK293, FlpIN and HeLa cells were cultured in DMEM or RPMI1640 (Life Technologies), respectively, both supplemented with 10% FCS in humidified incubators at 37° C. and 5% $CO_2$. Cells were subcultivated by trypsinization every 3 to 4 days when reaching confluency.

Fed-Batch Cultivation

Cells are seeded at $3\times10^5$ cells/ml into 125 ml shake flasks (Corning) in 30 ml of BI-proprietary production medium without antibiotics or MTX. The cultures are agitated at 120 rpm in 37° C. and 5% $CO_2$ in minitron incubator (Infors) which is reduced to 2% following day 3. BI-proprietary feed solution is added daily and pH is adjusted to pH 7.0 using $NaCO_3$ as needed. Cell densities and viability are determined by trypan-blue exclusion using an automated counting chamber TC10 (Biorad). Cumulative specific productivity is calculated as product concentration analysed by ELISA at the given day divided by the "integral of viable cells" (IVC) until that time point.

Transient Expression of Human MicroRNAs in CHO Producer Cells-MicroRNA Screen

CHO-DG44 cells stably secreting an IgG1 antibody are cultivated in BI proprietary chemically defined, serum-free medium (Boehringer-Ingelheim) supplemented with 500 µg/mL G418 (Gibco, Life technologies) and 400 nM MTX (Sigma-Aldrich, Germany) and are subcultivated every 2 or 3 days with a seeding density of $3\times10^5$ cells/mL or $2\times10^5$ cells/mL, respectively.

Cells are transfected via nucleofection one day after subcultivation (4e5 cells/sample) in 96-well NUCLEOFECTOR Nucleofection Kit SG (Lonza) containing 1 µM RNA using the Amaxa 96-well Shuttle Device (Lonza) and program 96-DT-133 according to the manufacturer's instructions. Cells are then seeded with a density of $3\times10^5$ cells/mL into 4 96-well flat bottom plates (Greiner). One day after transfection the volume of the medium is doubled by addition of fresh medium. Supernatants are collected on days 1-4 post transfection and stored at −20° C. until antibody measurement by ELISA. As negative controls a mimic microRNA negative control #1 (Dharmacon) and a non-targeting siRNA coupled with FITC (siLacZ-FITC) are used. FITC positive cells are measured by flow cytometry to determine the transfection efficiency. As a positive control, a siRNA targeting the light chain of the IgG1 antibody is transfected resulting in decreased antibody concentrations. The microRNA library is obtained from Dharmacon (CS-001010 mimic microRNA library) and the siRNAs are from MWG.

Antibody concentrations are normalized to the mean values of all samples contained in the plate and compared with those of the non-targeting and negative controls.

Validation Screen

CHO-DG44 cells are transfected via nucleofection as described above and seeded into 12-well plates (Greiner). Cell densities and viability are determined by trypan blue exclusion using a CEDEX cell quantification system (Roche). Product concentrations in the supernatant are measured by ELISA.

Determination of Recombinant Antibody Concentration

To assess recombinant antibody production in transfected cells, supernatants are collected from cell cultures at the given time points. The product concentration is then analyzed by enzyme linked immunosorbent assay (ELISA). The concentration of secreted monoclonal antibody product is measured using HRP-conjugated antibodies against the human Fc fragment (Jackson Immuno Research Laboratories) and the human kappa light chain (Sigma).

Transfection of INS-1 Cells

INS-1 cells are transfected by nucleofection. Cells are trypsinized and $6 \times 10^6$ cells/sample are nucleofected with kit V (Lonza) and 2 µM RNA using program T-27.

Crystal Violet Assay

Cells are washed with PBS and 500 µL crystal violet staining solution (0.1% in 20% methanol) per 24-well are incubated for 20 minutes at room temperature. The plates are washed, dried and the dye is dissolved in 200 µL methanol per well by shaking for 30 minutes. 50 µL are transferred into 96-well plate and measured with a multiscan reader (Thermo Scientific) at 550 nm.

Insulin Assay

Nucleofected INS1E cells are trypsinized and replated into 6 wells of a 24 well plate. One day later, cells are washed twice with KRB (Krebs Ringer Buffer: 135 mM NaCl, 3.6 mM KCl, 1.5 mM $CaCl_2$, 0.5 mM $NaH_2PO_4$, 0.5 mM $MgCl_2$, 5 mM $NaHCO_3$, 0.1% bovine serum albumin, 10 mM HEPES) 0.5 ml per well and preincubated for 2 hours in KRB (1 mL per well). KRB is removed and new KRB with or without 20 mM glucose is added. Cells are incubated for 15 minutes before the supernatant is collected and stored at −20° C. Rat insulin concentration is measured by ELISA (80-INSRT-E01 from alpco).

Human Albumin ELISA

Albumin concentrations in cell culture supernatants are analyzed by ELISA (Bethyl Labs) according to manufacturer's instructions. As a coating antibody goat anti-human albumin and as a detection antibody HRP-conjugated goat anti-human albumin is used. To generate a standard curve a reference serum provided in the kit is used (Bethyl Labs).

Interleukin-8 (IL-8) Secretion Assay

HeLa cells were reverse transfected with microRNAs using RNAiMAX transfection agent sold under the trademark LIPOFECTAMINE (Life Technologies) according to manufacturer's instructions for 24-well plates (Greiner Bio-One). Two days post transfection cells were washed, medium was replaced by fresh cell culture medium and cell culture supernatants were harvested after 6 and 24 hours. The concentration of IL-8 in clarified cell supernatants was quantified by ELISA (human IL-8 ELISA Set, ImmunoTools) according to the manufacturer's instructions and results were normalized to the miRNA negative control. Mock-transfected cells served as an additional control.

Transient HRP Secretion Assay

HeLa cells were reverse transfected with microRNAs using RNAiMAX transfection agent sold under the trademark LIPOFECTAMINE (Life Technologies) according to manufacturer's instructions (Greiner Bio-One). Two days later, cells were transfected with a plasmid encoding ssHRP-FLAG using Mirus Hela Monster (Mirus). After 24 hours, cells were washed and medium was replaced by fresh serum-free and phenol red-free medium (RPMI1640) and cell culture supernatants were harvested after 4 and 6 hours. The amount of ssHRP in clarified cell supernatants was quantified by addition of ECL reagent (Pierce) and measurement of the luminescence signal (relative luminescence units) with a luminometer (Tecan) in white 96-well plates (Nunc). Relative luminescence units (RLU) were normalized to those of the miRNA neg. control. Untransfected and mock-transfected cells served as additional controls.

Stable HRP Secretion Assay

HEK293 FlpIn cells stably secreting ssHRP-Flag are reverse transfected with microRNAs using RNAiMAX transfection agent sold under the trademark LIPOFECTAMINE (Invitrogen) according to manufacturer's instructions in collagen coated 24-well plates (Greiner Bio-One). Two days post transfection, ssHRP expression is induced by addition of 20 ng/ml doxycycline (Merck). After 12 hours, medium is replaced by fresh serum-free and phenol red-free medium and cell culture supernatant is harvested after 5 hours. The amount of ssHRP in clarified cell supernatants is quantified by addition of ECL reagent (Pierce) and luminescence signal is measured with a luminometer (Tecan) in white 96-well plates (Nunc). Relative luminescence unites are normalized to miRNA neg. control luminescence signals. To normalize for cell density, a crystal violet assay is performed after supernatant collection and relative luminescence units are divided by crystal violet signals.

Generation of Antibody-Producing Cells

CHO-K1 or CHO-DG44 cells (Urlaub et al., Cell 1983) are stably transfected with expression plasmids encoding heavy and light chains of an IgG1-type antibody. Selection is carried out by cultivation of transfected cells in the presence of the respective antibiotics encoded by the expression plasmids. After about 3 weeks of selection, stable cell populations are obtained and further cultivated according to a standard stock culture regime with subcultivation every 2 to 3 days. In a next (optional) step, FACS-based single cell cloning of the stably transfected cell populations is carried out to generate monoclonal cell lines.

Stable Over Expression of MicroRNAs

Genomic microRNA sequences with approximately 300 bp flanking regions are subcloned from pCMV-mir vectors (Origene) into pBIP-1 (BI) containing a CMV promoter and a puromycin resistance cassette (pBIP-1-mir plasmid). CHO-DG44 cells stably secreting an IgG1 are transfected with LIPOFECTAMINE 2000 transfection agent and Plus reagent (Invitrogen) using an optimized protocol with pBIP-1-mir plasmids and cells are selected with 10 µg/mL puromycin. Single clones are generated by limited dilution. Overexpression is verified by qPCR analysis. Alternatively, the BLOCK-iT™ Pol II miR RNAi expression vector kit (PcDNA6.2-GW/emGFP-miRNA expression system kit) was used for stably expressing miRNAs. DNA oligonucleotides encoding one or multiple copies of a specific or of different microRNAs are cloned as short hairpins into the mammalian expression vector pcDNA6.2.

For that purpose, DNA oligonucleotides encoding the respective miRNAs are designed as described in the manual. In brief, the mature miRNA sequence was embedded in a given sequence including an optimized hairpin loop sequence and 3' and 5' flanking regions derived from the murine miRNA mir-155 (Lagos-Quintana et al., 2002). The flanking regions are present on the vector and a DNA oligonucleotide is designed, which encodes the miRNA sequence, the mentioned loop and the antisense sequence of the respective mature miRNA with a 2 nucleotide depletion to generate a internal loop in the hairpin stem. Furthermore, overhangs are added for cloning at both ends. Hairpin structure may be analyzed using the online tool mfold (M. Zuker. Mfold web server for nucleic acid folding and hybridization prediction. Nucleic Acids Res. 31 (13), 3406-3415, 2003). DNA strands are annealed and ligated into the 3'-UTR of emerald GFP reporter protein gene as described by the manufacturer. A vector containing more than one miRNA may be generated applying the chaining technique. The negative control miRNA (supplied by the manufacturer) and the siLacZ may be used as appropriate negative controls.

The BLOCK-iT™ Pol II miR RNAi expression vector kit (PcDNA6.2-GW/emGFP-miRNA expression system kit) is also used to express more than one miRNA or one miRNA with multiple copies. In brief two copies of specific microRNAs (e. g. hsa-miR557, hsa-miR1287 or miR1978 indicated by pcDNA6.2-GW/emGFP-miR557-miR557, pcDNA6.2-GW/emGFP-miR1287-miR1287 or pcDNA6.2-GW/emGFP-miR1978-miR1978) or different microRNAs (e.g. pcDNA6.2-GW/emGFP-miR557-miR1287, pcDNA6.2-GW/emGFP-miR557-miR1978 or pcDNA6.2-GW/emGFP-miR1287-miR1978) are cloned as DNA oligonucleotides encoding said miRNAs as short hairpins into the mammalian expression vector pcDNA6.2-GW/emGFP-miRNA (BLOCK-iT™ Pol II miR RNAi expression vector kit, K4936-00 from life technologies). The oligonucleotide sequences used for cloning of miRNAs into the vector backbone are as follows:

```
hsa-miR-557 forward:
                                  (SEQ ID NO: 21)
5'-TGCTGGTTTGCACGGGTGGGCCTTGTCTGTTTTGGCCACTGACTGAC

AGACAAGGCCCACGTGCAAAC-3' hsa-miR-557 reverse:
                                  (SEQ ID NO: 22)
5'-CCTGGTTTGCACGTGGGCCTTGTCTGTCAGTCAGTGGCCAAAACAGA

CAAGGCCCACCCGTGCAAACC-3' hsa-miR-1287 forward:
                                  (SEQ ID NO: 23)
5'-TGCTGTGCTGGATCAGTGGTTCGAGTCGTTTTGGCCACTGACTGACG

ACTCGAACCACATCCAGCA-3' hsa-miR-1287 reverse:
                                  (SEQ ID NO: 24)
5'-CCTGTGCTGGATGTGGTTCGAGTCGTCAGTCAGTGGCCAAAACGACT

CGAACCACTGATCCAGCAC-3 hsa-miR-1978 forward:
                                  (SEQ ID NO: 25)
5'-TGCTGGGTTTGGTCCTAGCCTTTCTAGTTTTGGCCACTGACTGACTA

GAAAGGCTAACCAAACC-3' hsa-miR-1978 reverse:
                                  (SEQ ID NO: 26)
5'-CCTGGGTTTGGTTAGCCTTTCTAGTCAGTCAGTGGCCAAAACTAGAA

AGGCTAGGACCAAACCC-3'
```

The chaining method was used to clone two copies of specific microRNAs into these constructs as described in the manufacturer's manual. In brief, the miRNA cassette was excised with the enzymes BamHI and XhoI. The vector containing already one miRNA was opened with the enzymes BglII and XhoI. DNA was mixed with orange loading buffer and was separated in a 1 agarose gel prepared with TAE buffer, bands were visualized with ethidium bromide and bands of appropriate size were excised from the gel. Size was verified with DNA ladder. DNA was eluted with the gel extraction kit. DNA insert was ligated into the vector using T4 DNA ligase according to manufacturers instructions. Subsequently, competent *E. coli* were transformed with the DNA and plated on agar plates containing spectinomycin. Colonies were picked and DNA was extracted with a DNA purification kit, checked by control digest with BamHI and BglII first, followed by sequencing.

Stable cell lines were generated by transfection as described above, selection with 10 μg/mL blasticidin S (Life Technologies) and FACS enrichment for GFP positive cells (FACSdiva). Cells were analysed by flow cytometry for GFP expression and in parallel qPCR analysis was done to monitor miRNA overexpression. Single clones are generated by limited dilution of unsorted stable pools. As control vectors either a negative control miRNA expressing vector (pcDNA6.2-GW/emGFP-neg. control miRNA, provided by the kit) or an empty vector (pcDNA6.2-GW/emGFP) both expressing GFP were stably transfected as described.

Fed-batch cultivations were performed with the different miRNA-overexpressing stable pools, the control pools and the parental cells, which are CHO-DG44 cells stably secreting an IgG1. Furthermore single clones were evaluated during fed-batch cultivation.

MicroRNA Expression Measurement by QPCR Analysis $2 \times 10^5$ to $2 \times 10^6$ cells are used for RNA extraction with mirVANA miRNA isolation kit (Ambion). As a positive control CHO-DG44 cells are transiently transfected with mature microRNA. cDNA is generated with 10 ng RNA using Taqman microRNA reverse transcription kit (Applied Biosystems) according to the manufacturer's instructions. qPCR is performed with Taqman microRNA assays (Applied Biosystems) using a Cfx96 device (Bio-rad). RNU6B is used as reference. Calculation is done with the single threshold method and $\Delta\Delta Cq$ values are calculated (Bio-rad CFX manager software 2.1).

Antibody Purification

Cell culture supernatant produced during fed-batch cultivation was concentrated using 50 kDa Amicon centrifugal filter units (Millipore). The concentrate containing the antibody was purified with Protein A HP spin trap columns (GE Healthcare) according to the manufacturer's instructions. The antibody elution buffer comprises 0.1 M glycine-HCl neutralized with 1 M Tris-HCl to pH 7. Amino groups, however, interfere with the downstream glycosylation analysis. Hence, the buffer was exchanged to PBS (Gibco) using the same filter units as before. Protein concentration was determined photometrically by measuring absorbance at 280 nm using a NANODROP spectrometer (ThermoScientific) and the protein specific extinction coefficient. Antibody quality was assessed by standard reducing SDS PAGE. Heavy and light chains at 50 kDa and 25 kDa were observed, with no other significant bands present.

Analysis of the Glycosylation Pattern

To elucidate the structure and composition of the Fc-glycosylation of IgGs produced in the miRNA cell lines, the glycans are released from the purified antibody after reduction by enzymatic digestion with PNGase F. Glycans are purified, fluorescently labelled with 2-Aminobenzamide (2-AB) and fractionated on a HPLC column. The percentages of the glyco-forms present are calculated from the chromatographic peak area ratios and allow the qualitative and quantitative verification of the glycostructures and composition. Alternatively, purified glycans are labelled with a fluorescent dye and separated by microchip-based capillary gel electrophoresis (CGE), e.g., using the PROFILERPRO Glycan Profiling Kit Ver 2 on a LABCHIP GXII capillary gel electrophoresis (CGE) instrument (Caliper Life Sciences). Glycostructures may also be analysed by mass spectrometry.

EXAMPLES

Example 1: First microRNA Screen in BIWA4-Producing CHO Cells

CHO cells are commonly used for the production of therapeutic proteins. Genetic engineering approaches have attempted to optimize the productivity of these cells by expressing specific cDNAs. Naturally existing non-coding RNAs regulate cell fate by modulating the expression of a whole set of target proteins, which may possibly result in a super-secretory phenotype when ectopically expressed in CHO producer cells. To exploit the power of non-coding RNAs and identify those that positively affect secretion of a heterologous protein, CHO-DG44 cells stably expressing an IgG1 (BIWA4) are transiently transfected by nucleofection with a human microRNA mimic library consisting of 879 microRNAs (FIG. 1). Antibody concentrations in the supernatant of the transfected cells are determined on days 3 and 4 post transfection by ELISA. The experiment is repeated and 20 microRNAs that (i) increased the IgG1 titer in the supernatant more than 1.3-fold on day 3 or 4 compared to control cells and (ii) increased the mean IgG1 titer of both experiments on day 3 or 4 more than 1.4-fold are defined as hits. Given that the host cell already produces high amounts of heterologous protein, a further increase in productivity of >30% is highly significant. Names and sequences of the 20 microRNAs are listed in FIG. 1B.

Example 2: Secondary Screen in BIWA4-Producing CHO Cells

Figure 2:
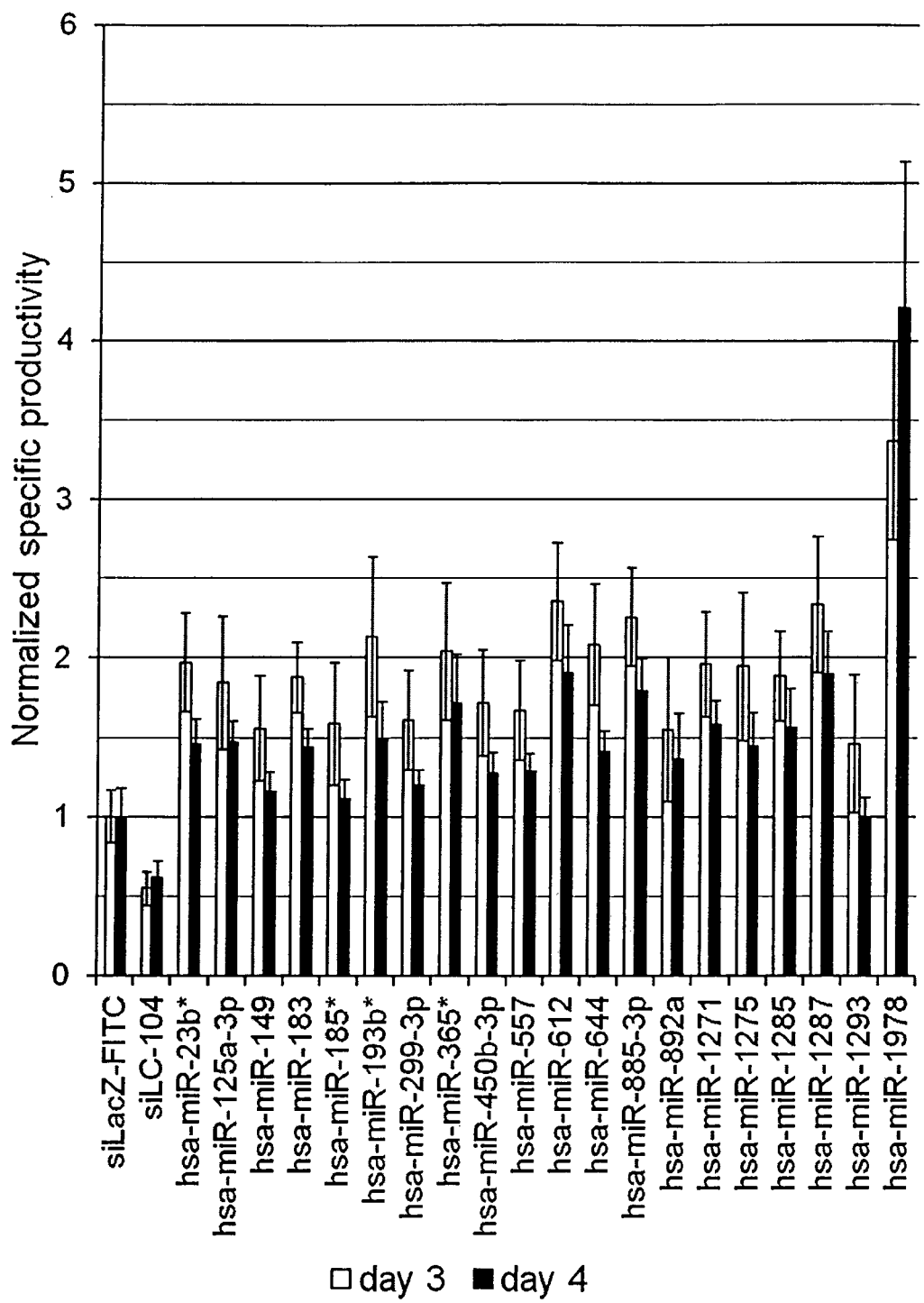

To validate the hits from the primary screen performed in a 96-well format, a secondary screen with BIWA4-producing CHO cells is performed in a larger culture format (12-well) with quadruplicate samples (FIG. 2). In addition to measuring the IgG titer in the supernatant, cell density and viability are determined enabling the calculation of the specific productivity. Remarkably, in the secondary screen, all 20 microRNAs defined as hits in the primary screen increased the specific productivity of host cells determined on day 3 and/or 4 post transfection.

Example 3: Transient Expression of miRNAs in BIBH1-Producing CHO Cells

Figure 3:
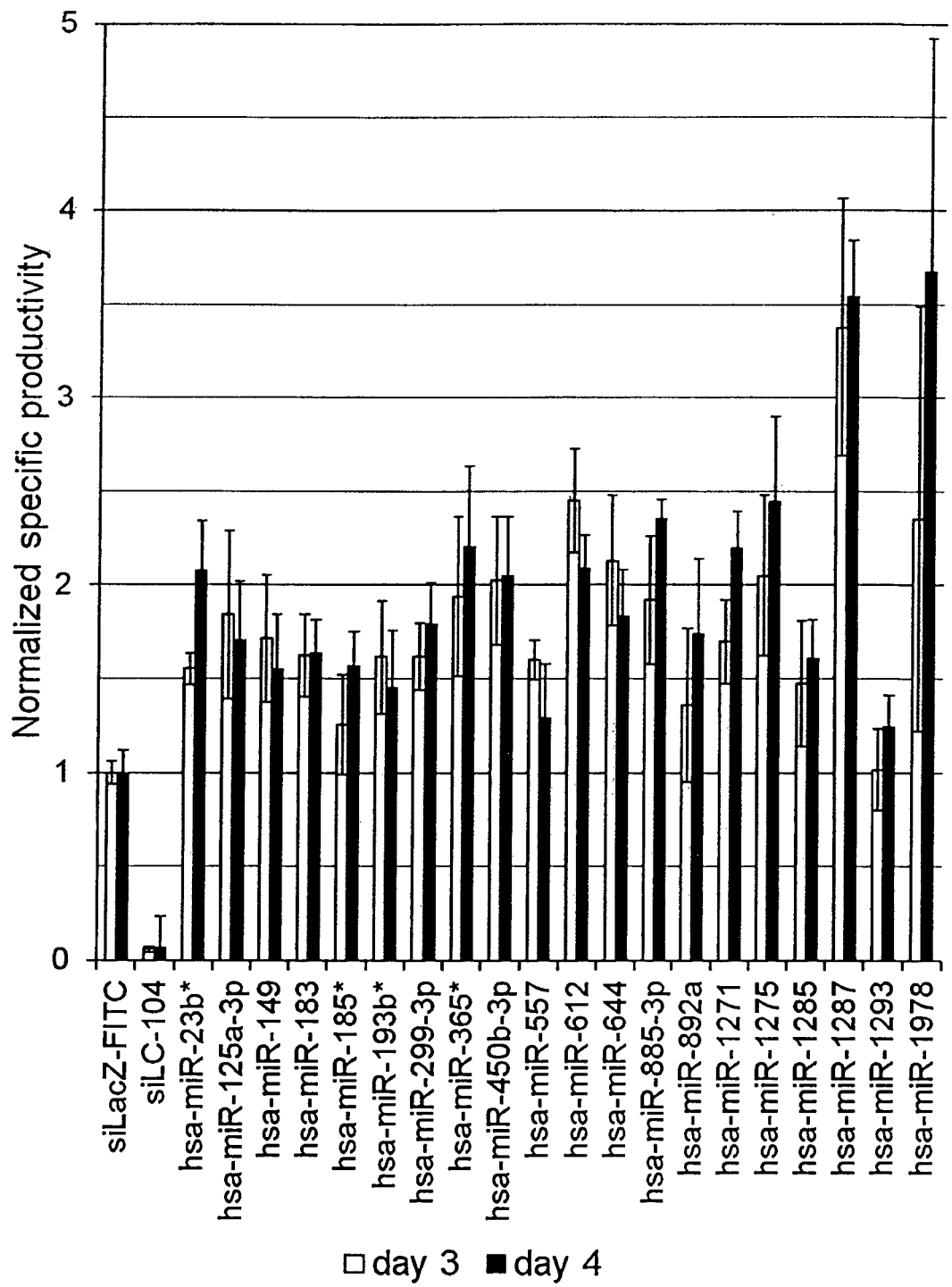

To explore whether the increased specific productivity was specific to BIWA4-producing CHO cells or could equally be seen in another IgG1-producing CHO cell line, CHO cells stably expressing another IgG1 (BIBH1) are transiently transfected with each of the 20 microRNAs as described in Example 2 and their specific productivity is determined (FIG. 3). Surprisingly, all 20 microRNAs that are confirmed as hits in the secondary screen with BIWA1-producing CHO cells also increase the specific productivity of BIBH1-producing CHO cells on day 3 and/or 4 post transfection.

Example 4: Transient Expression of miRNAS in HSA-Producing CHO Cells

Figure 4:
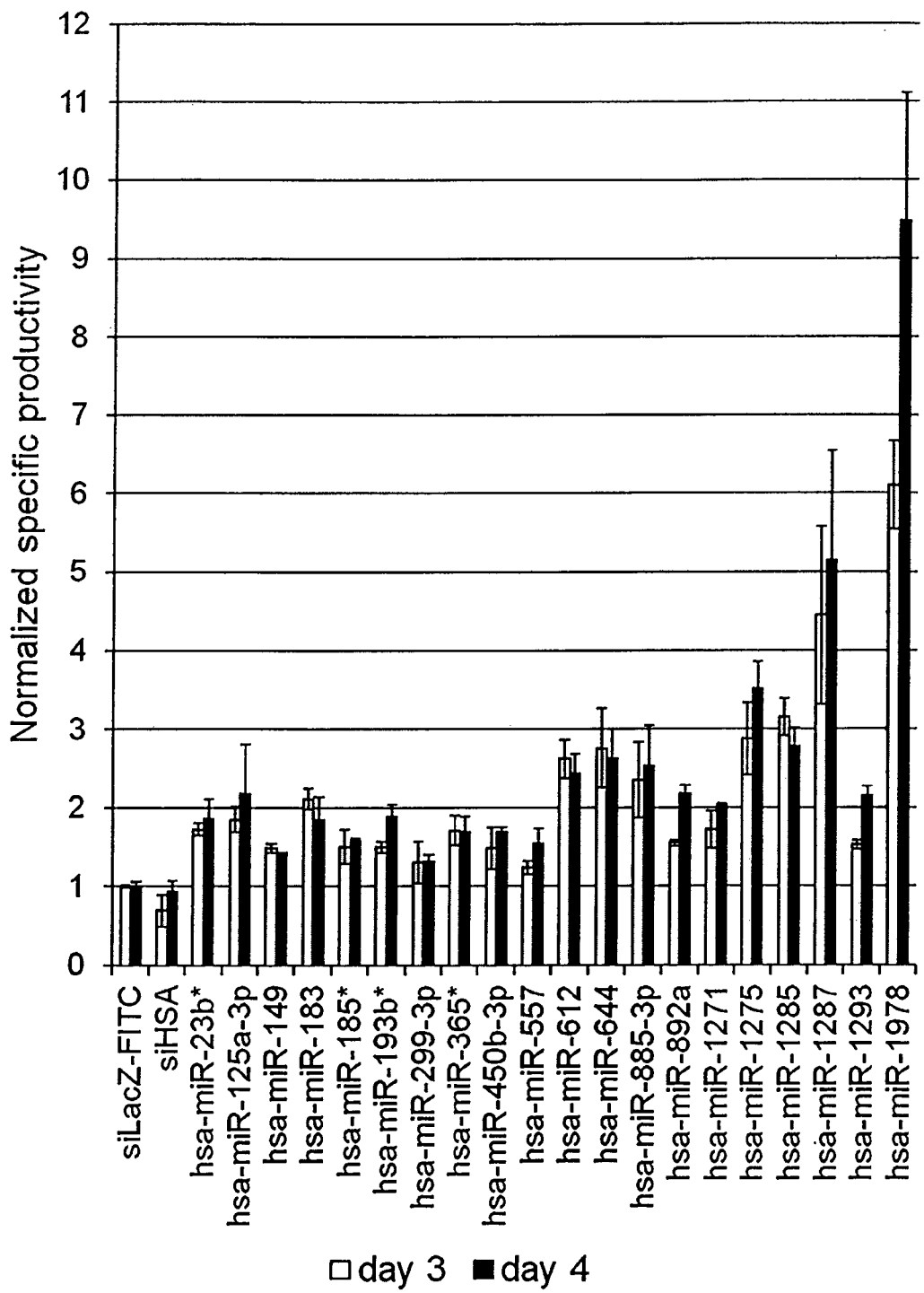

To explore whether transient expression of the 20 microRNAs specifically enhanced the expression and secretion of IgG1 molecules or also elevates the production of other therapeutic proteins, such as human serum albumin (HSA), CHO cells stably expressing HSA are transiently transfected with each of the 20 microRNAs as described in example 2 and their specific productivity is determined (FIG. 4). Surprisingly, all 20 microRNAs also exert a positive effect on the specific productivity of HSA-secreting CHO cells on days 3 and 4 post transfection, providing evidence that the microRNAs function in a product-independent manner.

Example 5: Analysis of miRNA Expression in Transfected BIWA4-Producing CHO Cells by Quantitative PCR We transiently transfect BIWA4 cells with either a plasmid encoding microRNA hsa-miR-557 (pBIP-1-mir-gen-.miR-557) or with the mature miRNA hsa-miR-557 as described in Example 1. Control cells are transfected with an empty vector (pBIP-1) or with a control siRNA (siLacZ). To validate the expression of transiently transfected microRNAs, we isolate RNA from all cells two days after transfection and perform qPCR analysis of the mature miRNA sequence and the antisense strand of the pre-miRNA. Indeed, we detect strongly increased levels of mature miRNA sequence in cells transfected with the mature miRNA compared to control cells (FIG. 5). Further, we also detect increased levels of the mature miRNA in cells transfected with the miRNA-encoding plasmid whereas the level of the antisense strand is comparable to the controls. This demonstrates that transfection of both mature and plasmid-encoded microRNAs leads to increased levels of the respective microRNA in CHO cells, indicating that CHO cells are able to correctly process human microRNA precursors into their mature form.

Example 6: Expression of miRNA Combinations in BIWA4-Producing CHO Cells

Furthermore, we explore whether a combination of these microRNAs further boosts the specific productivity of BIWA4-producing CHO cells.

Figure 6:
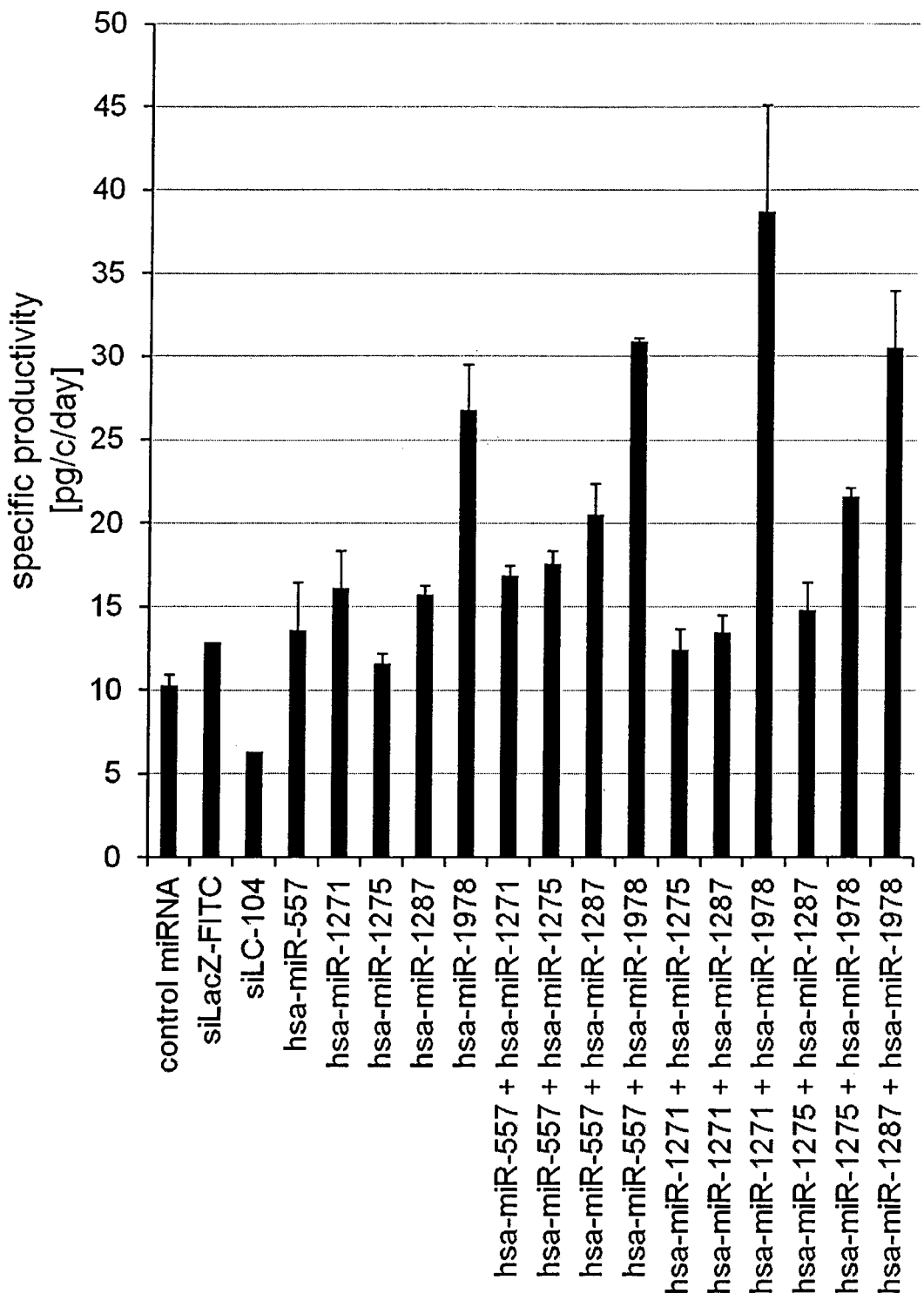

For this purpose, CHO-DG44 cells stably secreting an IgG1 (BIWA4) are transiently transfected with a combination of 2 validated miRNA hits (every possible combination of these 5 miRNAs: hsa-miR-557, hsa-miR-1271, hsa-miR-1275, hsa-miR-1287 and hsa-miR-1978) in duplicates. Samples containing a single microRNA are adjusted to a final RNA concentration by adding mimic miRNA negative control. Transfection efficiency is monitored by flow cytometry of siLacZ-FITC transfected cells and ELISA analysis of the supernatant of siLC-104 (targeting the light chain of the antibody) transfected cells. As negative controls a non targeting siRNA (siLacZ-FITC) and a mimic miRNA are used (error bars=SEM of duplicates). Cell density and antibody concentration in the supernatant are determined on day 1-4 and specific productivity is calculated (FIG. 6).

Remarkably, the combined transfection of two different miRNAs enhanced specific productivity on day 4 compared to singly transfected CHO-DG44 cells in about 50% of the cases tested: E.g. co-transfection of miR-557 and miR-1287 has a clearly positive effect in increasing the productivity compared to both microRNAs alone. These data show that with certain combinations of microRNAs, it is possible to achieve an additive (and maybe even synergistic) effect on the enhancement of secretive capacity of a cell producing a therapeutic protein of interest.

Example 7: Transient Expression of miRNAs in Insulin-Secreting INS Cells

To explore whether transient expression of microRNAs enhances the secretion of an endogenous protein, INS-1 cells, a rat insulinoma cell line, which secretes insulin, are transiently transfected with a subset of the 20 microRNAs (hsa-miR-183, hsa-miR-125-3p, hsa-miR-557, hsa-miR-1271, hsa-miR-1275, hsa-miR-1287). Starved cells are stimulated with glucose for 15 minutes or left untreated.

Basal and glucose-induced insulin concentrations in the supernatant of the cells are determined by ELISA. Surprisingly, all 6 microRNAs exert a positive effect on basal and glucose-stimulated insulin secretion of INS1 cells on day 3 post transfection (FIG. 7), providing further evidence that these microRNAs function in a species- and product-independent manner and also positively affect the secretion of endogenous proteins not only in CHO, but also in other cells of rodent origin.

Example 8: Transient Expression of miRNAs in ssHRP-Producing Human HEK293 FlpIN Cells To explore whether transient expression of microRNAs enhances the constitutive secretion of a model cargo protein in human cells, HEK293FlpIn cells stably and inducibly expressing a secretable form of horse radish peroxidase (ssHRP) are transiently transfected with 5 microRNAs by lipofection. Two days post transfection, ssHRP expression is induced by addition of doxycycline. 12 hours after induction the amount of ssHRP in the supernatant of the cells is determined after 5 hours, quantified by addition of ECL reagent and measurement of the luminescent signal in plate reader. Luminescence signals are normalized for cell density. 5 microRNAs (hsa-miR-1287, hsa-miR-183, hsa-miR-557, hsa-miR-612 and hsa-miR-644) exerted a positive effect on ssHRP secretion of human HEK293 FlpIn cells (FIG. 8), providing evidence that the microRNAs function in a species- and product-independent manner.

Example 9: Stable Expression of a miRNA in BIWA4-Producing CHO Cells

Figure 11:
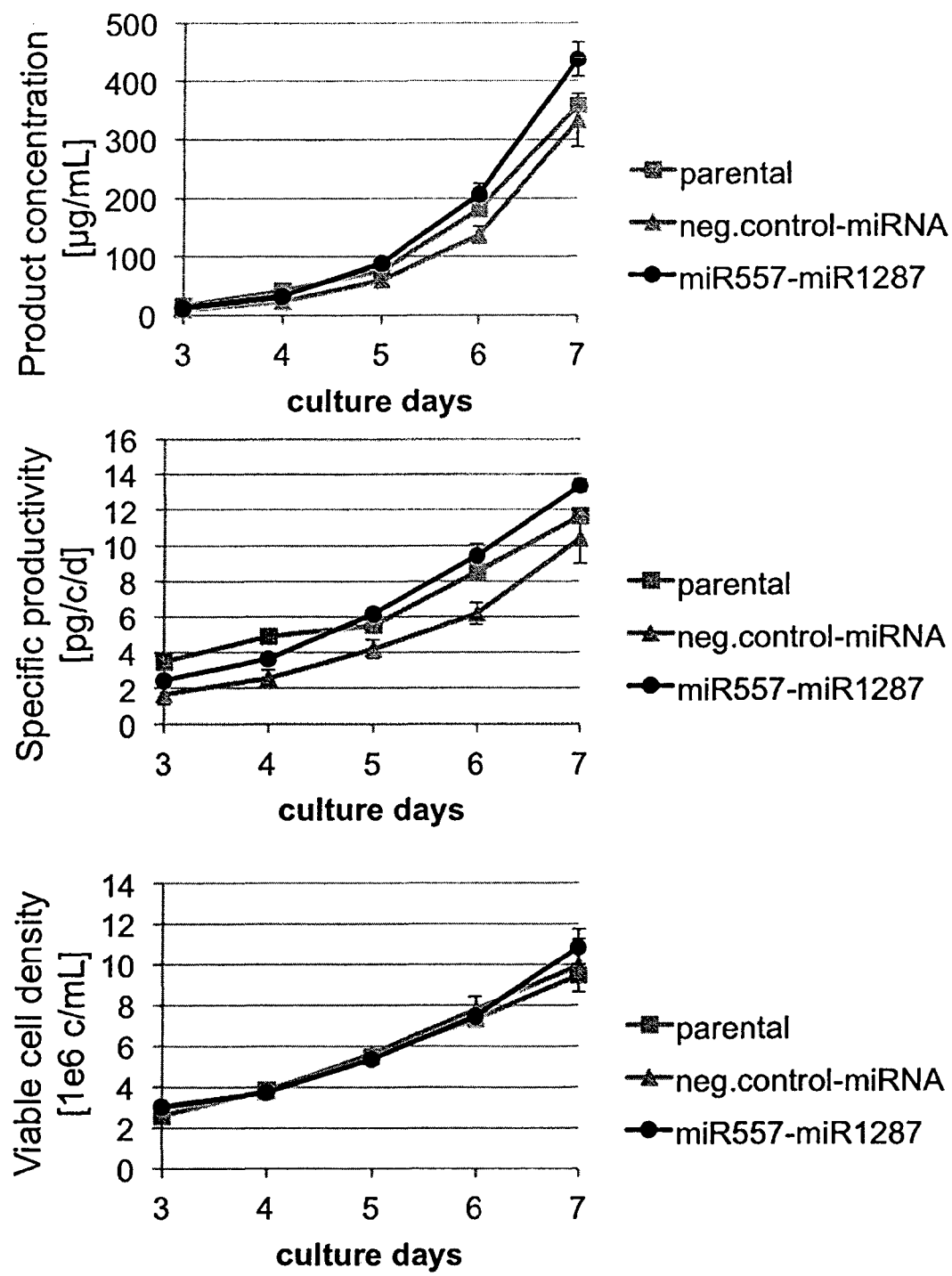

CHO-DG44 cells stably expressing an IgG1 (BIWA4) are transfected with an expression construct encoding a non-coding RNA (see FIG. 1B) and subsequently subjected to selection to obtain stable cell pools. The expression construct may contain two or more copies of the same or different non-coding RNAs. During subsequent passages, supernatant is taken from seed-stock cultures of all stable cell pools; the IgG titer is determined by ELISA and divided by the mean number of cells to calculate the specific productivity. The highest values are seen in the cell pools harbouring the non-coding RNAs. IgG expression is markedly enhanced compared to MOCK or untransfected cells. Very similar results can be obtained if the stable transfectants are subjected to batch or fed-batch fermentations (FIG. 11). In each of these settings, overexpression of non-coding RNAs leads to increased antibody secretion, indicating that non-coding RNAs are able to enhance the specific production capacity of the cells grown in serial cultures or in bioreactor batch or fed batch cultures.

Example 10: Stable Expression and Amplification of a miRNA in Rituximab-Producing CHO Cells Parental CHO-DG44 cells are either sequentially or concomitantly transfected with three expression plasmids: (i) a plasmid encoding the light chain of the antibody Rituximab and containing a DHFR cassette for amplification, (ii) a plasmid encoding the heavy chain of Rituximab and containing a neomycin resistance cassette, and (iii) a plasmid encoding a microRNA (see FIG. 1B) and containing a puromycin resistance cassette. Cells with stable genomic integration are obtained by puromycin and neomycin selection and the simultaneous removal of hypoxantin/thymidine. Then, amplification of the light chain of the antibody is achieved by the successive increase of the concentration of methothrexate in the medium. It is expected that the light chain and the microRNA are co-amplified through indirect mechanisms. During subsequent passages of stable CHO-DG44 cells expressing Rituximab and the non-coding RNA, supernatant is taken from seed-stock cultures of all stable cell pools; the Rituximab titer is determined by ELISA and divided by the mean number of cells to calculate the specific productivity. The highest values are seen in the cell pools harbouring the amplified non-coding RNA. Rituximab expression is markedly enhanced compared to cells without stable expression of the non-coding RNA. Very similar results can be obtained if the stable transfectants are subjected to batch or fed-batch fermentations. In each of these settings, overexpression of the non-coding RNA leads to increased antibody titers, indicating that non-coding RNAs are able to enhance the specific production capacity of the cells grown in serial cultures or in bioreactor batch or fed batch cultures.

Example 11: Generation of an Optimized Host Cell for Production of Therapeutic Proteins To be more flexible in the application of microRNA engineering, we also generate CHO host cells which are stably engineered to exhibit increased levels of either one or a combination of the microRNAs provided in the present invention. In a second step, these engineered host cells and un-engineered control host cells are then transfected with an expression construct encoding a protein of interest and productivities and titers of said protein is then analyzed both in seed-stock cultures and fed-batch processes.

The results demonstrate that production cells derived from microRNA engineered host cells show higher secretion rates, i.e. productivities as well as in most cases also higher titers. Hence, we conclude that microRNA engineering can either be done after, prior to or simultaneously to introducing the protein of interest with similar results, thus offering a broad range of options for applications in pharmaceutical development processes.

Alternatively, sufficiently high stable levels of microRNA in the host cell or the producer cell can be achieved by cloning multiple copies of the microRNA into an expression vector.

Example 12: Expression of Therapeutic Proteins from a Secretion Optimized Host Cell To test the production performance of microRNA-engineered cells generated by either of the methods described in examples 3, 6, 11 or in the detailed description of the invention using amplification of miRNAs, they are subjected to fed-batch processes in chemically-defined media to reflect the conditions in industrial processes. The fed-batch is performed in shake flasks that are previously demonstrated to be a predictive screening model for performance in larger scales. The process is run over >7 days. Cell counts, viabilities and product titers are measured at regular intervals to monitor the production behavior of microRNA engineered cells as well as non-engineered cell lines which are included as controls.

This experiment shows that growth and viability profiles of microRNA engineered cells are comparable or only slightly lower compared to controls. However, the specific productivity of microRNA engineered cells is consistently higher compared to non-engineered cell lines which proved the benefit of this microRNA engineering approaches for industrial therapeutic protein production processes.

Example 13: Analysis of microRNA Expression in Stably Transfected BIWA4-Producing CHO Cells by Flow Cytometry BIWA4 cells are stably transfected with a plasmid encoding a GFP cassette plus two microRNA copies (pcDNA6.2-GW/emGFP-miR557-miR557, pcDNA6.2-GW/emGFP-miR1287-miR1287) or a combination of the individual microRNAs (pcDNA6.2-GW/emGFP-miR557-miR1287). After selection with blasticidin S (encoded on the pcDNA6.2-GW/emGFP vector) cells are sorted based on their GFP fluorescence. Control cells are untransfected parental cells. To validate the expression of stably transfected microRNAs, cells are analyzed by flow cytometry for GFP expression, which correlates with microRNA expression, and GFP positive populations can be detected over 51 days (FIG. 9). This shows that CHO cells are able to stably overexpress human microRNAs for at least 7 weeks.

Example 14: Analysis of microRNA Expression in Stably Transfected BIWA4-Producing CHO Cells by Quantitative PCR BIWA4 cells are stably transfected with a plasmid encoding a GFP cassette plus two microRNA copies (pcDNA6.2-GW/emGFP-miR557-miR557, pcDNA6.2-GW/emGFP-miR1287-miR1287) or the combination of the individual microRNAs (pcDNA6.2-GW/emGFP-miR557-miR1287). After selection with blasticidin S (encoded on the pcDNA6.2-GW/emGFP vector) cells are sorted based on their GFP fluorescence. Cells transfected with the mature miRNAs (hsa-miR-557 or hsa-miR-1287) as described in Example 1 are used as positive controls. Cell pools stably expressing the control vector (pcDNA6.2-GW/emGFP-neg. control miRNA) and untransfected parental cells (BIWA4) served as negative controls. To validate the expression of stably transfected microRNAs, we isolate RNA from all cells and perform qPCR analysis of the mature miRNA sequence. Increased levels of the mature miRNA are detected in cells transfected with the miRNA-encoding plasmid, whereas hardly any signal is detectable in control vector transfected cells and parental cells (FIG. 10). This demonstrates that stable genomic integration of plasmid-encoded microRNAs leads to increased levels of the respective microRNA in CHO cells and shows that CHO cells are able to correctly process human microRNA precursors into their mature form.

Example 15: Fed-Batch Cultivation of Stable miRNA Overexpressing BIWA4-Producing CHO Cells CHO-DG44 stably secreting an IgG1 (BIWA4) were stably transfected with miRNA expression vectors (pcDNA6.2-GW/emGFP) and single clones were generated by limited dilution. Either a combination of 2 validated miRNA hits (-miR557-miR1287-clone) or the respective empty vector control expressing GFP (-control-clone) were used during fed-batch cultures. Three independent pools stably expressing a neg. control miRNA (pcDNA6.2-GW/emGFP-neg. control-miRNA) served as further controls. Cell density and antibody concentration in the supernatant were determined on day 3-11 by cell counting with trypane blue exclusion and ELISA analysis, respectively, and specific productivity was calculated. The highest titres and specific productivity are seen in the cells co-expressing the non-coding RNAs (hsa-miR-557 and hsa-miR-1287). IgG expression is markedly enhanced compared to the negative control (pcDNA6.2-GW/emGFP-neg. control miRNA) or parental cells (FIG. 11). This proves that stable clones of CHO cells expressing selected non-coding RNAs have an increased titre and specific production capacity, without any negative effect on viable cell density, when grown in fed batch cultures.

Example 16: Stable Single Clones of miRNA Overexpressing BIWA4-Producing CHO Cells CHO-DG44 cells stably expressing an IgG1 (BIWA4) are transfected with an expression construct encoding non-coding RNAs (see FIG. 1B) and are subjected to selection to obtain stable cell pools that are subsequently used to generate single clones. The expression construct contains a combination of non-coding RNAs (pcDNA6.2-GW/emGFP-miR557-miR1287). During fed-batch cultivation supernatant is taken from the single clone; the IgG titer is determined by ELISA and divided by the mean number of cells to calculate the specific productivity. The highest values are seen in the cells co-expressing the non-coding RNAs (hsa-miR-557 and hsa-miR-1287). IgG expression is markedly enhanced compared to the negative control pools (pcDNA6.2-GW/emGFP-neg. control miRNA) or control clone (FIG. 12). This proves that stable single clones of CHO cells expressing selected non-coding RNAs have an increased specific production capacity when grown in fed batch cultures.

Example 17: Analysis of Antibody Glycosylation

To elucidate the structure and composition of the Fc-glycosylation of IgGs produced in the miRNA cell lines, the glycans are released from the purified antibody after reduction by enzymatic digestion with PNGase F. The antibody glycosylation pattern was analyzed with the PROFILER-PRO Glycan Profiling Kit Ver 2 on a LABCHIP GXII capillary gel electrophoresis (CGE) instrument (Caliper Life Sciences) according to the manufacturer's protocol. Electropherograms were analyzed by the LABCHIP GX software package to identify and quantify the individual sugar structures. All values are normalized to 100% total sugar structures per sample. The results in FIGS. 13A and 13B show that the microRNAs provided herein do not affect glycosylation of the protein-of-interest, such as in the Fc-domain of an antibody.

Figure 14:
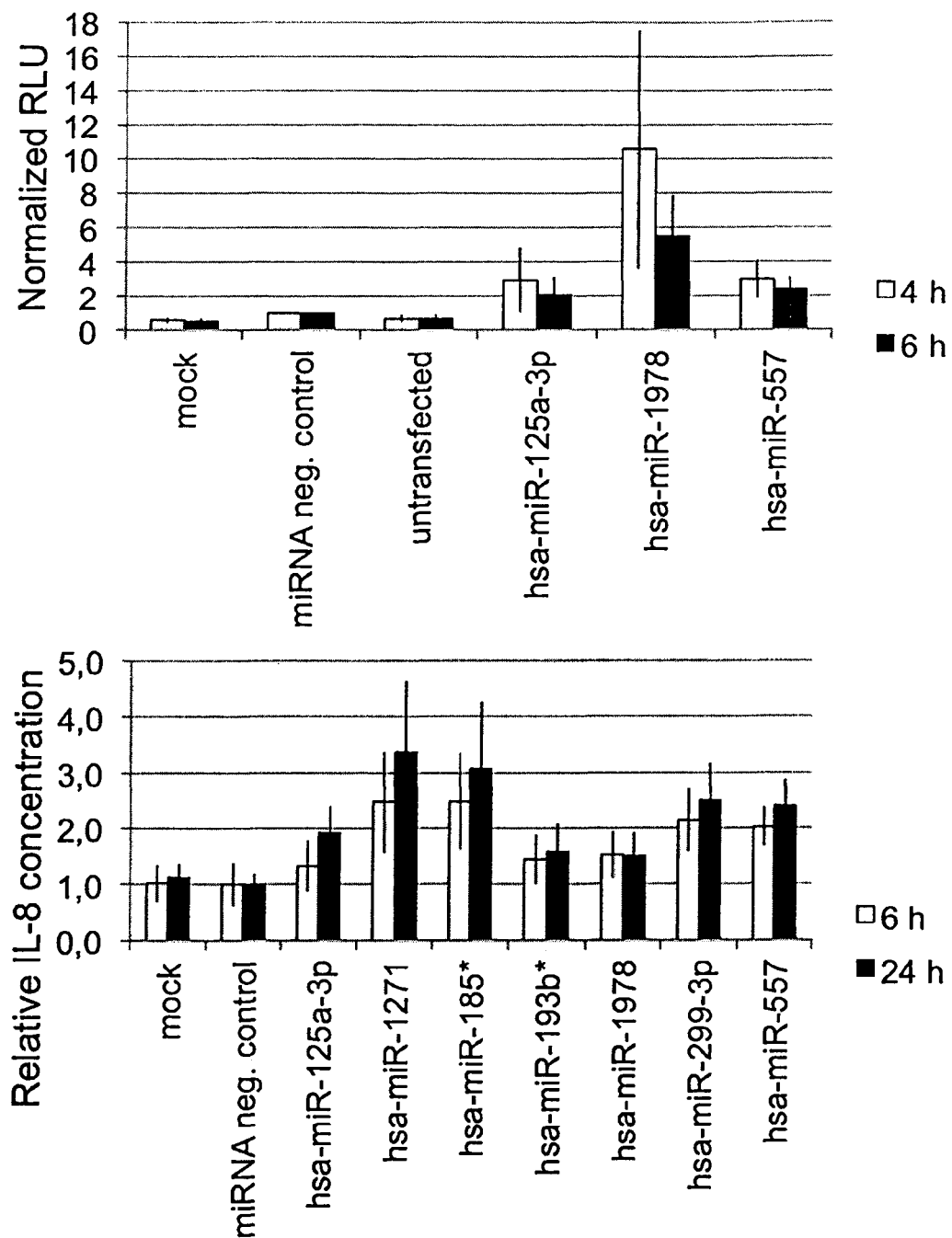

Example 18: Transient Expression of miRNAs in HeLa Cells Transiently Expressing ssHRP To explore whether transient expression of microRNAs enhances the constitutive secretion of a model cargo protein in human cells, HeLa cells are transiently transfected with 3 microRNAs by lipofection. Two days post transfection, ssHRP-FLAG is transiently transfected and 24 hours later the amount of ssHRP in the supernatant of the cells is determined after 4 and 6 hours, quantified by addition of ECL reagent and measurement of the luminescent signal in plate reader. All three microRNAs (hsa-miR-125a-3p, hsa-miR-1978 and hsa-miR-557) tested exerted a positive effect on ssHRP secretion of human Hela cells (FIG. 14, top panel), providing evidence that the microRNAs function in a species- and product-independent manner.

Example 19: Transient Expression of miRNAs in HeLa Cells Endogenously Secreting IL-8

To explore whether transient expression of microRNAs enhances the constitutive secretion of an endogenous model cargo protein in human cells, Hela cells are transiently transfected with 7 microRNAs by lipofection. Two days post transfection the amount of IL-8 in the supernatant of the cells is determined after 6 and 24 hours, quantified by ELISA analysis. All 7 microRNAs (hsa-miR-125a-3p, hsa-miR-1271, hsa-miR-185*, hsa-miR-193b*, hsa-miR-1978, hsa-miR-299-3p and hsa-miR-557) tested exerted a positive effect on IL-8 secretion of human Hela cells (FIG. 14, bottom panel), providing evidence that the microRNAs function in a species- and product-independent manner.

Sequence Table
SEQ ID NO 1: miR-125a-3p
SEQ ID NO 2: miR-149
SEQ ID NO 3: miR-1271
SEQ ID NO 4: miR-1275
SEQ ID NO 5: miR-1285
SEQ ID NO 6: miR-1287
SEQ ID NO 7: miR-1293
SEQ ID NO 8: miR-183
SEQ ID NO 9: miR-185*
SEQ ID NO 10: miR-193b*
SEQ ID NO 11: miR-1978
SEQ ID NO 12: miR-23b*
SEQ ID NO 13: miR-299-3p
SEQ ID NO 14: miR-365*
SEQ ID NO 15: miR-450b-3p
SEQ ID NO 16: miR-557
SEQ ID NO 17: miR-612
SEQ ID NO 18: miR-644a
SEQ ID NO 19: miR-885-3p
SEQ ID NO 20: miR-892a
SEQ ID NO: 21: hsa-miR-557 forward
SEQ ID NO: 22: hsa-miR-557 reverse
SEQ ID NO: 23: hsa-miR-1287 forward
SEQ ID NO: 24: hsa-miR1287 reverse
SEQ ID NO: 25: hsa-miR1978 forward
SEQ ID NO: 26: hsa-miR1978 reverse

REFERENCE LIST

Barron N, Kumar N, Sanchez N, Doolan P, Clarke C, Meleady P, O'Sullivan F, Clynes M. (2011). Engineering CHO cell growth and recombinant protein productivity by overexpression of miR-7; J Biotechnol. Jan. 20; 151(2): 204-11.

Barron N, Sanchez N, Kelly P, Clynes M. (2011). MicroR-NAs: tiny targets for engineering CHO cell phenotypes? Biotechnol Lett. Jan.; 33(1):11-21.

Clarke, C., Doolan, P., Barron, N., Meleady, P., O'Sullivan, F., Gammell, P., Melville, M., Leonard, M., Clynes, M. (2011). Large scale microarray profiling and coexpression network analysis of CHO cells identifies transcriptional modules associated with growth and productivity; Journal of Biotechnology, 155 (3), pp. 350-359.

Edelman, G. M., Cunningham, B. A., Gall, W. E., Gottlieb, P. D., Rutishauser, U., and Waxdal, M. J. (1969). The covalent structure of an entire gammaG immunoglobulin molecule. Proc. Natl. Acad. Sci. U. S. A 63, 78-85.

Ellison, J. and Hood, L. (1982). Linkage and sequence homology of two human immunoglobulin gamma heavy chain constant region genes. Proc. Natl. Acad. Sci. U. S. A 79, 1984-1988.

Gammell, P., Barron, N., Kumar, N., Clynes, M. (2007); Initial identification of low temperature and culture stage induction of miRNA expression in suspension CHO-K1 cells; Journal of Biotechnology, 130 (3), pp. 213-218.

Jadhav, V., Hackl, M., Hernandez Bort, J. A., Wieser, M-, Harreither, E., Kunert, R., Borth, N., Grillari, J., (2012); A Screening method to assess biological effects of microRNA overexpression in Chinese hamster ovary cells, 109 (6), 1376-1385.

Johnson, K. C., Jacob, N. M., Nissom, P. M., Hackl, M., Lee, L. H., Yap, M., Hu, W.-S. (2011); Conserved MicroRNAs in Chinese hamster ovary cell lines; Biotechnology and Bioengineering, 108 (2), pp. 475-480.

Kabat, E. A. (1988). Antibody complementarity and antibody structure. J. Immunol. 141, S25-S36.

Kabat, E. A., Wu, T. T., Perry, H. M., Gottesman, K. S., and Foeller, C. (1991). Sequences of Proteins of Immunological Interest. U. S. Department of Health and Human Services, Natl. Inst. of Health, Bethesda.

Kaufman, R. J. (1990). Selection and coamplification of heterologous genes in mammalian cells. Methods Enzymol. 185, 537-566.

Lagos-Quintana M., Rauhut, R., Yalcin, A., Meyer, J., Lendeckel, W., Tuschl, T., (2002) Identification of tissue-specific microRNAs from mouse, Curr Biol. 30; 12(9): 735-9.

Lin N, Heuermann K, Schlueter J, Kreader C, Knight S, Kayser K (2011). Effects of Inhibiting Two Cell Cycle Modulating microRNAs in Recombinant Human IgG Producing Chinese Hamster Ovary Cells; SAFC presentation safcglobal.com Müller D, Katinger H, Grillari J. MicroRNAs as targets for engineering of CHO cell factories (2008). Trends Biotechnol. Jul.; 26(7):359-65. Pau et al. (2001). The human cell line PER.C6 provides a new manufacturing system for the production of influenza virus vaccines; Vaccines 19: 2716-2721.

Pitot, H C, Peraino C, Morse, P A, Potterm V R (1964). Hepatomas in tissue culture compared with adapting liver in vivo. Natl. Cancer Inst. Monogr. 13: 229-245, 1964. PMID: 14143233

REUBER, M. D. (1961). A transplantable bile-secreting hepatocellular carcinoma in the rat. J. Natl. Cancer Inst. 26, 891-899.

Sambrook, J., Fritsch, d. F., and Maniatis, T. (1989). Molecular Cloning: A Laboratory Manual. (Cold Spring Harbor: Cold Spring Harbor Laboratory Press).

Urlaub, G., Kas, E., Carothers, A. M. and Chasin L. A. (1983) Deletion of the Diploid Dihydrofolate Reductase Locus from Cultured Mammalian Cells, Cell 1983(33) 405-412.

Gail Urlaub, Pamela J. Mitchell, Emmanuel Kas, Lawrence A. Chasin, Vicky L. Funanage, T. Timothy Myoda, Joyce Hamlin Effect of gamma rays at the dihydrofolate reductase locus: Deletions and inversions. Somatic Cell and Molecular Genetics November 1986, Volume 12, Issue 6, pp 555-566 Wolfel J, Essers R, Bialek C, Hertel S, Scholz-Neumann N, and Schiedner G (2011). CAP-T cell expression system: a novel rapid and versatile human cell expression system for fast and high yield transient protein expression; BMC Proc. 2011; 5(Suppl 8): P133.

What is claimed is:

1. A method of developing a stably transfected mammalian cell comprising the following steps:
   (a) transfecting the mammalian cell with an expression vector encoding a selectable marker and at least one microRNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20,
   (b) cultivating said cell for an initial period of time in the presence of selective pressure, and
   (c) selecting the transfected cell.

2. The method of claim 1, wherein the mammalian cell in step (a) is a producer host cell additionally comprising at least one expression vector comprising at least one gene of interest.

3. The method of claim 1, wherein the mammalian cell is a rodent cell or a human cell.

4. The method of claim 3, wherein the rodent cell is a Chinese Hamster Ovary (CHO) cell.

5. The method of claim 1, wherein the mammalian cell in step (a) is transfected with an expression vector comprising a polynucleotide sequence encoding a microRNA selected from the group consisting of: SEQ ID NO:6, SEQ ID NO: 11, and SEQ ID NO: 16.

6. A method of producing a protein of interest, comprising the following steps:
   (a) transfecting at least one microRNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20, or an expression vector encoding said at least one microRNA, and at least one expression vector comprising at least one gene of interest encoding a protein of interest into a mammalian cell,
   (b) selecting a highly-productive transfected cell producing the protein of interest, wherein the production and/or secretion of the protein of interest is increased compared to a control cell, which is not transfected with said at least one microRNA or the expression vector encoding said at least one microRNA, and
   (c) cultivating the highly-productive transfected cell obtained in step (b) under conditions which allow expression of the gene(s) of interest.

7. The method of claim 6, further comprising a step (d) of harvesting and purifying the protein of interest.

8. The method of claim 6, wherein step (a) comprises transfecting an expression vector encoding said microRNA.

9. The method of claim 6, wherein the mammalian cell in step (a) is stably transfected with the expression vector encoding said microRNA.

10. The method of claim 6, wherein the mammalian cell in step (a) is transfected with an expression vector comprising a polynucleotide sequence encoding a microRNA selected from the group consisting of: SEQ ID NO: 6, SEQ ID NO: 11, and SEQ ID NO: 16.

11. The method of claim 6, wherein the expression vector comprising at least one gene of interest of step (a) also encodes the at least one microRNA of step (a).

12. The method of claim 6, wherein transfecting the microRNA or the expression vector encoding said microRNA is done after, prior to or simultaneously to transfecting the gene of interest.

13. The method of claim 6, wherein the protein of interest is a recombinant therapeutic protein.

14. The method of claim 6, wherein the protein of interest is an antibody or a Fc-fusion protein.

15. The method of claim 6, wherein the production and/or secretion of the protein of interest is increased by 10%, 20%, 50%, 100%, 200%, 400% compared to a control cell, which is not transfected with the expression vector encoding at least one microRNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

16. A method of preparing and selecting a recombinant mammalian cell, comprising the following steps:
- (a) transfecting a mammalian cell with genes that encode at least a protein or genes that encode at least a product of interest and a selectable marker, wherein the cell is co-transfected with at least one microRNA selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20, or an expression vector encoding said at least one microRNA,
- (b) selecting a cell with co-integrated genes by cultivating the cell in the presence of a selective agent, and
- (c) cultivating the cell under conditions which enable expression of the genes.

17. The method of claim 16 wherein the selectable marker confers resistance to neomycin, puromycin, bleomycin, zeocin or blasticidin.

18. The method of claim 16, wherein the selectable marker is an amplifiable selectable marker and further comprising an additional step (b') between steps (b) and (c), comprising amplifying the co-integrated genes by cultivating the cell in the presence of an agent which allows the amplification of the amplifiable selectable marker gene.

19. The method of claim 18, wherein the amplifiable selectable marker gene encodes the amplifiable selectable marker dihydrofolate reductase or glutamine synthetase.

20. The method of claim 16, wherein the mammalian cell in step (a) is stably transfected with an expression vector encoding said at least one microRNA.

21. The method of claim 16, wherein the mammalian cell in step (a) is transfected with an expression vector comprising a polynucleotide sequence encoding a microRNA selected from the group consisting of: SEQ ID NO:6, SEQ ID NO: 11, and SEQ ID NO: 16.

22. The method of claim 20, wherein the expression vector encoding said at least one microRNA is transfected after, prior to or simultaneously to transfecting the gene of interest.

* * * * *

UNITED STATES PATENT AND TRADEMARK OFFICE
CERTIFICATE OF CORRECTION

PATENT NO. : 11,230,725 B2
APPLICATION NO. : 15/727056
DATED : January 25, 2022
INVENTOR(S) : Florin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 506 days.

Signed and Sealed this
Twenty-ninth Day of November, 2022

Katherine Kelly Vidal
*Director of the United States Patent and Trademark Office*